(12) United States Patent
Diniz De Carvalho et al.

(10) Patent No.: US 11,560,558 B2
(45) Date of Patent: *Jan. 24, 2023

(54) METHODS OF CAPTURING CELL-FREE METHYLATED DNA AND USES OF SAME

(71) Applicants: University Health Network, Toronto (CA); Sinai Health System, Toronto (CA)

(72) Inventors: Daniel Diniz De Carvalho, Toronto (CA); Shu Yi Shen, Markham (CA); Rajat Singhania, Toronto (CA)

(73) Assignees: UNIVERSITY HEALTH NETWORK, Toronto (CA); SINAI HEALTH SYSTEM, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/519,350

(22) Filed: Nov. 4, 2021

(65) Prior Publication Data

US 2022/0073902 A1 Mar. 10, 2022

Related U.S. Application Data

(63) Continuation of application No. 17/353,756, filed on Jun. 21, 2021, which is a continuation of application No. 16/098,620, filed as application No. PCT/CA2017/000108 on May 3, 2017, now Pat. No. 11,078,475.

(60) Provisional application No. 62/331,070, filed on May 3, 2016.

(51) Int. Cl.

| C12N 15/10 | (2006.01) |
|---|---|
| C12Q 1/6806 | (2018.01) |
| C12Q 1/6804 | (2018.01) |
| G01N 33/53 | (2006.01) |
| C12Q 1/6886 | (2018.01) |
| C40B 30/04 | (2006.01) |

(52) U.S. Cl.
CPC ......... *C12N 15/1003* (2013.01); *C12N 15/10* (2013.01); *C12N 15/1093* (2013.01); *C12Q 1/6804* (2013.01); *C12Q 1/6806* (2013.01); *G01N 33/5308* (2013.01); *C12Q 1/6886* (2013.01); *C12Q 2600/154* (2013.01); *C40B 30/04* (2013.01)

(58) Field of Classification Search
CPC ...... C12Q 1/68; C12Q 1/6804; C12Q 1/6806; C12N 15/10; C12N 15/1003; C12N 15/1093
See application file for complete search history.

(56) References Cited

U.S. PATENT DOCUMENTS

| 11,078,475 B2* | 8/2021 | Diniz De Carvalho ..... G01N 33/5308 |
|---|---|---|
| 2003/0003455 A1 | 1/2003 | Rundell et al. |
| 2014/0080715 A1 | 3/2014 | Lo et al. |
| 2020/0308651 A1* | 10/2020 | De Carvalho ....... C12Q 1/6827 |
| 2021/0156863 A1* | 5/2021 | Dinz De Carvalho ..... C12Q 1/6806 |
| 2022/0119796 A1 | 4/2022 | Diniz De Carvalho et al. |

FOREIGN PATENT DOCUMENTS

| CN | 104781422 A | 7/2015 |
|---|---|---|
| WO | WO-2017190215 A1 | 11/2017 |

OTHER PUBLICATIONS

Feber et al., Genome Research 21:515-524 (Year: 2011).*
Fraga et al., Nucleic Acids Research 31(6) : 1765 (Year: 2003).*
Gao et al., Oncogene 34 : 1629 (Year: 2015).*
Gonzalgo et al., Genome Research 57: 594-599 (Year: 1997).*
Lienhard et al., Bioinformatics30(2) : 284-286 (Year: 2014).*
Rauch et al.Cancer Research66(16) :7939 (Year: 2006).*
Schwarzenbach et al., Nature Reviews | Genetics 11 : 426 (Year: 2011).*
Yagi et al., Genome Research 18 :1969 (Year: 2008).*
Akalin, et al., "MethylKit: A Comprehensive R Package for the Analysis of Genome-Wide DNA Methylation Profiles," *Genome Biology*, 13, RB7; 2012.
Aravanis, et al., "Next-Generation Sequencing of 34 Circulating Tumor DNA for Early Cancer Detection," *Cell*, 168(4); 571-574, 2017.
Bailey, et al., "Genomic Analyses Identify Molecular Subtypes of Pancreatic Cancer," *Nature*, 531(7592); 47-52, 2016.
Chiu, et al., "Noninvasive Prenatal Diagnosis of Fetal Chromosomal Aneuploidy by Massively Parallel Genomic Sequencing of DNA in Maternal Plasma," *PNAS*, 105(51); 20458-20463, 2008.
GTEx Consortium, "Human Genomics, The Genotype-Tissue Expression (GTEx) Pilot Analysis: Multitissue Gene Regulation in Humans," *Science*, 348(6235), 648-660, 2015.
Diaz & Bardelli, "Liquid Biopsies: Genotyping Circulating Tumor DNA," *Journal of Clinical Oncology*, 32(6); 579-586, 2014.
Fan, et al., "Noninvasive Diagnosis of Fetal Aneuploidy by Shotgun Sequencing DNA from Maternal Blood," *PNAS*, 105(42), 16266-16271; 2008.

(Continued)

*Primary Examiner* — Ethan C Whisenant
(74) *Attorney, Agent, or Firm* — Wilson Sonsini Goodrich & Rosati

(57) ABSTRACT

There is described herein, a method of capturing cell-free methylated DNA from a sample having less than 100 mg of cell-free DNA, comprising the steps of: subjecting the sample to library preparation to permit subsequent sequencing of the cell-free methylated DNA; adding a first amount of filler DNA to the sample, wherein at least a portion of the filler DNA is methylated; denaturing the sample; and capturing cell-free methylated DNA using a binder selective for methylated polynucleotides.

24 Claims, 34 Drawing Sheets

Specification includes a Sequence Listing.

(56) References Cited

OTHER PUBLICATIONS

Fang, et al., "Breast Cancer Methylomes Establish an Epigenomic Foundation for Metastasis," Science Translational Medicine, 3(75), 75fa25, 2011.
Fleischhacker & Schmidt, "Circulating Nucleic Acids (CNAs) and Cancer—A Survey," Biochimica et Biophysica Acta, 1775(1); 181-232, 2007.
Gu, et al., "Preparation of Reduced Representation Bisulfite Sequencing Libraries for Genome-Scale DNA Methylation Profiling," Nature Protocols, 6(4); 468-481, 2011.
Heinz, et al., "Simple Combinations of Lineage-Determining Transcription Factors Prime Cis-Regulatory Elements Required for Macrophage and B Cell Identities," Molecular Cell, 38(4); 576-589, 2010.
Heyn & Esteller, "DNA Methylation Profiling in the Clinic: Applications and Challenges," Nature Reviews Genetics, 13; 679-692, 2012.
Hinoue, et al., "Genome-Scale Analysis of Aberrant DNA Methylation in Colorectal Cancer," Genome Research, 22; 271-282, 2012.
Hoadley, et al., "Multiplatform Analysis of 12 Cancer Types Reveals Molecular Classification Within and Across Tissues of Origin," Cell, 158(4); 929-944, 2014.
Hu, et al., "DNA Methylation Presents Distinct Binding Sites for Human Transcription Factors," eLife, 2; e00726, 2013.
Hung, et al., "Detection of Circulating Fetal Nucleic Acids: A Review of Methods and Applications," Journal of Clinical Pathology, 62; 308-313, 2009.
International Search Report and Written Opinion Issued in Corresponding PCT Application No. PCT/CA2017/000108, dated Jun. 28, 2017.
Krueger & Andrews, "Bismark: A Flexible Aligner and Methylation Caller for Bisulfite Seq Applications," Bioinformatics, 27(11), 1571-1572, 2011.
Lehmann-Werman, et al., "Identification of Tissue-Specific Cell Death Using Methylation Patterns of Circulating DNA," PNAS Plus, 113; E1826-E1834, 2016.
Lienhard, el al., "MEDIPS: Genome-Wide Differential Coverage Analysis of Sequencing Data Derived from DNA Enrichment Experiments," Bioinformatics, 30(2), 284-286, 2014.
Lui, et al., "Predominant Hematopoietic Origin of Cell-Free DNA in Plasma and Serum After Sex-Mismatched Bone Marrow Transplantation," Clinical Chemistry, 48(3); 421-427, 2002.
Mack, et al., "Epigenomic Alterations Define Lethal CIMP-Positive Ependymomas of Infancy," Nature, 506(7489); 445-450, 2014.
Mikeska & Craig, "DNA Meethylation Biomarkers: Cancer and Beyond," Genes (Basel), 5(3); 821-864, 2014.
Newman, et al., "An Ultrasensitive Method for Quantitating Circulating Tumor DNA with Broad Patient Coverage," Nature Medicine, 20(5), 548-554, 2014.
Sharma, et al., Epigenetics in Cancer. Carcinogenesis, 31(1); 27-36, 2010.
Snyder, et al., "Cell-Free DNA Comprises an In Vivo Nucleosome Footprint That Informs its Tissues-of-Origin," Cell, 164(1-2);, 57-68, 2016.
Snyder, et al., "Universal Noninvasive Detection of Solid Organ Transplant Rejection," PNAS, 108(15); 6229-6234, 2011.
Stirzaker, et al., "Methylome Sequencing in Triple-Negative Breast Cancer Reveals Distinct Methylation Clusters With Prognostic Value," Nature Communications 6, 5899; 2015.
Sturm, ct al., "Hotspot Mutations in H3F3A and IDH1 Define Distinct Epigenetic and Biological Subgroups of Glioblastoma," Cancer Cell, 22(4); 425-437, 2012.
Su, et al., "A Gene Atlas of the Mouse and Human Protein-Encoding Transcriptomes,"PNAS, 101(16), 6062-6067, 2004.
Taiwo, et al., "Methylome Analysis Using MeDIP-seq with Low DNA Concentrations," Nature Protocols, 7; 617-636, 2012.
Varley, el al., "Dynamic DNA Methylation Across Diverse Human Cell Lines and Tissues," Genome Research, 23(3); 555-567, 2013.
Wu, et al., "BioGPS: Building Your Own Mash-Up of Gene Annotations and Expression Profiles," Nucleic Acids Research, 44(D1); D313-D316, 2016.
Zhao, et al., "Methylated DNA Immunoprecipitation and High-Throughput Sequencing (MeDIP-seq) Using Low Amounts of Genomic DNA," Cellular Reprogramming, 16; 1-10, 2014.
Neary, et al. Comparative analysis of MBD-seq and MeDIP-seq and estimation of gene expression changes in a rodent model of schizophrenia. Genomics. Jul. 2017;109(3-4):204-213. doi: 10.1016/j.ygeno.2017.03.004. Epub Mar. 29, 2017.
Akalin et al. MethylKit: A Comprehensive R Package for the Analysis of Genome-Wide DNA Methylation Profiles. Genome Biology 13(10):R87 (2012).
Aravanis, et al. Next-Generation Sequencing of Circulating Tumor DNA for Early Cancer Detection. Cell. Feb. 9, 2017;168(4):571-574. doi: 10.1016/j.cell.2017.01.030.
Bailey, et al. Genomic analyses identify molecular subtypes of pancreatic cancer. Nature. Mar. 3, 2016;531(7592):47-52. doi: 10.1038/nature16965. Epub Feb. 24, 2016.
Chiu, et al. Noninvasive prenatal diagnosis of fetal chromosomal aneuploidy by massively parallel genomic sequencing of DNA in maternal plasma. Proc Natl Acad Sci USA. Dec. 23, 2008;105(51):20458-20463. doi: 10.1073/pnas.0810641105. Epub Dec. 10, 2008.
Co-pending U.S. Appl. No. 17/353,756, inventors DE; Carvalho Daniel Diniz et al., filed on Jun. 21, 2021.
Diaz, et al. Liquid biopsies: genotyping circulating tumor DNA. J Clin Oncol. Feb. 20, 2014;32(6):579-586. doi: 10.1200/JCO.2012. 45.2011. Epub Jan. 21, 2014.
European search report and opinion dated Oct. 31, 2019 for EP Application No. 17792306.7.
Fan, et al. Noninvasive diagnosis of fetal aneuploidy by shotgun sequencing DNA from maternal blood. Proc Natl Acad Sci U S A. Oct. 21, 2008 ;105(42):16266-71. Epub Oct. 6, 2008.
Fang, et al. Breast cancer methylomes establish an epigenomic foundation for metastasis. Sci Transl Med. Mar. 23, 2011;3(75):75ra25. doi: 10.1126/scitranslmed.3001875.
Fleischhacker, et al. Circulating nucleic acids (CNAs) and cancer—a survey. Biochim Biophys Acta. Jan. 2007;1775(1):181-232. doi: 10.1016/j.bbcan.2006.10.001. Epub Oct. 7, 2006.
GTEx Consortium. Human genomics. The Genotype-Tissue Expression (GTEx) pilot analysis: multitissue gene regulation in humans. Science. May 8, 2015;348(6235):648-660. doi: 10.1126/science.1262110. Epub May 7, 2015.
Gu, et al. Preparation of reduced representation bisulfite sequencing libraries for genome-scale DNA methylation profiling. Nat Protoc. Apr. 2011;6(4):468-81. doi: 10.1038/nprot.2010.190. Epub Mar. 18, 2011.
Heinz, et al. Simple combinations of lineage-determining transcription factors prime cis-regulatory elements required for macrophage and B cell identities. Mol Cell. May 28, 2010;38(4):576-589. doi: 10.1016/j.molcel.2010.05.004.
Heyn, et al. DNA methylation profiling in the clinic: applications and challenges. Nature Reviews Genetics 13(10):679-692 (2012).
Hinoue, et al. Genome-scale analysis of aberrant DNA methylation in colorectal cancer. Genome Res. Feb. 2012;22(2):271-282. doi: 10.1101/gr.117523.110. Epub Jun. 9, 2011.
Hoadley, et al. Multiplatform analysis of 12 cancer types reveals molecular classification within and across tissues of origin. Cell. Aug. 14, 2014;158(4):929-944. doi: 10.1016/j.cell.2014.06.049. Epub Aug. 7, 2014.
Hu, et al. DNA methylation presents distinct binding sites for human transcription factors. Elife. Sep. 3, 2013;2:e00726. doi: 10.7554/eLife.00726.
Hung, et al. Detection of circulating fetal nucleic acids: a review of methods and applications. J Clin Pathol. Apr. 2009;62(4):308-313. doi: 10.1136/jcp.2007.048470.
International search report with written opinion dated Jun. 28, 2017 for PCT/CA2017/000108.
Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.

(56) References Cited

OTHER PUBLICATIONS

Lehmann-Werman, et al. Identification of tissue-specific cell death using methylation patterns of circulating DNA. Proc Natl Acad Sci USA 2016;113:E1826-34.

Lienhard, et al. MEDIPS: genome-wide differential coverage analysis of sequencing data derived from DNA enrichment experiments. Bioinformatics. Jan. 15, 2014;30(2):284-286. doi: 10.1093/bioinformatics/btt650. Epub Nov. 13, 2013.

Lui, et al. Predominant hematopoietic origin of cell-free DNA in plasma and serum after sex-mismatched bone marrow transplantation. Clin Chem. Mar. 2002;48(3):421-427.

Mack, et al. Epigenomic alterations define lethal CIMP-positive ependymomas of infancy. Nature. Feb. 27, 2014;506(7489):445-450. doi: 10.1038/nature13108. Epub Feb. 19, 2014.

Mikeska, et al. DNA methylation biomarkers: cancer and beyond. Genes (Basel). Sep. 16, 2014;5(3):821-864. doi: 10.3390/genes5030821.

Newman, et al. An ultrasensitive method for quantitating circulating tumor DNA with broad patient coverage. Nat Med. May 2014;20(5):548-54. Epub Apr. 6, 2014.

Notice of Allowance dated Mar. 19, 2021 for U.S. Appl. No. 16/098,620.

Office action dated Jun. 25, 2020 for U.S. Appl. No. 16/098,620.

Office action dated Dec. 21, 2020 for U.S. Appl. No. 16/098,620.

Sharma, et al. Epigenetics in cancer. Carcinogenesis. Jan. 2010; 31(1): 27-36. Published online Sep. 13, 2009. doi: 10.1093/carcin/bgp220.

Snyder et al. Cell-free DNA Comprises an In Vivo Nucleosome Footprint That Informs Its Tissues-of-Origin. Cell 164:57-68 (2016).

Snyder, et al. Universal noninvasive detection of solid organ transplant rejection. Proc Natl Acad Sci U S A. Apr. 12, 2011;108(15):6229-34. doi: 10.1073/pnas.1013924108. Epub Mar. 28, 2011.

Stirzaker et al: "Methylome sequencing in triple-negative breast cancer reveals distinct methylation clusters with prognostic value", Nature Communications, vol. 6, No. 5899, Jan. 1, 2015 (Jan. 1, 2015), XP055418632, GB ISSN: 2041-1723, DOI: 10.1038/ncomms6899.

Sturm, et al. Hotspot mutations in H3F3A and IDH1 define distinct epigenetic and biological subgroups of glioblastoma. Cancer Cell. Oct. 16, 2012;22(4):425-437. doi: 10.1016/j.ccr.2012.08.024.

Su, et al., "A gene atlas of the mouse and human protein-encoding transcriptomes", Proc Natl Acad Sci USA, Apr. 20, 2004, pp. 6062-6067, 101 (16).

Taiwo, et al. Methylome analysis using MeDIP-seq with low DNA concentrations. Nat Protoc. Mar. 8, 2012;7(4):617-636. doi: 10.1038/nprot.2012.012.

Varley, et al. Dynamic DNA methylation across diverse human cell lines and tissues. Genome Res. Mar. 2013;23(3):555-567. doi: 10.1101/gr.147942.112. Epub Jan. 16, 2013.

Wu, et al. BioGPS: building your own mash-up of gene annotations and expression profiles. Nucleic Acids Res. Jan. 4, 2016;44(D1):D313-316. doi: 10.1093/nar/gkv1104. Epub Nov. 17, 2015.

Xiang, et al. DNA methylome profiling of maternal peripheral blood and placentas reveal potential fetal DNA markers for non-invasive prenatal testing. Mol Hum Reprod. Sep. 2014;20(9):875-884. doi: 10.1093/molehr/gau048. Epub Jul. 4, 2014.

Zhao, et al. Methylated DNA immunoprecipitation and high-throughput sequencing (MeDIP-seq) using low amounts of genomic DNA. Cell Reprogram. Jun. 2014;16(3):175-184. doi: 10.1089/cell.2014.0002. Epub Apr. 28, 2014.

\* cited by examiner

Saturation Analysis

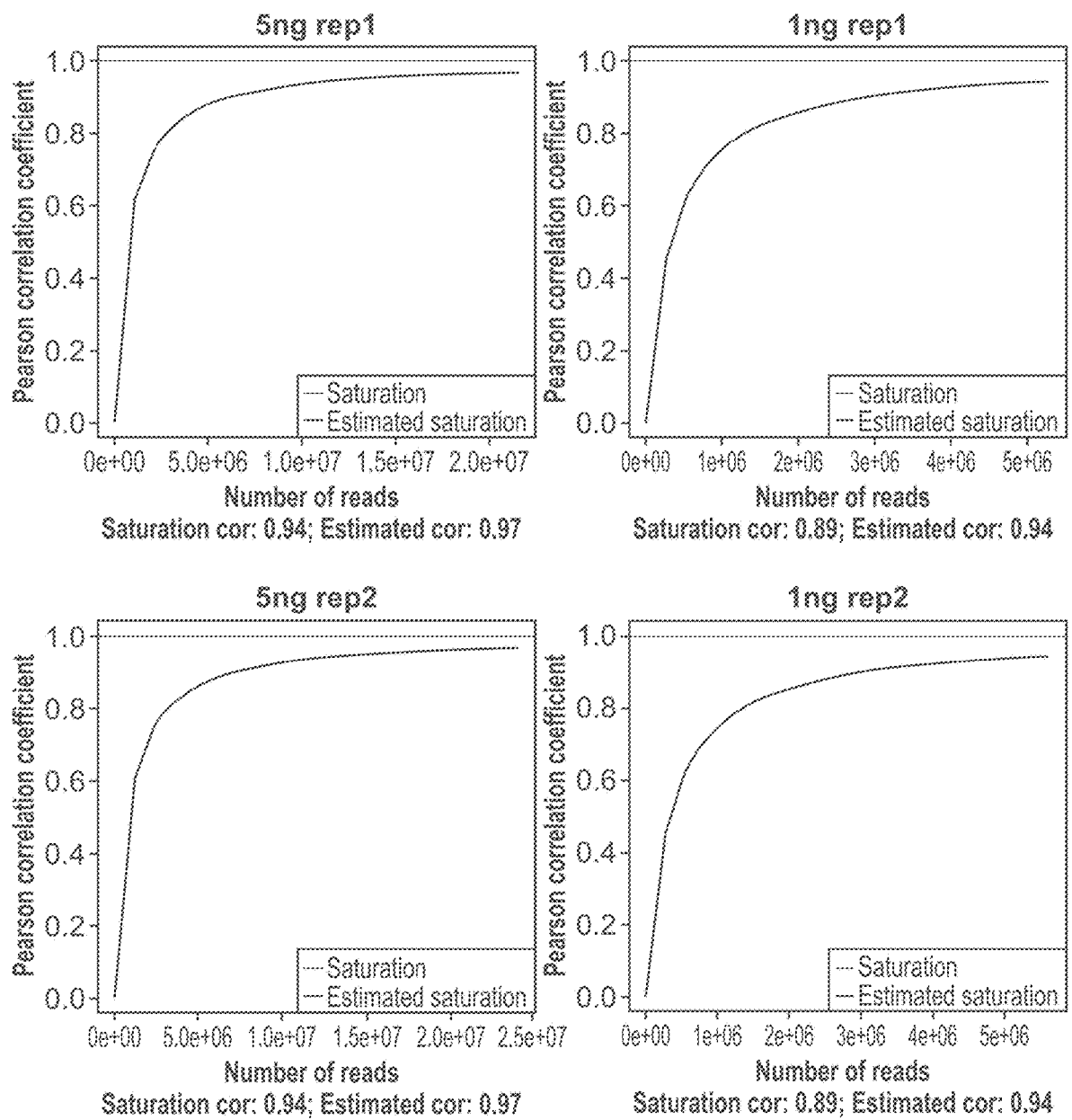
FIG. 3A (Cont. 1)
Saturation Analysis

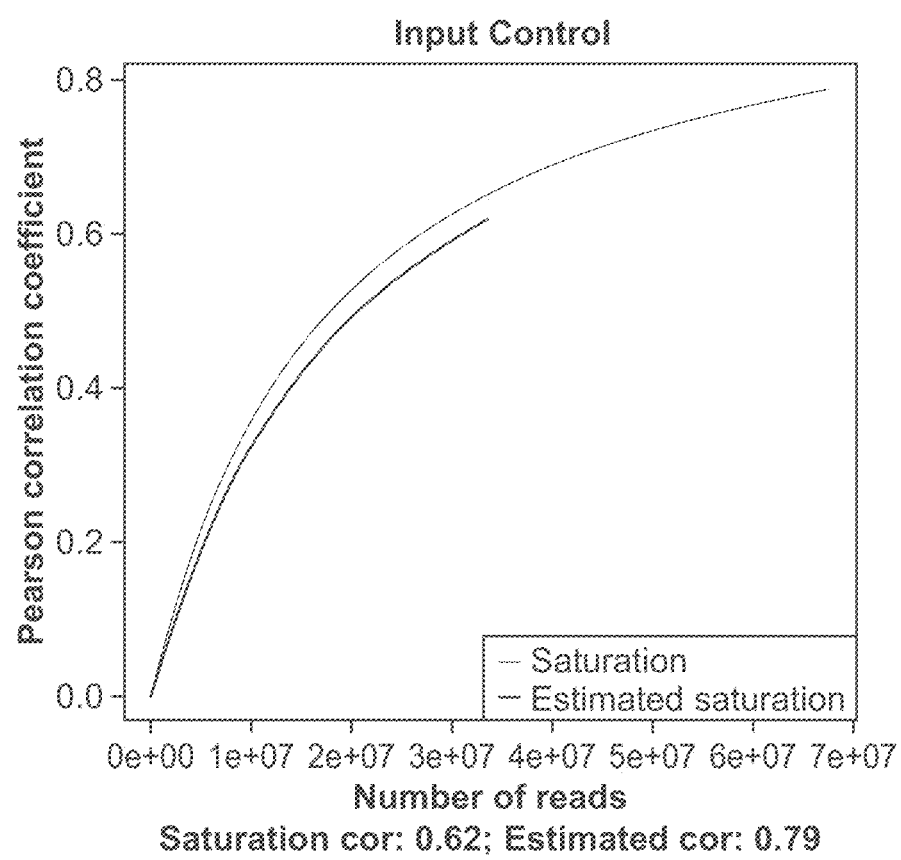
FIG. 3A (Cont. 2)
Saturation Analysis

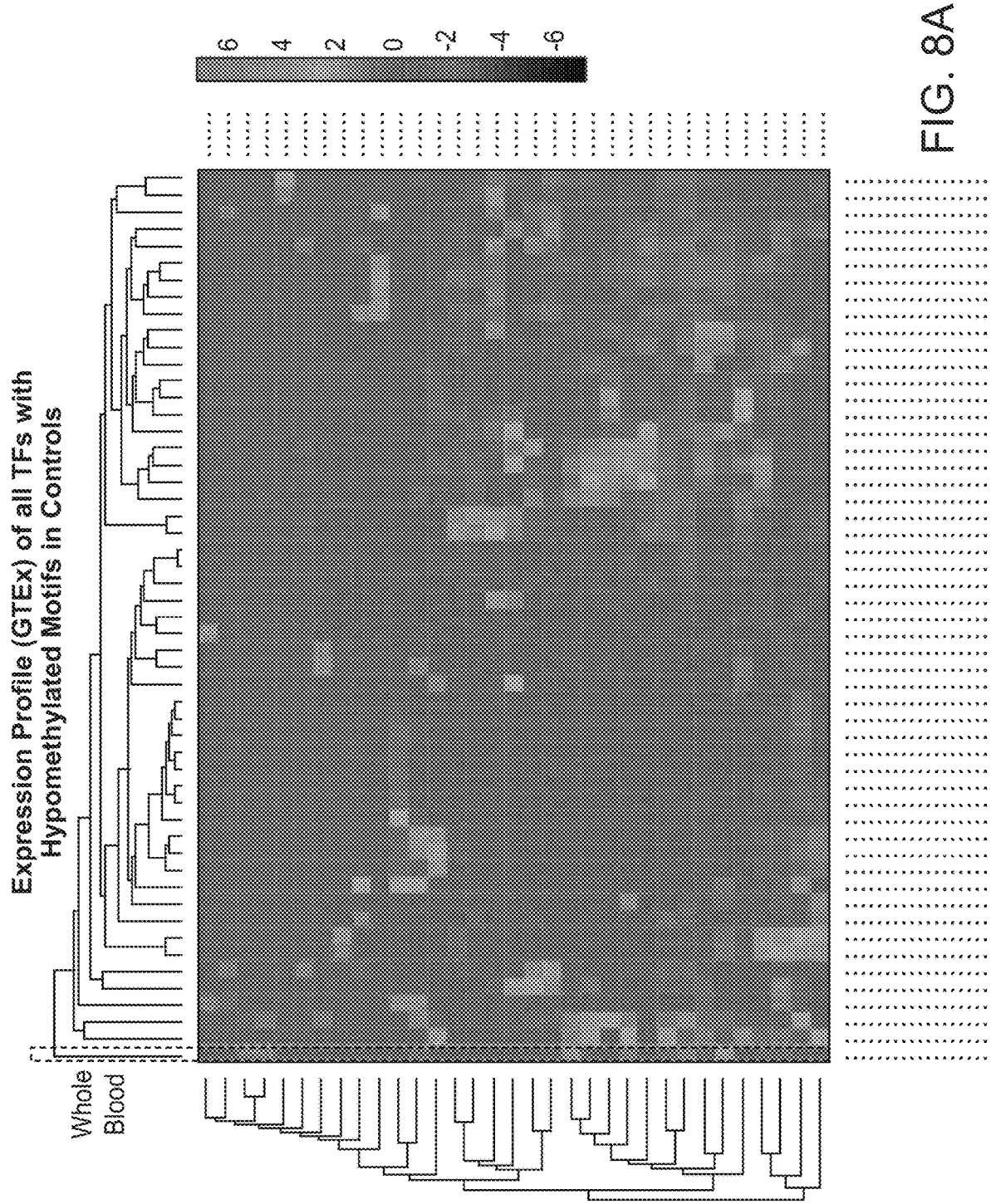

METHODS OF CAPTURING CELL-FREE METHYLATED DNA AND USES OF SAME

REFERENCE TO RELATED APPLICATION

This application is a continuation of U.S. application Ser. No. 17/353,756, filed Jun. 21, 2021, which is a continuation application of U.S. application Ser. No. 16/098,620, filed Nov. 2, 2018, now U.S. Pat. No. 11,078,475, issued on Aug. 3, 2021, which is a U.S. National Phase application of International Patent Application No. PCT/CA17/00108, filed May 3, 2017, which claims priority to U.S. Provisional Application No. 62/331,070, filed May 3, 2016, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Nov. 3, 2021, is named 59572-702.302_SL.txt and is 3,126 bytes in size.

FIELD OF THE INVENTION

The invention relates to the field of cell free DNA and, more specifically, to methods and uses of capturing cell-free methylated DNA.

BACKGROUND OF THE INVENTION

DNA methylation is a covalent modification of DNA and a stable gene regulatory mechanism that plays an important role in the chromatin architecture. In humans, DNA methylation primarily occurs at cytosine residues in CpG dinucleotides. Unlike other dinucleotides, CpGs are not evenly distributed across the genome but are instead concentrated in short CpG-rich DNA regions called CpG islands. DNA methylation can lead to gene repression by two main mechanisms: 1) recruiting methyl-binding domain proteins, which can in turn recruit histone deacetylases (HDACs) and 2) blocking the access to binding sites of transcription factors (TFs), such as c-MYC[1].

In general, the majority of the CpG sites in the genome are methylated, while most of the CpG islands remain unmethylated during normal development and in differentiated tissues[1]. Despite this fact, it is possible to identify tissue-specific patterns of DNA methylation in normal primary tissues[2]. Moreover, during malignant transformation, global DNA hypomethylation, and focal hypermethylation at CpG islands are frequently observed[1]. In fact, DNA methylation patterns have been used to stratify cancer patients into clinically relevant subgroups with prognostic value in glioblastoma[3], ependymomas[4], colorectal[5], breast[6,7], among many other cancer types.

Due to its stability and role in normal differentiation and diseases such as cancer, DNA methylation is a good biomarker that can be used to represent tumor characteristics and phenotypic states and therefore, has high potential for personalized medicine. Many sample types are suitable for DNA methylation mapping and for biomarker discovery including fresh and FFPE tumor tissue, blood cells, urine, saliva, stool, among others[8]. More recently, the use of circulating cell-free DNA (cfDNA) as a biomarker is gaining momentum, especially in situations where genomic distinctions exist, such as in cancer (somatic mutations)[9], transplants (donor versus recipient DNA)[10] and pregnancy (fetus versus mother DNA)[11,12]. Use of DNA methylation mapping of cfDNA as a biomarker could have a significant impact, as it could allow for the identification of the tissue-of-origin and stratify cancer patients in a minimally invasive fashion. Moreover, it could enable the use of cfDNA as a biomarker in situations where genomic distinctions do not exist, such as monitoring immune response, neurodegenerative diseases or myocardial infarction, where the epigenetic aberration can be detected in the cfDNA.

Furthermore, using genome-wide DNA methylation mapping of cfDNA could overcome a critical sensitivity problem in detecting circulating tumor DNA (ctDNA) in patients with early-stage cancer with no radiographic evidence of disease. Existing ctDNA detection methods are based on sequencing mutations and have limited sensitivity in part due to the limited number of recurrent mutations available to distinguish between tumor and normal circulating cfDNA[13,14]. On the other hand, genome-wide DNA methylation mapping leverages large numbers of epigenetic alterations that may be used to distinguish circulating tumor DNA (ctDNA) from normal circulating cell-free DNA (cfDNA). For example, some tumor types, such as ependymomas, can have extensive DNA methylation aberrations without any significant recurrent somatic mutations[4].

Moreover, pan-cancer data from The Cancer Genome Atlas (TCGA) shows large numbers of DMRs between tumor and normal tissues across virtually all tumor types[15]. Therefore, these findings highlighted that an assay that successfully recovered cancer-specific DNA methylation alterations from ctDNA could serve as a very sensitive tool to detect, classify, and monitor malignant disease with low sequencing-associated costs.

However, genome-wide mapping DNA methylation in cfDNA is extremely challenging due to the low amount of DNA available and to the fact that cfDNA is fragmented to less than 200 bp in length[16]. This makes it impossible to perform traditional MeDIP-seq, which needs at least 50-100 ng of DNA[17] or RRBS (Reduced Representation Bisulfite Sequencing), which needs non-fragmented DNA[18]. Another issue to mapping DNA methylation in cfDNA, is the low abundance of the DNA of interest within the normal cfDNA[19]. This makes it impractical to perform WGBS, as the cost of sequencing with enough depth to capture the low abundance DNA is prohibitive. On the other hand, a method that selectively enriches for CpG-rich features prone to methylation is likely to maximize the amount of useful information available per read, decrease the cost, and decrease the DNA losses.

SUMMARY OF INVENTION

According to one aspect, there is provided a method of capturing cell-free methylated DNA from a sample having less than 100 ng of cell-free DNA, comprising the steps of: subjecting the sample to library preparation to permit subsequent sequencing of the cell-free methylated DNA; adding a first amount of filler DNA to the sample, wherein at least a portion of the filler DNA is methylated; denaturing the sample; and capturing cell-free methylated DNA using a binder selective for methylated polynucleotides.

BRIEF DESCRIPTION OF FIGURES

Embodiments of the invention may best be understood by referring to the following description and accompanying drawings. In the drawings:

FIG. 1A shows Computer Simulation of the probability to detect at least one epimutation as a function of the concentration of ctDNA (columns), number of DMRs being investigated (rows), and the sequencing depth (x-axis). FIG. 1B shows Genome-wide Pearson correlation between DNA methylation signal for 1 to 100 ng of input DNA from HCT116 cell line fragmented to mimic plasma cfDNA. Each concentration has two biological replicates. FIG. 1C shows a DNA methylation profile obtained from cfMeDIP-seq from different concentrations of input DNA from HCT116 (Green Tracks) plus RRBS (Reduced Representation Bisulfite Sequencing) HCT116 data obtained from ENCODE (ENCSR000DFS) and WGBS (Whole-Genome Bisulfite Sequencing) HCT116 data obtained from GEO (GSM1465024). For the heatmap (RRBS track), yellow means methylated, blue means unmethylated and gray means no coverage. FIGS. 1D-1E show serial dilution of the CRC cell line HCT116 into the Multiple Myeloma (MM) cell line MM1.S. cfMeDIP-seq was performed in pure HCT116 DNA (100% CRC), pure MM1.S DNA (100% MM) and 10%, 1%, 0.1%, 0.01%, and 0.001% CRC DNA diluted into MM DNA. All DNA was fragmented to mimic plasma cfDNA. We observed an almost perfect linear correlation ($r^2=0.99$, $p<0.0001$) between the observed versus expected (D) numbers of DMRs and (E) the DNA methylation signal (in RPKM) within those DMRs. FIG. 1F shows in the same dilution series, known somatic mutations are only detectable at $\frac{1}{100}$ allele fraction by ultra-deep (>10,000×) targeted sequencing, above the background sequencer and polymerase error rate. Shown are the fractions of reads containing each base or an insertion/deletion at the site of each mutation in the CRC cell line. FIG. 1G shows frequency of ctDNA (human) as a percentage of total cfDNA (human+mice) in the plasma of mice harboring patient-derived xenograft (PDX) from two colorectal cancer patients.

FIG. 3A shows the results of the saturation analysis from the Bioconductor package MEDIPS analyzing cfMeDIP-seq data from each replicate for each input concentration from the HCT116 DNA fragmented to mimic plasma cfDNA. FIG. 3B shows the protocol was tested in two replicates of four starting DNA concentrations (100, 10, 5, and 1 ng) of HCT116 cell line. Specificity of the reaction was calculated using methylated and unmethylated spiked-in A. thaliana DNA. Fold enrichment ratio was calculated using genomic regions of the fragmented HCT116 DNA (Primers for methylated testis-specific H2B, TSH2B0 and unmethylated human DNA region (GAPDH promoter)). The horizontal dotted line indicates a fold-enrichment ratio threshold of 25. Error bars represent±1 s. e. m. FIG. 3C shows CpG Enrichment Scores of the sequenced samples show a robust enrichment of CpGs within the genomic regions from the immunoprecipitated samples compared to the input control. The CpG Enrichment Score was obtained by dividing the relative frequency of CpGs of the regions by the relative frequency of CpGs of the human genome. Error bars represent±1 s. e. m.

FIG. 4A shows schematic representation of the CRC DNA (HCT116) dilution into MM DNA (MM1.S). FIG. 4B shows specificity of reaction for each dilution was calculated using methylated and unmethylated spiked-in A. thaliana DNA. C) CpG Enrichment Scores of the sequenced samples show a strong enrichment of CpGs within the genomic regions from the immunoprecipitated samples. The CpG Enrichment Score was obtained by dividing the relative frequency of CpGs of the regions by the relative frequency of CpGs in the human genome. FIG. 4D shows the figure shows the results of the saturation analysis from each dilution point.

FIG. 5A shows experimental design. FIG. 5B shows volcano plot for circulating cfDNA from pancreatic cancer (cases, n=24) versus healthy donors (controls, n=24) using cfMeDIP-seq. Red dots indicate the windows that reached significance after correction for multiple tests. FIG. 5C shows heatmap of the 38,085 DMRs identified in the plasma DNA from healthy donors and pancreatic cancer patients. Hierarchical clustering method: Ward. FIG. 5D shows permutation analysis to estimate the frequency of expected versus the observed overlap between the DMRs identified in the plasma (cases versus controls) and the cancer-specific DMCs identified in the primary tumor tissue (primary tumor versus normal tissue). The box-plots represent the null distribution for the overlap. The diamonds represent the experimentally observed number of overlap between primary tumor tissue and DNA methylation from circulating cfDNA. Red diamonds mean the observed number of overlaps is significantly more than expected by chance. Green diamonds mean that the observed number of overlaps is significantly less than expected by chance and blue diamonds are non-significant. We calculated four possible overlaps: Hypermethylated in the primary tumor tissue and hypermethylated in the circulating cfDNA (Enriched, P-value: $6.4 \times 10^{-22}$); Hypermethylated in the tumor tissue and hypomethylated in the circulating cfDNA (Depleted, P-value: $9.43 \times 10^{-17}$); Hypomethylated in the tumor tissue and hypomethylated in the circulating cfDNA (Enriched, P-value: $1.88 \times 10^{-283}$); Hypomethylated in the tumor tissue and hypermethylated in the circulating cfDNA (P-value: 0.105). FIG. 5E shows permutation analysis to estimate the frequency of expected versus the observed overlap between the DMRs identified in the plasma (cases versus controls) and the cancer-specific DMCs identified in the primary tumor tissue (primary tumor versus normal PBMCs).

FIGS. 6A-B specificity of reaction for each case (A) and each control (B) sample was calculated using methylated and unmethylated spiked-in A. thaliana DNA. Fold enrichment ratio was not calculated due to the very limited amount of DNA available. FIGS. 6C-D shows CpG Enrichment Scores of the sequenced samples show a strong enrichment of CpGs within the genomic regions from the immunoprecipitated samples.

Hypomethylated regions are shown on a negative scale. Y-axis shows the log 10 q values for the plasma cfDNA methylation from pancreatic adenocarcinoma patients versus healthy donors from the cfMeDIP-seq data. Blue dots are significant in both Red line shows the trend line.

FIGS. 8A-8E show circulating cfDNA methylation profile can be used to identify transcription factors (TFs) footprints and infer active transcriptional networks in the tissue-of-origin. FIG. 8A shows expression profile of all TFs (n=33) whose motifs were enriched (using the software HOMER[20]) in the regions hypomethylated in the cfDNA from healthy donors (hypomethylated footprints in controls) across multiple human tissues. The expression data was obtained from the Genotype-Tissue Expression (GTEx) project[21]. Several TFs preferentially expressed in the hematopoietic system were identified (PU.1, Fli1, STAT5B, KLF1). FIG. 8B shows expression profile of all TFs with hypomethylated motifs in controls (n=33) versus the expression profile of 1,000 random sets of 33 TFs in whole blood (GTEx data). FIG. 8C shows expression profile of all TFs (n=85) whose motifs were enriched in the regions hypomethylated in the cfDNA from pancreatic adenocarcinoma patients (hypomethylated footprints in cases). Several pancreas-specific or pancreatic cancer-associated TFs were identified. Moreover, hallmark TFs that drive molecular subtypes of pancreatic cancer were also identified. FIG. 8D shows expression profile of all TFs with hypomethylated motifs in cases (n=85) versus the expression profile of 1,000 random sets of 85 TFs in normal pancreas (GTEx data). FIG. 8E shows expression profile of all TFs with hypomethylated motifs in cases (n=85) versus the expression profile of 1,000 random sets of 85 TFs in pancreatic adenocarcinoma tissue (TCGA data).

DETAILED DESCRIPTION

Figure 1A:
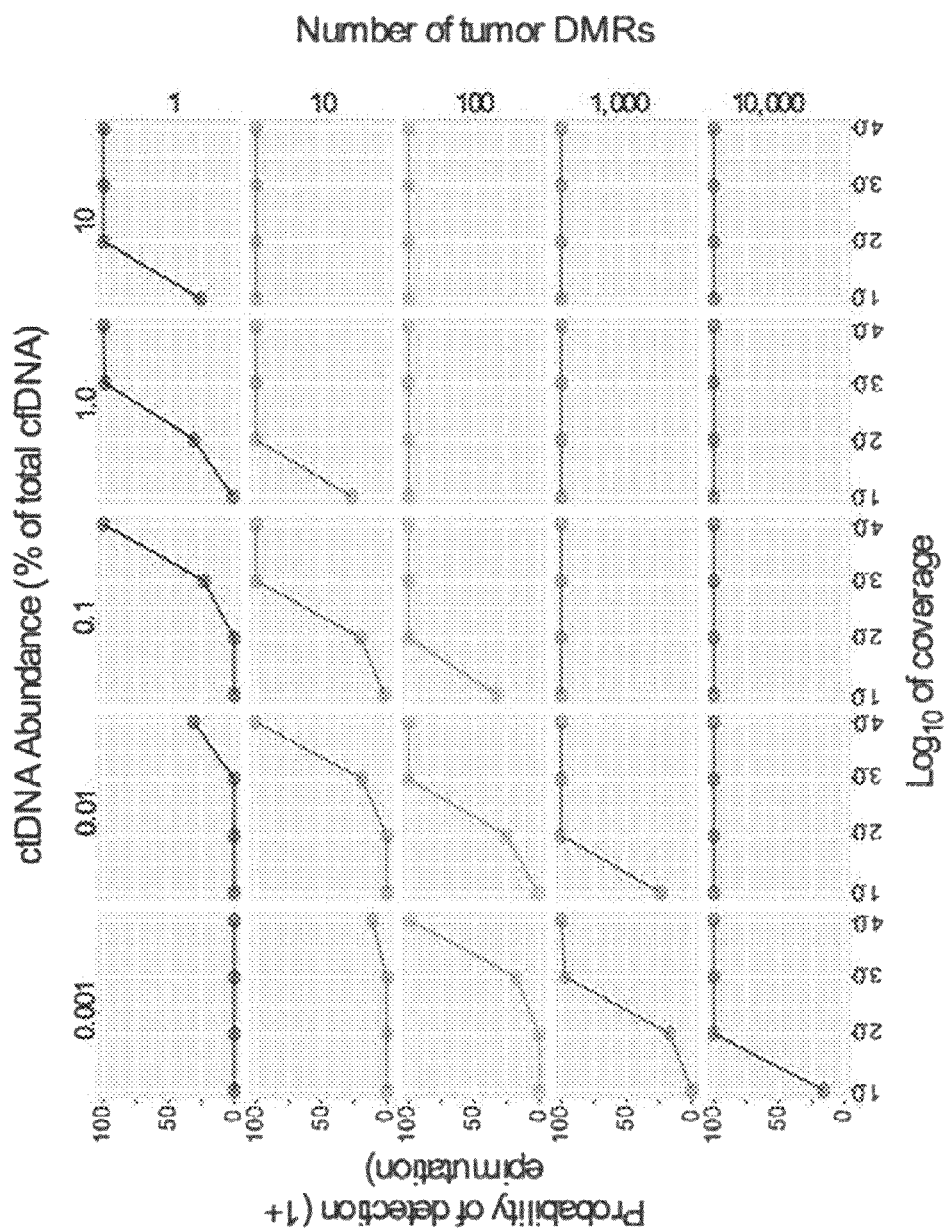
FIGS. 1A-1G shows the methylome analysis of cfDNA is a highly sensitive approach to enrich and detect ctDNA in low amounts of input DNA.

We bioinformatically simulated mixtures with different proportions of ctDNA, from 0.001% to 10% (FIG. 1A, column facets). We also simulated scenarios where the ctDNA had 1, 10, 100, 1000, or 10000 DMRs (Differentially Methylated Regions) as compared to normal cfDNA (FIG. 1A, row facets). Reads were then sampled at varying sequencing depths at each locus (10×, 100×, 1000×, and 10000×) (FIG. 1A, x-axis). We found an increasing probability of detecting of at least 1 cancer-specific event (FIG. 1A) as the number of DMRs increased, even at low abundance of cancer ctDNA and shallow coverage.

Figure 2:
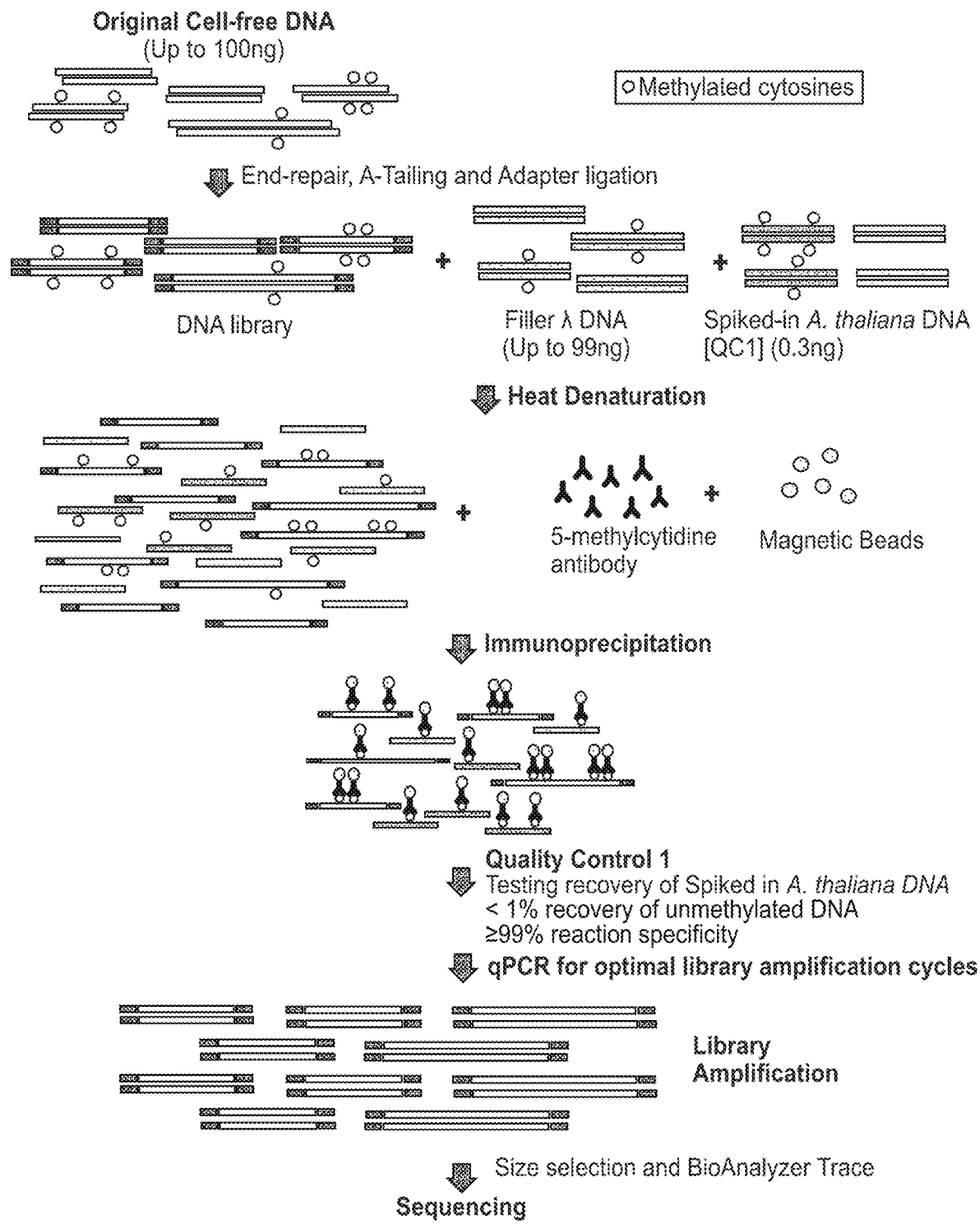
FIG. 2 shows the schematic representation of the cfMeDIP-seq protocol.
Figure 9:
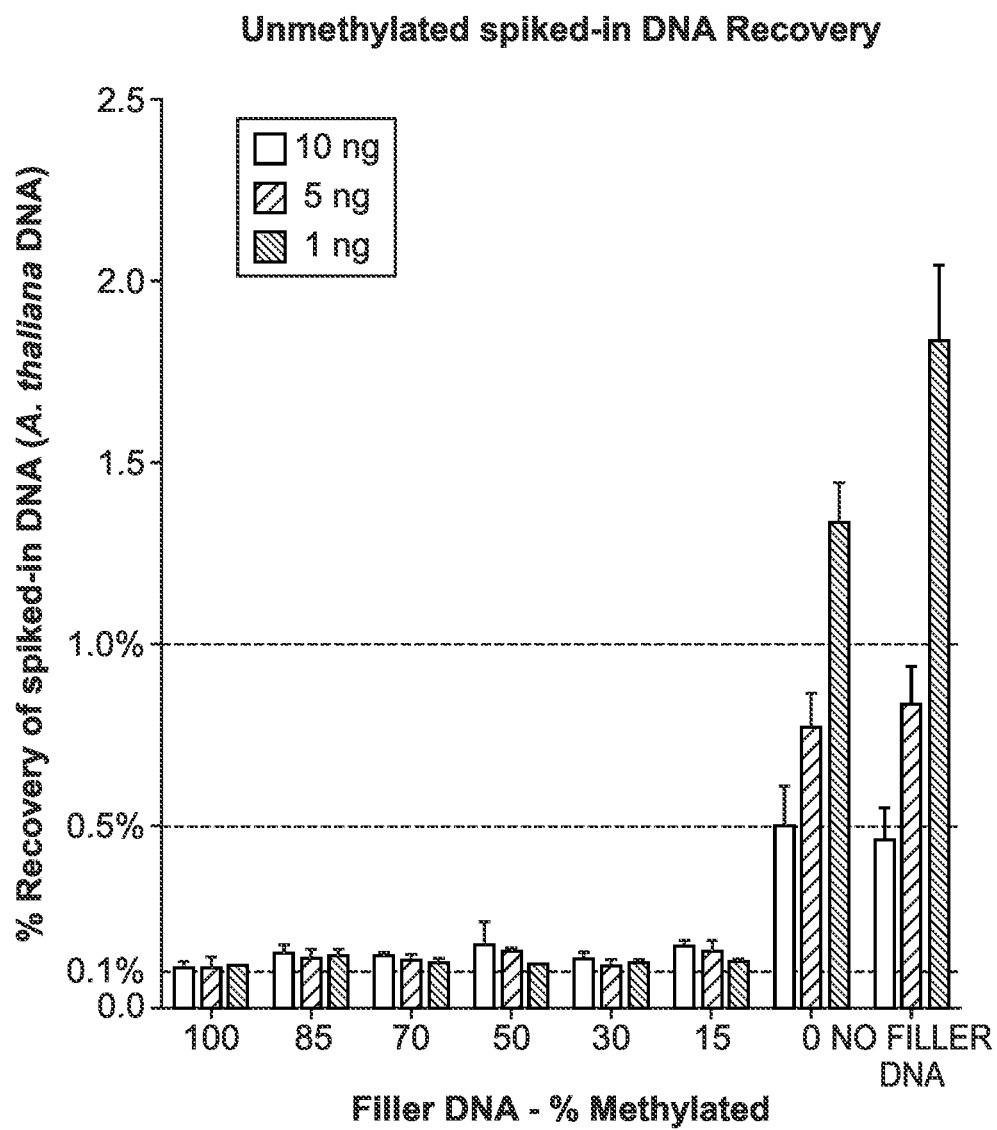
FIG. 9 shows % Recovery of spiked-in unmethylated *A. thaliana* DNA after cfMeDIP-seq using 10 ng, 5 ng and 1 ng of starting cancer cell-free DNA amounts (n=3), combined with 90 ng, 95 ng and 99 ng of filler DNA respectively or no filler DNA, prior to immunoprecipitation. The filler DNA used varied in the composition of % artificially methylated to % unmethylated lambda DNA present to increase final amount prior to immunoprecipitation to Wang. The % recovery of spiked-in unmethylated DNA desired is <1.0%, with lower recovery resulting in higher % specificity of reaction.
Figure 10:
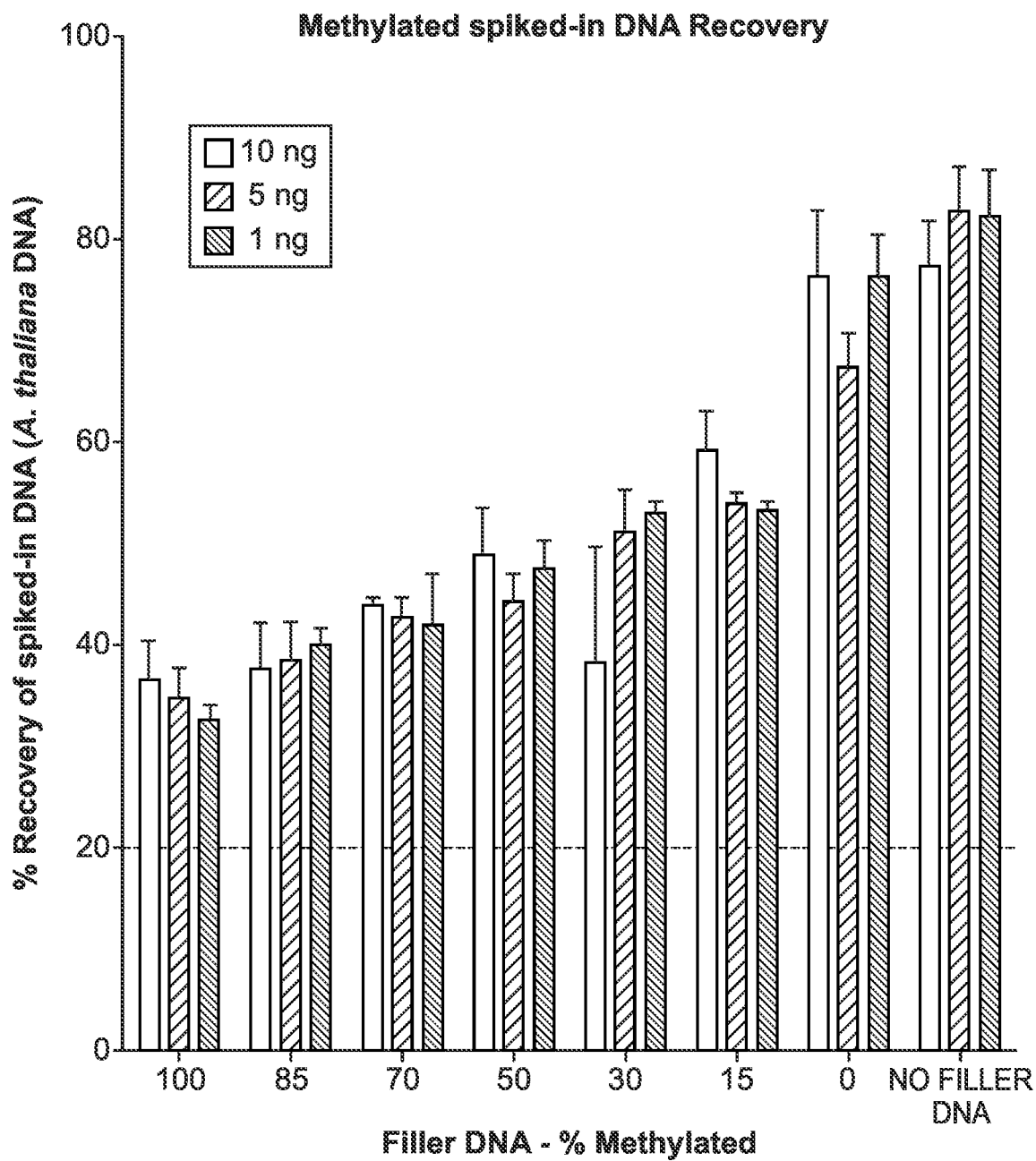
FIG. 10 shows % Recovery of spiked-in methylated *A. thaliana* DNA after cfMeDIP-seq using long, 5 ng and 1 ng of starting cancer cell-free DNA amounts (n=3), combined with 90 ng, 95 ng and 99 ng of filler DNA respectively or no filer DNA, prior to immunoprecipitation. The filler DNA used varied in the composition of % artificially methylated to % unmethylated lambda DNA present to increase final amount prior to immunoprecipitation to 100 ng. Minimum % recovery of spiked-in methylated DNA desired is 20%.

To overcome these challenges, we have developed a new method called cfMeDIP-seq (cell-free Methylated DNA Immunoprecipitation and high-throughput sequencing) to perform genome-wide DNA methylation mapping using cell-free DNA. The cfMeDIP-seq method described here was developed through the modification of an existing low input MeDIP-seq protocol[17] that is robust down to 100 ng of input DNA. However, the majority of plasma samples yield much less than 100 ng of DNA. To overcome this challenge, we added exogenous λ DNA (filler DNA) to the adapter-ligated cfDNA library in order to artificially inflate the amount of starting DNA to 100 ng (FIG. 2). This minimizes the amount of non-specific binding by the antibody and also minimizes the amount of DNA lost due to binding to plasticware. The filler DNA consisted of amplicons similar in size to an adapter-ligated cfDNA library and was composed of unmethylated and in vitro methylated DNA at different methylation levels (FIG. 9 and FIG. 10). The addition of this filler DNA also serves a practical use, as different patients will yield different amounts of cfDNA, allowing for the normalization of input DNA amount to 100 ng. This ensures that the downstream protocol remains exactly the same for all samples regardless of the amount of available cfDNA.

According to one aspect, there is provided a method of capturing cell-free methylated DNA from a sample having less than 100 ng of cell-free DNA, comprising the steps of:
 a. subjecting the sample to library preparation to permit subsequent sequencing of the cell-free methylated DNA;
 b. adding a first amount of filler DNA to the sample, wherein at least a portion of the filler DNA is methylated;
 c. denaturing the sample; and
 d. capturing cell-free methylated DNA using a binder selective for methylated polynucleotides.

In some embodiments, this method further comprises the step of amplifying and subsequently sequencing the captured cell-free methylated DNA.

Various sequencing techniques are known to the person skilled in the art, such as polymerase chain reaction (PCR) followed by Sanger sequencing. Also available are next-generation sequencing (NGS) techniques, also known as high-throughput sequencing, which includes various sequencing technologies including: Illumine (Solexa) sequencing, Roche 454 sequencing, Ion torrent: Proton/PGM sequencing, SOLiD sequencing. NGS allow for the sequencing of DNA and RNA much more quickly and cheaply than the previously used Sanger sequencing. In some embodiments, said sequencing is optimized for short read sequencing.

Cell-free methylated DNA is DNA that is circulating freely in the blood stream, and are methylated at various known regions of the DNA. Samples, for example, plasma samples can be taken to analyze cell-free methylated DNA.

As used herein, "library preparation" includes list end-repair, A-tailing, adapter ligation, or any other preparation performed on the cell free DNA to permit subsequent sequencing of DNA.

As used herein, "filler DNA" can be noncoding DNA or it can consist of amplicons.

DNA samples may be denatured, for example, using sufficient heat.

In some embodiments, samples have less than 50 ng of cell-free DNA.

In some embodiments, the first amount of filler DNA comprises about 10%, 20%, 30%, 40%, 50%, 60%, 70%, 80%, 90%, or 100% methylated filler DNA. In preferred embodiments, the first amount of filler DNA comprises about 50% methylated filler DNA.

In some embodiments, the first amount of filler DNA is from 20 ng to 100 ng. In preferred embodiments, 30 ng to 100 ng of filler DNA. In more preferred embodiments 50 ng to 100 ng of filler DNA. When the cell-free DNA from the sample and the first amount of filler DNA are combined together, there comprises at least 50 ng of total DNA, and preferably at least 100 ng of total DNA.

In some embodiments, the filler DNA is 50 bp to 800 bp long. In preferred embodiments, 100 bp to 600 bp long; and in more preferred embodiments 200 bp to 600 bp long.

The filler DNA is double stranded. For example, the filler DNA can be junk DNA. The filler DNA may also be endogenous or exogenous DNA. For example, the filler DNA is non-human DNA, and in preferred embodiments, λ DNA. As used herein, "λ DNA" refers to Enterobacteria phage λ DNA. In some embodiments, the filler DNA has no alignment to human DNA.

In some embodiments, the binder is a protein comprising a Methyl-CpG-binding domain. One such exemplary protein is MBD2 protein. As used herein, "Methyl-CpG-binding domain (MBD)" refers to certain domains of proteins and enzymes that is approximately 70 residues long and binds to DNA that contains one or more symmetrically methylated CpGs. The MBD of MeCP2, MBD1, MBD2, MBD4 and BAZ2 mediates binding to DNA, and in cases of MeCP2, MBD1 and MBD2, preferentially to methylated CpG. Human proteins MECP2, MBD1, MBD2, MBD3, and MBD4 comprise a family of nuclear proteins related by the presence in each of a methyl-CpG-binding domain (MBD). Each of these proteins, with the exception of MBD3, is capable of binding specifically to methylated DNA.

In other embodiments, the binder is an antibody and capturing cell-free methylated DNA comprises immunoprecipitating the cell-free methylated DNA using the antibody. As used herein, "immunoprecipitation" refers a technique of precipitating an antigen (such as polypeptides and nucleotides) out of solution using an antibody that specifically binds to that particular antigen. This process can be used to isolate and concentrate a particular protein or DNA from a sample and requires that the antibody be coupled to a solid substrate at some point in the procedure. The solid substrate includes for examples beads, such as magnetic beads. Other types of beads and solid substrates are known in the art.

One exemplary antibody is 5-MeC antibody. For the immunoprecipitation procedure, in some embodiments at least 0.05 μg of the antibody is added to the sample; while in more preferred embodiments at least 0.16 μg of the antibody is added to the sample. To confirm the immunoprecipitation reaction, in some embodiments the method described herein further comprises the step of adding a second amount of control DNA to the sample after step (b).

Another exemplary antibody is or 5-hydroxymethyl cytosine antibody.

In other embodiments, the method described herein further comprises the step of adding a second amount of control DNA to the sample after step (b) for confirming the capture of cell-free methylated DNA.

As used herein, the "control" may comprise both positive and negative control, or at least a positive control.

According to a further aspect, there is provided use of the methods described herein for measuring a DNA methylation profile within the sample.

According to a further aspect, there is provided use of the methods described herein to identify the presence of cell free DNA from cancer cells within the sample by correlating the profile with known methylation profiles of tumour tissue.

According to a further aspect, there is provided use of the DNA methylation profile as described herein for identifying tissue-of-origin of the cell-free DNA within the sample by correlating the profile with known methylation profiles of specific tissues.

In some embodiments, the use further comprising the use of described herein for identifying tissue of origin of the cancer cells within the cell-free DNA within the sample.

According to a further aspect, there is provided the use described herein for monitoring immune therapy.

According to a further aspect, there is provided the use described herein for the diagnosis of autoimmune conditions.

According to a further aspect, there is provided the use described herein for determining cell turnover in a subject from which the sample is taken.

The following examples are illustrative of various aspects of the invention, and do not limit the broad aspects of the invention as disclosed herein.

EXAMPLES

Methods

Donor Recruitment and Sample Acquisition

Pancreatic adenocarcinoma (PDAC) patient samples were obtained from the University Health Network BioBank; healthy controls were recruited through the Family Medicine Centre at Mount Sinai Hospital (MSH) in Toronto, Canada. All samples collected with patient consent, were obtained with institutional approval from the Research Ethics Board, from University Health Network and Mount Sinai Hospital in Toronto, Canada.

Specimen Processing—Purified Tumor and Normal Cells

For primary PDAC samples, specimens were processed immediately following resection and representative sections were used to confirm the diagnosis. Laser capture microdissection (LCM) of freshly liquid nitrogen-frozen tissue samples was performed on a Leica LMD 7000 instrument, Briefly, frozen tissue maintained in vapor-phase liquid nitrogen was embedded in OCT cutting medium and sectioned in a cryotome into 8-μm thick sections. Sections were mounted on PEN membrane slides (Leica) and lightly stained with hematoxylin to facilitate microscopic identification of tumor areas. LCM was performed on the same day when sections were cut to minimize nucleic acid degradation.

Microdissected tumor cells were collected by gravity into the caps of sterile, RNAse-free microcentrifuge tubes. Approximately 150,000-200,000 tumor cells were collected for DNA sample and stored at −80° C. until further processing. LCM typically took 1-2 days per case to collect sufficient amounts of purified tumor cells. Qiagen Cell Lysis Buffer was used to extract genomic DNA. Matched normal, histologically reviewed reference tissue was collected for each patient from frozen duodenal or gastric mucosa by scraping unstained frozen sections on glass slides into the appropriate DNA extraction buffer.

Specimen Processing—cfDNA

EDTA and ACD plasma samples were obtained from the BioBank and from the Family Medicine Centre at Mount Sinai Hospital (MSH) in Toronto, Canada. All samples were either stored at −80° C. or in vapour phase liquid nitrogen until use. Cell-free DNA was extracted from 0.5-3.5 ml of plasma using the QIAamp Circulating Nucleic Acid Kit (Qiagen). The extracted DNA was quantified through Qubit prior to use.

Specimen Processing—PDX cfDNA

Human colorectal tumor tissue obtained with patient consent from the University Health Network Biobank as approved by the Research Ethics Board at University Health Network, was digested to single cells using collagenase A. Single cells were subcutaneously injected into 4-6 week old NOD/SCID male mouse. Mice were euthanized by CO2 inhalation prior to blood collection by cardiac puncture and stored in EDTA tubes. From the collected blood samples, the plasma was isolated and stored at −80 C. Cell-free DNA was extracted from 0.3-0.7 ml of plasma using the QIAamp Circulating Nucleic Acid Kit (Qiagen). All animal work was carried out in compliance with the ethical regulations approved by the Animal Care Committee at University Health Network.

RRBS

Genomic DNA extracted from the LCM-enriched tumor and normal samples coming from the same patients, for who the cell-free DNA had been obtained, was subjected to RRBS following the protocol from Gu et al., 2011[18] with minor modifications. Briefly, 10 ng of genomic DNA, determined through Qubit, was digested using restriction enzyme MspI, then subjected to end-repair, A-tailing and adapter ligation to Illumina TruSeq methylated adapters. The prepared libraries were then subjected to bisulfite conversion using the Zymo EZ DNA methylation kit following manufacturer's protocol, followed by gel size selection for fragments of 160 bp-300 bp. The optimal number of cycles to amplify each purified library was determined through the use of qPCR, after which the samples were amplified using the KAPA HiFi Uracil+ Mastermix (Kapa Biosystems) and purified with AMPure beads (Beckman Coulter). The final libraries were submitted for BioAnalyzer analysis prior to sequencing at the UHN Princess Margaret Genomic Centre in an Illumina HiSeq 2000.

Preparation of Exogenous Enterobacteria Phage λ PCR Product

Enterobacteria phage λ DNA (ThermoFischer Scientific) was amplified using the primers indicated in Table 1, generating 6 different PCR amplicons products. The PCR reaction was carried out using KAPA HiFi Hotstart ReadyMix with the following condition: activation of enzyme at 95° C. for 3 min, 30 cycles of 98° C. for 20 sec, 60° C. for 15 sec, 72° C. for 30 sec and a final extension at 72° C. for 1 min. The PCR amplicons were purified with QIAQuick PCR purification kit (Qiagen) and ran on a gel to verify size and amplification. Amplicons for 1 CpG, 5 CpG, 10 CpG, 15 CpG and 20 CpGL were methylated using CpG Methyltransferase (M.SssI) (ThermoFischer Scientific) and purified with the QIAQuick PCR purification kit. Methylation of the PCR amplicons was tested using restriction enzyme HpyCH4IV (New England Biolabs Canada) and ran on a gel to ensure its methylation. The DNA concentration of the unmethylated (20 CpGS) and methylated (1 CpG, 5 CpG, 10 CpG, 15 CpG, 20 CpGL) amplicons was measured using picogreen prior to pooling with 50% of methylated and 50% unmethylated A PCR product.

cfMeDIP-Seq

A schematic representation of the cfMeDIP-seq protocol is shown in FIG. 2. Prior to cfMeDIP, the DNA samples were subjected to library preparation using the Kapa Hyper Prep Kit (Kapa Biosystems). The manufacturer protocol was followed with some modifications. Briefly, the DNA of interest was added to 0.2 mL PCR tube and subjected to end-repair and A-Tailing. Adapter ligation was followed using NEBNext adapter (from the NEBNext Multiplex Oligos for Illumina kit, New England Biolabs) at a final concentration of 0.181 μM, incubated at 20° C. for 20 mins and purified with AMPure XP beads. The eluted library was digested using the USER enzyme (New England Biolabs Canada) followed by purification with Qiagen MinElute PCR Purification Kit prior to MeDIP.

The prepared libraries were combined with the pooled methylated/unmethylated λ PCR product to a final DNA amount of 100 ng and subjected to MeDIP using the protocol from Taiwo et al. 2012[17] with some modifications. For MeDIP, the Diagenode MagMeDIP kit (Cat #C02010021) was used following the manufacturer's protocol with some modifications. After the addition of 0.3 ng of the control methylated and 0.3 ng of the control unmethylated *A. thaliana* DNA, the filler DNA (to complete the total amount of DNA [cfDNA+Filler+Controls] to 100 ng) and the buffers to the PCR tubes containing the adapter ligated DNA, the samples were heated to 95° C. for 10 mins, then immediately placed into an ice water bath for 10 mins. Each sample was partitioned into two 0.2 mL PCR tubes: one for the 10% input control and the other one for the sample to be subjected to immunoprecipitation. The included 5-mC monoclonal antibody 33D3 (Cat #C15200081) from the MagMeDIP kit was diluted 1:15 prior to generating the diluted antibody mix and added to the sample. Washed magnetic beads (following manufacturer instructions) were also added prior to incubation at 4° C. for 17 hours. The samples were purified using the Diagenode iPure Kit and eluted in 50 µl of Buffer C. The success of the reaction (QC1) was validated through qPCR to detect the presence of the spiked-in *A. thaliana* DNA, ensuring a % recovery of unmethylated spiked-in DNA<1% and the specificity of the reaction>99% (as calculated by 1-[recovery of spiked-in unmethylated control DNA over recovery of spiked-in methylated control DNA]), prior to proceeding to the next step. The optimal number of cycles to amplify each library was determined through the use of qPCR, after which the samples were amplified using the KAPA HiFi Hotstart Mastermix and the NEBNext multiplex oligos added to a final concentration of 0.3 µM. The PCR settings used to amplify the libraries were as follows: activation at 95° C. for 3 min, followed by predetermined cycles of 98° C. for 20 sec, 65° C. for 15 sec and 72° C. for 30 sec and a final extension of 72° C. for 1 min. The amplified libraries were purified using MinElute PCR purification column and then gel size selected with 3% Nusieve GTG agarose gel to remove any adapter dimers. Prior to submission for sequencing, the fold enrichment of a methylated human DNA region (testis-specific H2B, TSH2B) and an unmethylated human DNA region (GAPDH promoter) was determined for the MeDIP-seq and cfMeDIP-seq libraries generated from the HCT116 cell line DNA sheared to mimic cell free DNA (Cell line obtained from ATCC, mycoplasma free). The final libraries were submitted for BioAnalyzer analysis prior to sequencing at the UHN Princess Margaret Genomic Centre on an Illumina HiSeq 2000.

Differing % of Methylation in the Filler DNA cfMeDIP-seq was performed using different % of methylated to unmethylated lambda DNA in the filler component of the protocol as follows:

Using filler (lambda) DNA to increase final amount of DNA to 100 ng prior to immunoprecipitation, with the starting amounts of cell-free DNA ranging from 10 ng, 5 ng and 1 ng

| % Methylated Filler | % Unmethylated Filler |
| --- | --- |
| 100 | 0 |
| 85 | 15 |
| 70 | 30 |
| 50 | 50 |
| 30 | 70 |
| 15 | 85 |
| 0 | 100 |

No Filler DNA used - as is only 10 ng, 5 ng or 1 ng of starting DNA prior to immunoprecipitation As shown in FIGS. 9 and 10, the filler DNA (lambda DNA) used to increase the final amounts prior to immunoprecipitation to 100 ng, should preferably have some artificially methylated DNA in its composition (from 100%-15%) in order to have the minimal recovery unmethylated DNA (FIG. 9), while still getting a good yield in terms of recovery of methylated DNA (FIG. 10). In the samples where we have 100% unmethylated filler DNA or no filler DNA present, although there is really higher recovery of methylated DNA, we also have high % recovery of unmethylated DNA. This shows that the additional methylated DNA in the filler DNA helps to occupy the excess antibody present in the reaction, minimizing the amount of unspecific binding to unmethylated DNA found in the sample. Given that optimizing antibody amounts is not very economical or even feasible in cases where different cell-free DNA samples are used, as it is unknown how much methylated DNA is present throughout the sample and this could differ drastically sample to sample, this filler DNA helps normalize the different starting amounts and allow for different cell-free DNA samples to be processed the same way (i.e use same amount of antibody), while still recovering good methylation data from it.

Ultra-Deep Targeted Sequencing for Point Mutation Detection

We used the QIAgen Circulating Nucleic Acid kit to isolate cell-free DNA from ~20 mL of plasma (4-5×10 mL EDTA blood tubes) from patients with matched tumor tissue molecular profiling data generated prior to enrolment in early phase clinical trials at the Princess Margaret Cancer Centre. DNA was extracted from cell lines (dilution of CRC and MM cell lines) using the PureGene Gentra kit, fragmented to ~180 bp using a Covaris sonicator, and larger size fragments excluded using Ampure beads to mimic the fragment size of cell-free DNA. DNA sequencing libraries were constructed from 83 ng of fragmented DNA using the KAPA Hyper Prep Kit (Kapa Biosystems, Wilmington, Mass.) utilizing NEXTflex-96 DNA Barcode adapters (Bio Scientific, Austin, Tex.) adapters. To isolate DNA fragments containing known mutations, we designed biotinylated DNA capture probes (xGen Lockdown Custom Probes Mini Pool, Integrated DNA Technologies, Coralville, Iowa) targeting mutation hotspots from 48 genes tested by the clinical laboratory using the Illumina TruSeq Amplicon Cancer Panel. The barcoded libraries were pooled and then applied the custom hybrid capture library following manufacturer's instructions (IDT xGEN Lockdown protocol version 2.1). These fragments were sequenced to >10,000× read coverage using an Illumina HiSeq 2000 instrument. Resulting reads were aligned using bwa-mem and mutations detected using samtools and muTect version 1.1.4.

Modelling Relationships Between Number of Tumor-Specific Features and Probability of Detection by Sequencing Depth We created 145,000 simulated genomes, with the proportion of cancer-specific methylated DMRs set to 0.001%, 0.01%, 0.1%, 1%, and 10% and consisting of 1, 10, 100, 1000 and 10000 independent DMRs respectively. We sampled 14,500 diploid genomes (representing 100 ng of DNA) from these original mixtures and further sampled 10, 100, 1000, and 10000 reads per locus to represent sequencing coverage at those depths. This process was repeated 100 times for each combination of coverage, abundance, and number of features. We estimated the frequency of successful detection of at least 1 DMR for each combination of parameters and plotted probability curves (FIG. 1A) to visually evaluate the influence of the number of features on the probability of successful detection conditional on sequencing depths.

Figure 5A:
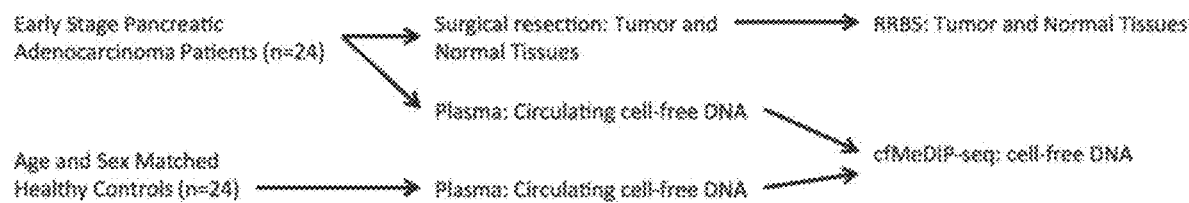
FIGS. 5A-5E show that the cfMeDIP-seq method can identify thousands of differentially methylated regions on circulating cfDNA obtained from pancreatic adenocarcinoma patients.
Figure 5B:
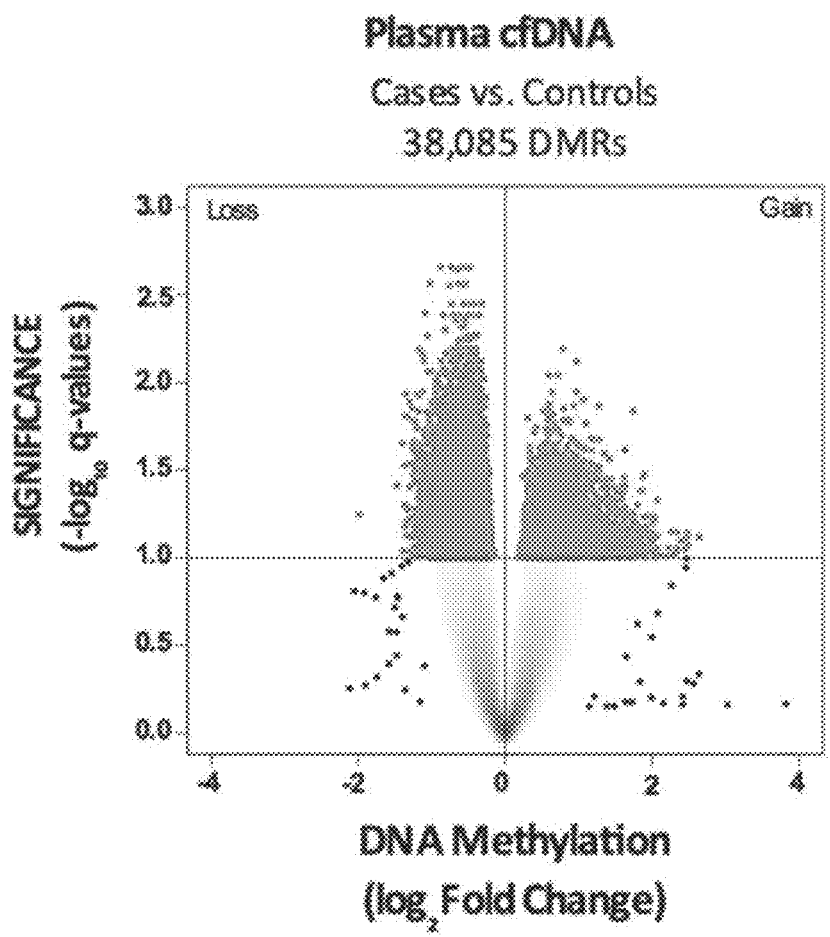
Figure 5C:
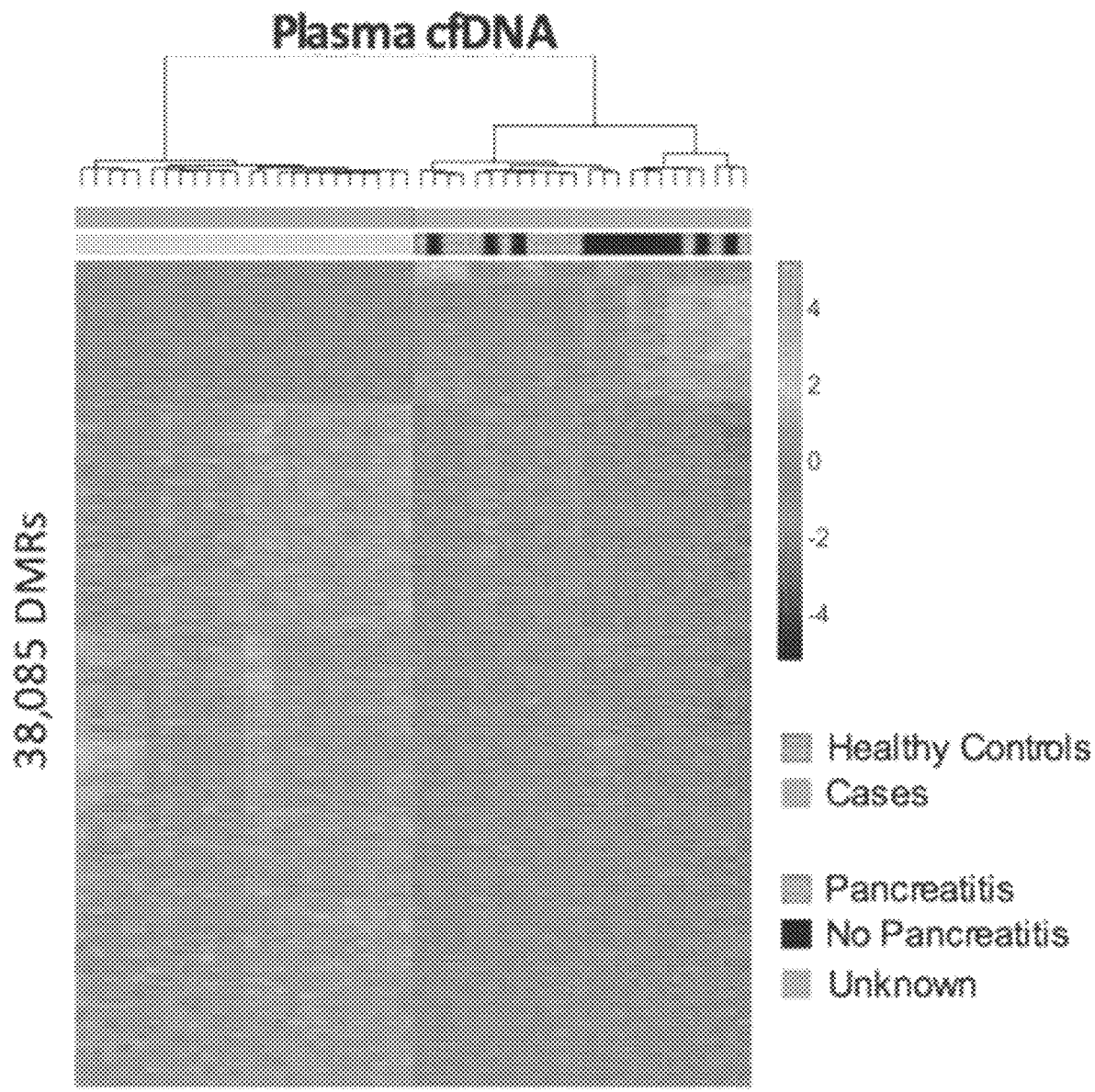

Calculation and Visualization of Differentially Methylated Regions from cfDNA of Pancreatic Cancer Patients and Healthy Donors Differentially Methylated Regions (DMRs) between cfDNA samples from 24 Pancreatic Cancer (PC) patients and 24 Healthy Donors were calculated using the MEDIPS R package[25]. For each sample, the BAM alignment (to human genome hg19) files were used to create MEDIPS R objects. Next, DMRs were calculated by comparing the RPKMs from the two sets of samples using t-tests. The raw p-values from the t-tests were adjusted using the Benjamini-Hochberg procedure. DMRs were then defined as all the windows with adjusted p-values less than 0.1; 38,085 total DMRs were found: 6,651 Hyper in Pancreatic Cancer patients and 31,544 Hypo. The scaled RPKM values from these DMRs were presented as a heatmap (FIG. 5C). This heatmap was made with the distance function "euclidean", and the clustering function "ward" for column-wise clustering and "average" for row-wise clustering.

Comparison of RRBS Samples from 24 Pancreatic Cancer Tissues and 5 Normal PBMCs

Five normal PBMC samples profiled by RRBS were downloaded from GEO (all control samples under Accession ID GSE89473) to compare their methylation profiles to those of 24 Pancreatic Cancer tissue RRBS samples. Downloaded bed files were parsed and processed with the R methylKit package[26]. These five samples were next compared to similarly processed RRBS samples from 24 Pancreatic Cancer patients. Custom functions were used to extract CpGs that were present in at least 18 of the 24 PC samples, and 4 of the 5 PBMC samples, and only the CpGs in autosomes were retained, to yield a Background set of 1,806,808 CpGs. From these, DMCs were obtained using the criteria of Benjamini-Hochberg adjusted p-value<0.01 and Delta Beta>0.25, and 134,021 DMCs were found to be Hyper in Pancreatic Cancer compared to PBMCs. Analogously, using the same q-value cutoff and Delta Beta<−0.25, we obtained 179,662 Hypo DMCs. The total of 313,683 DMCs are represented by the red points in the corresponding volcano plot (FIG. 7F), in which the negative log 10 of the q-values are plotted against the Delta Betas (the horizontal line at negative log 10 q-value=2 represents the q-value cutoff for calling DMCs, and the dotted vertical lines represents the Delta Beta cutoffs).

Figure 5D:
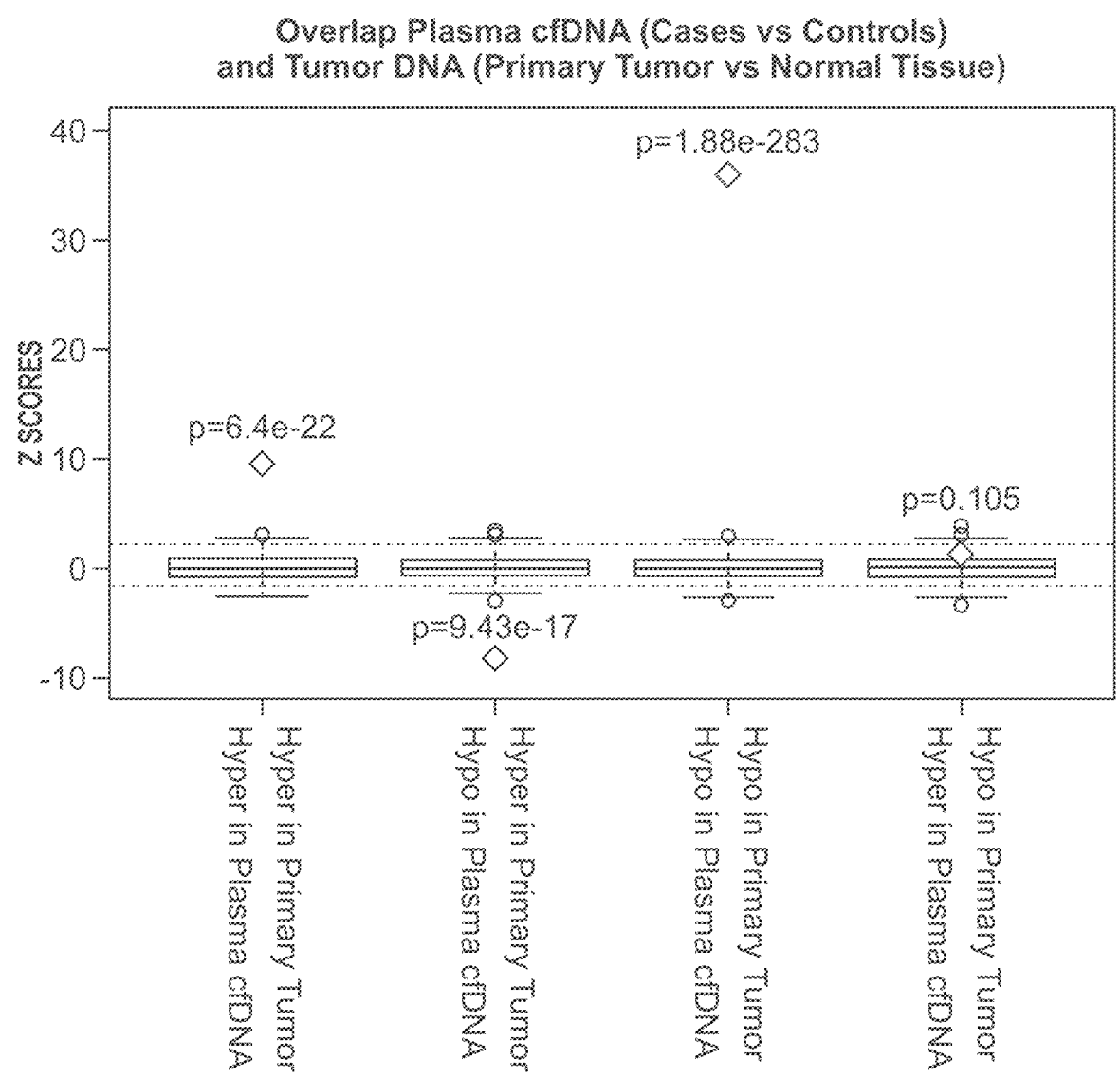
Figure 5E:
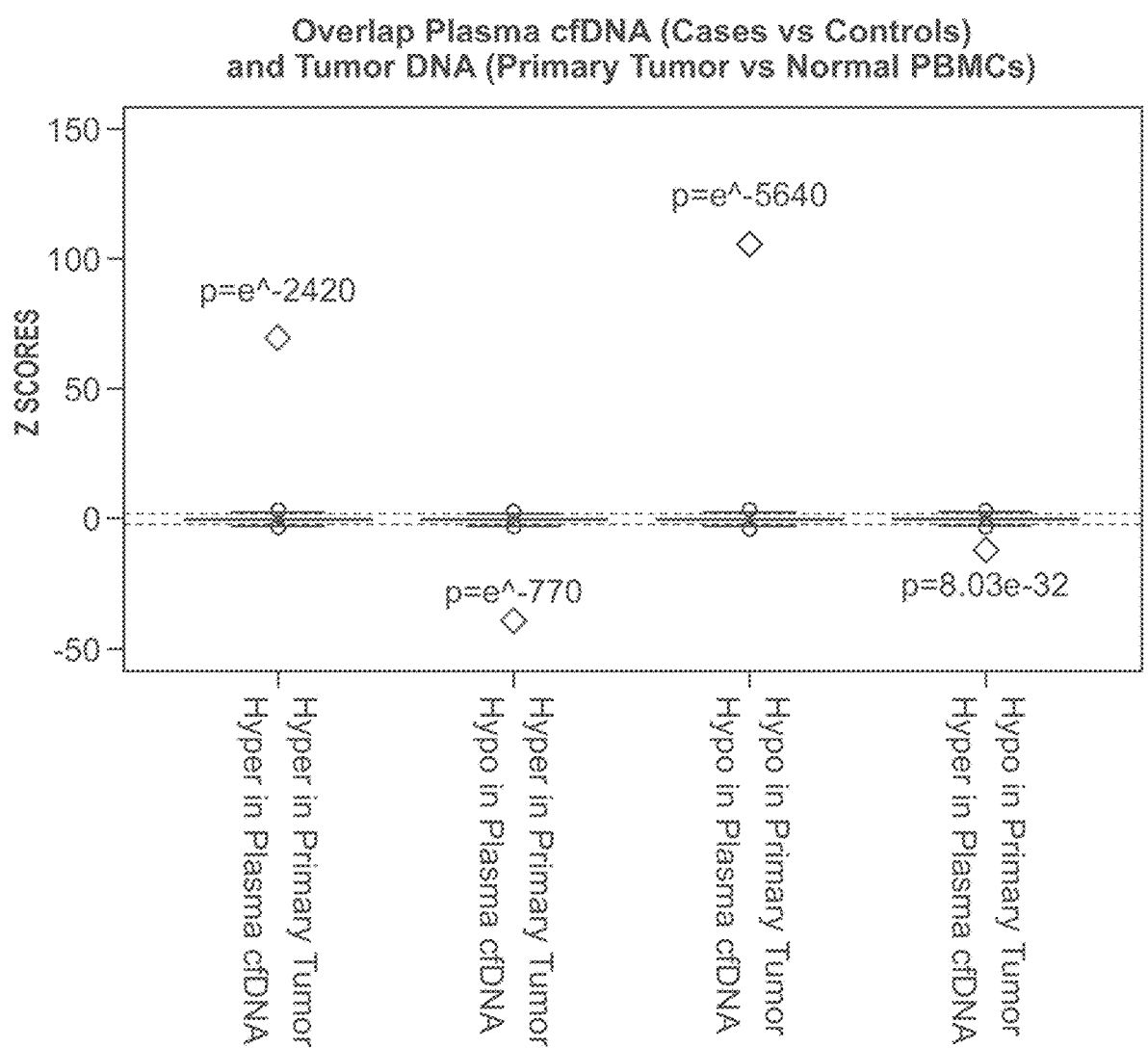
Figure 6A:
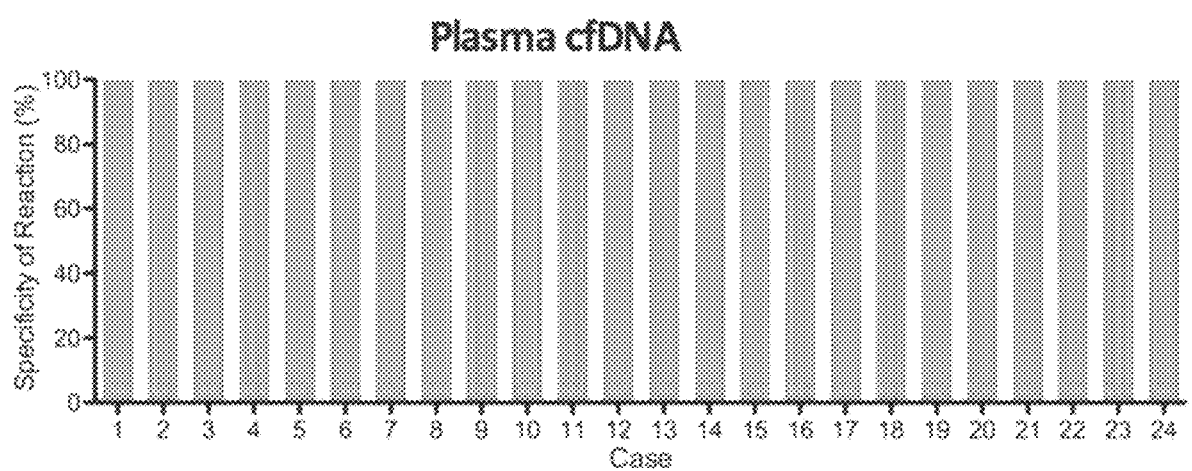
FIG. 6A-6D shows quality controls for cfMeD1P-seq from circulating cfDNA from pancreatic adenocarcinoma patients (cases) and healthy donors (controls).
Figure 6B:
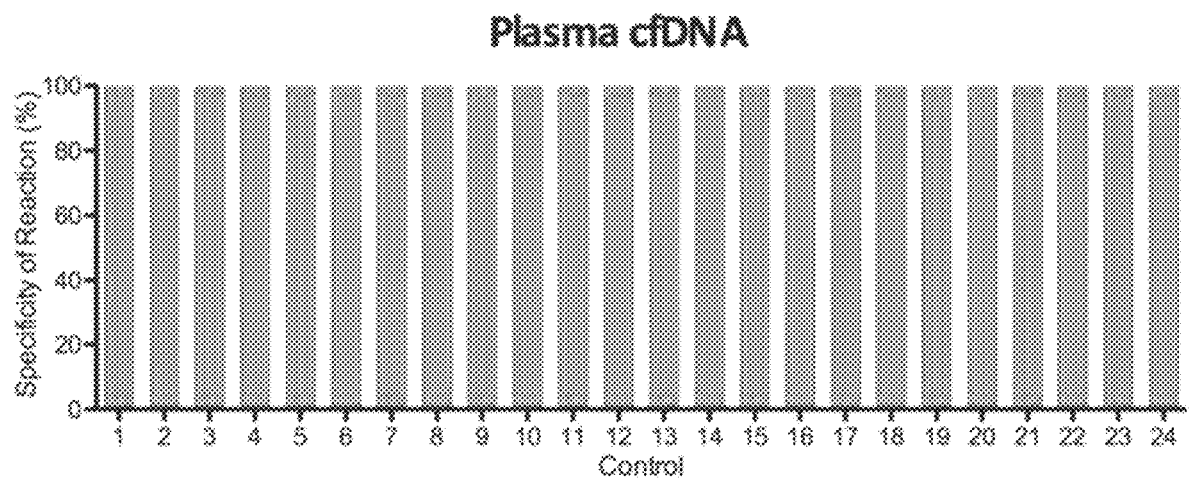
Figure 6C:
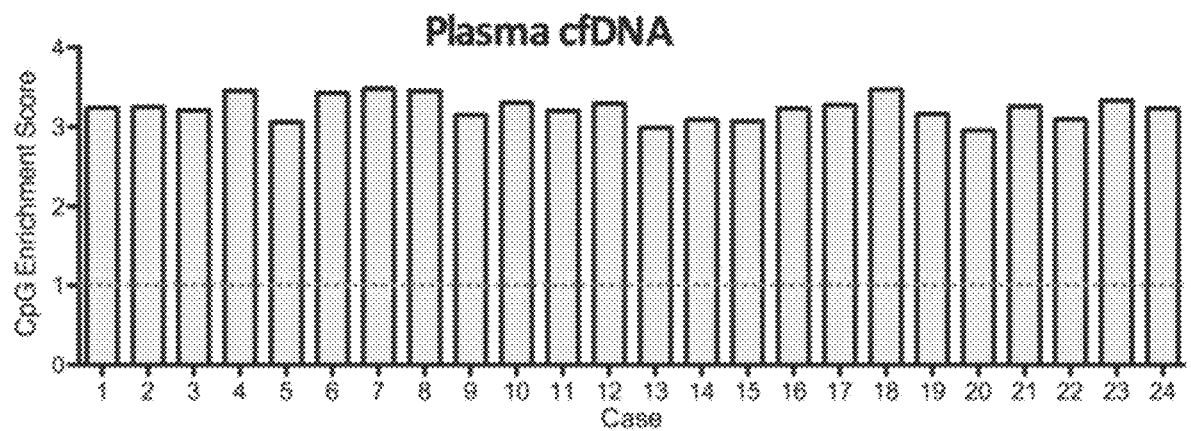
Figure 6D:
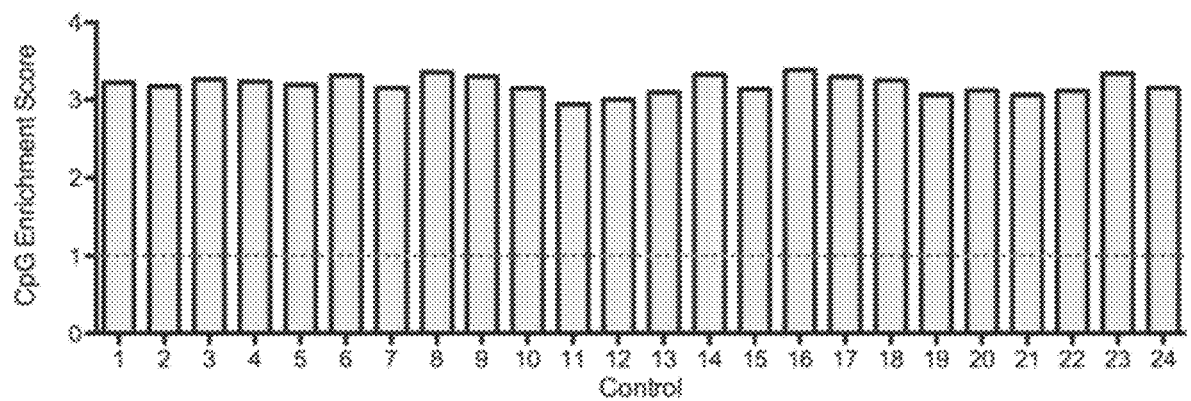

Assessment of Overlap of Differential Methylation Signals from Primary Tumors Vs Normal PBMCs and from cfDNA of Pancreatic Cancer Patients and Healthy Donors Permutation analysis was carried out to compare the frequency of expected versus the observed overlap between the DMRs identified in the plasma (with circulating cfDNA subjected to our cfMeDIP-seq protocol) and the cancer-specific DMCs identified in the primary tumor tissue (with RRBS). We examined four possible cases: Hyper DMCs overlapping with Hyper DMRs, Hyper DMCs with Hypo DMRs, Hypo DMCs with Hypo DMRs, and finally, Hypo DMCs with Hyper DMRs. For each case, the Hyper or Hypo DMCs were overlapped with the Hyper or Hypo DMRs to get the number of "biological intersections"; each set of DMCs was then randomly shuffled across the Background set of 1,806,808 CpGs 1000 times, and overlapped again with each set of the DMRs. These random and biological intersections were put on the same scale using Z-scores and are shown with boxplots and diamonds, respectively (FIG. 5E). The dashed horizontal lines in these plots represent the cutoff Z-scores associated with a Bonferroni adjustment-derived q-value of 0.05.

Comparison of RRBS Samples from 24 Pancreatic Cancer Tissues and 24 Normal Tissues & Assessment of Overlap of Differential Methylation Signal from these Tissues and from cfDNA of Pancreatic Cancer Patients and Healthy Donors The 24 PC samples that were compared to 5 Normal PBMC samples were also compared separately to 24 normal tissues from the same patients. The Background set (763,874 CpGs) and DMCs Hyper & Hypo in PC (34,013 & 11,160 respectively) were calculated using the same methodology, and these were used to construct a volcano plot (FIG. 7C) & boxplots (FIG. 5D) in the same manner as well.

PCA Plots on 24 PC and 24 Healthy cfDNA Samples

We performed unsupervised clustering analysis with PCA (FIG. 7A-B) on the 24 PC and 24 Healthy cfDNA samples using the top million most variable genome-wide windows. For each window, variability was calculated using the MAD (Mean Absolute Deviation) metric. This is a robust measurement that returns the median of the absolute deviations from the data's median value, where the data is the RPKM values across these 48 samples for a given window.

Heatmaps with GTEx Expression Profiles of TFs Associated with Motifs Hypomethylated in 24 PC and 24 Healthy cfDNA Samples RNA-Seq data was obtained from the GTEx database in the form of median RPKMs by tissue for all human genes (obtained from file GTEx_Analysis_v6p_RNA-seq_RNA-SeQCv1.1.8_gene_median_rpkm.gct.gz under https://gtexportal.org/home/datasets). TFs of interest were matched to their gene names, and heatmaps (FIG. 8A, 8C) were constructed with the median RPKMs of each TF scaled across all tissues. The distance function "manhattan" and clustering function "average" were used for both row-wise and column-wise clustering.

Violin Plots with GTEx Expression Profiles of TFs Associated with Motifs Hypomethylated in 24 PC and 24 Healthy cfDNA Samples In order to estimate if the TFs for which we detected significantly enriched motifs in hypomethylated regions in cases versus controls were significantly upregulated in pancreatic cancer samples, we used a randomisation test with the ssGSEA score as the test statistic. For each sample, we computed the scores using the 85 TFs found significantly associated with hypomethylated motifs, and 1,000 random sets of 85 TFs (the list of all human TFs was obtained from file TFCheckpoint_download_180515. txt under http://www.tfcheckpoint.org/data/); expression levels from 178 pancreatic adenocarcinoma patients on TCGA were used.

Figure 8B:
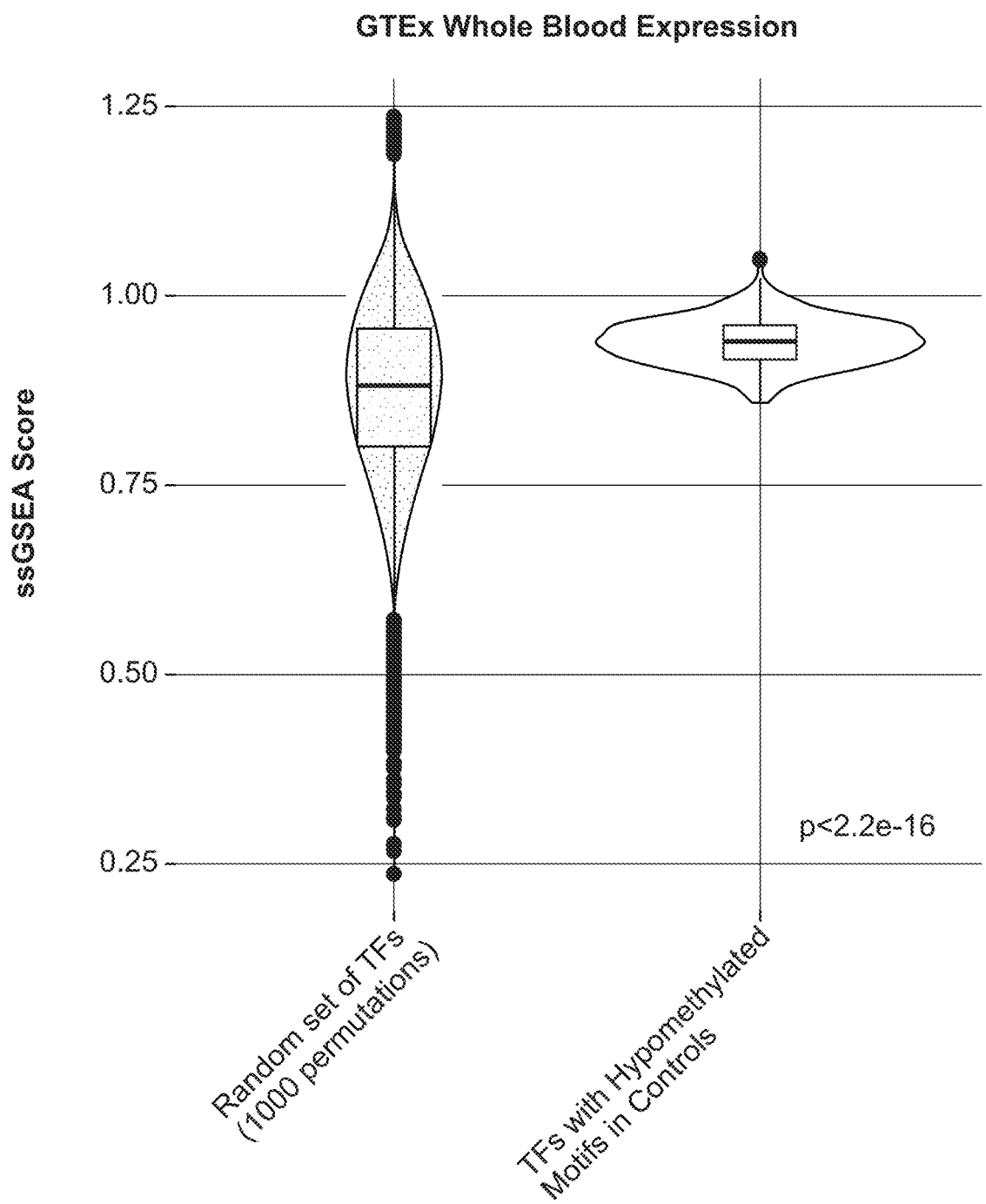
Figure 8C:
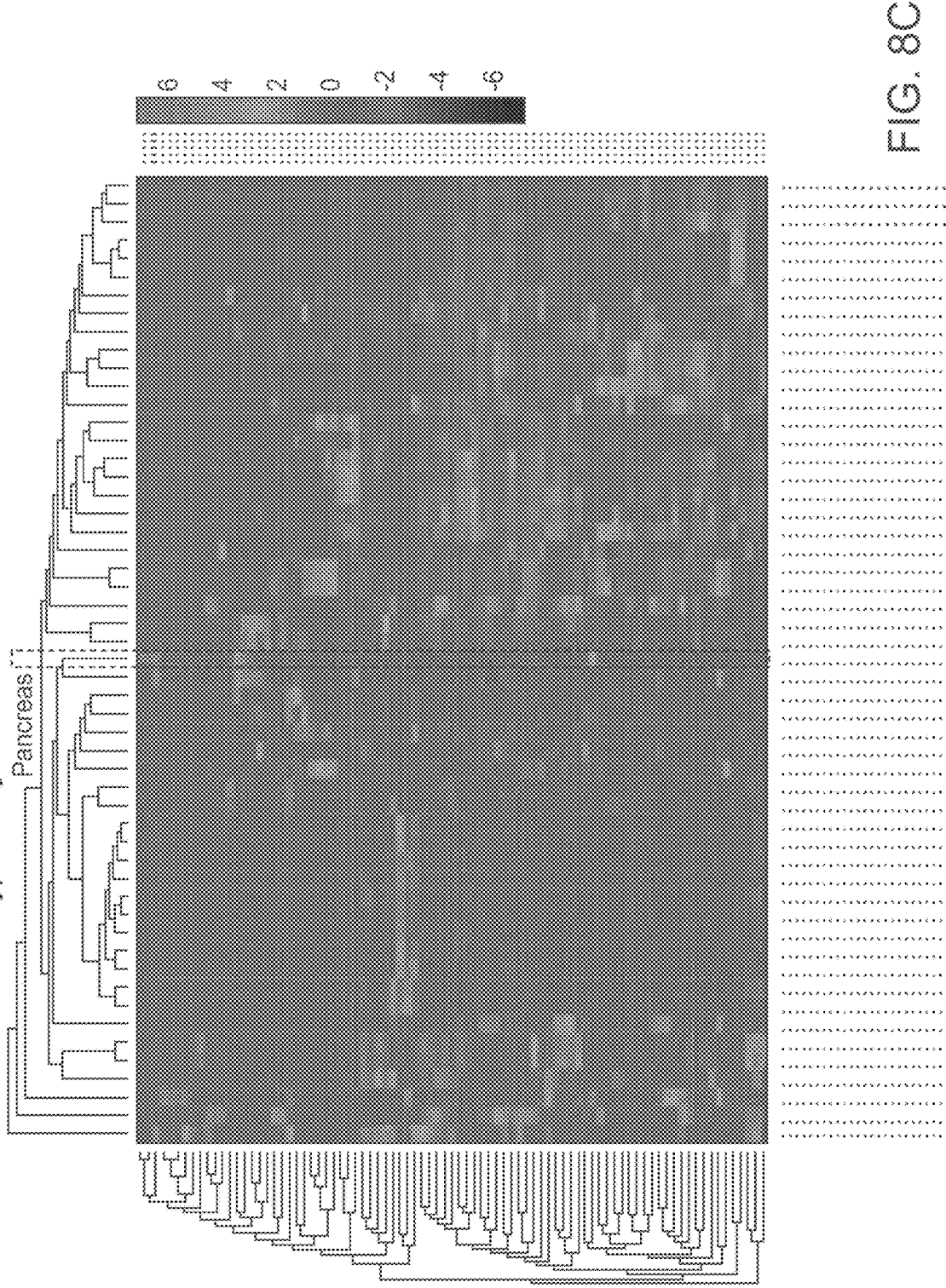
Figure 8D:
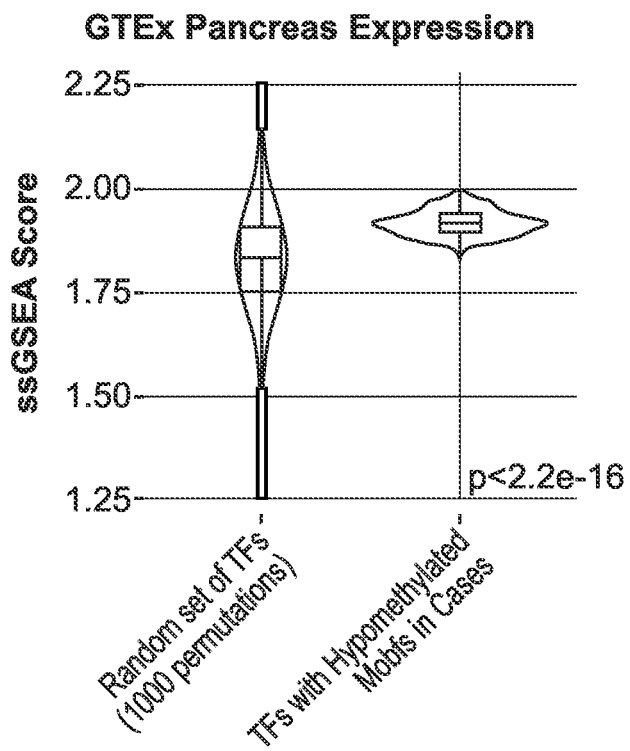
Figure 8E:
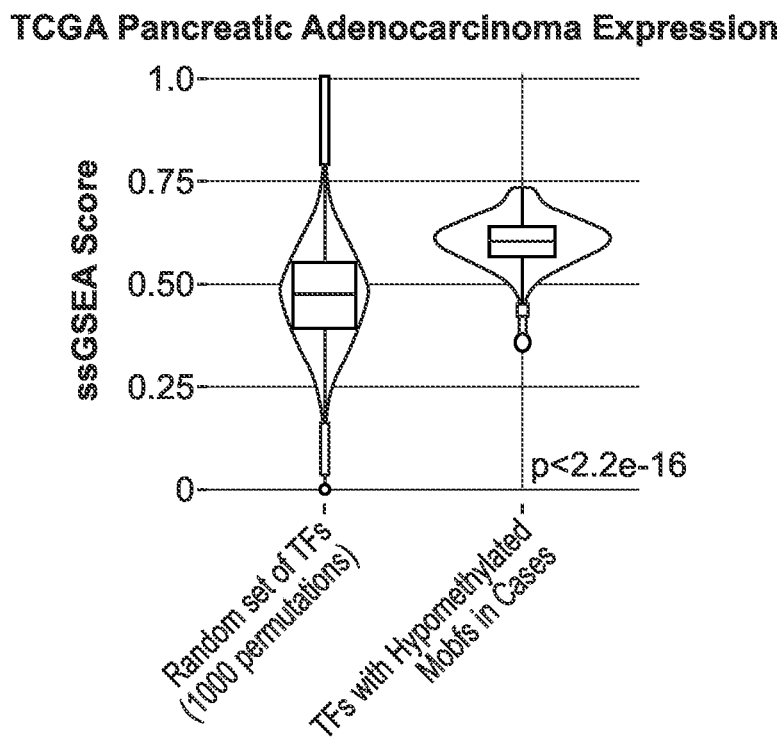

The distribution of these scores can be seen in the associated violin plots (FIG. 8E).

A Wilcoxon's Rank Sum test was then used to compare the random distribution versus the observed distribution, yielding a p-value<2.2e-16.

The same analysis was done on the GTEx data with normal pancreas (FIG. 8D). The analysis was also repeated with TFs (n=33) whose motifs were identified as hypomethylated footprints in the plasma cfDNA from healthy donors, on the GTEx data with whole blood (FIG. 8B).

Results/Discussion

A Genome-Wide Method Suitable for cfDNA Methylation Mapping

The cfMeDIP-seq method described here was developed through the modification of an existing low input MeDIP-seq protocol[17] that is robust down to 100 ng of input DNA.

However, the majority of plasma samples yield much less than 100 ng of DNA. To overcome this challenge, we added exogenous λ DNA (filler DNA) to the adapter-ligated cfDNA library in order to artificially inflate the amount of starting DNA to 100 ng (FIG. 2). This minimizes the amount of non-specific binding by the antibody and also minimizes the amount of DNA lost due to binding to plasticware. The filler DNA consisted of amplicons similar in size to an adapter-ligated cfDNA library and was composed of unmethylated and in vitro methylated DNA at different CpG densities. The addition of this filler DNA also serves a practical use, as different patients will yield different amounts of cfDNA, allowing for the normalization of input DNA amount to 100 ng. This ensures that the downstream protocol remains exactly the same for all samples regardless of the amount of available cfDNA.

Figure 3A:
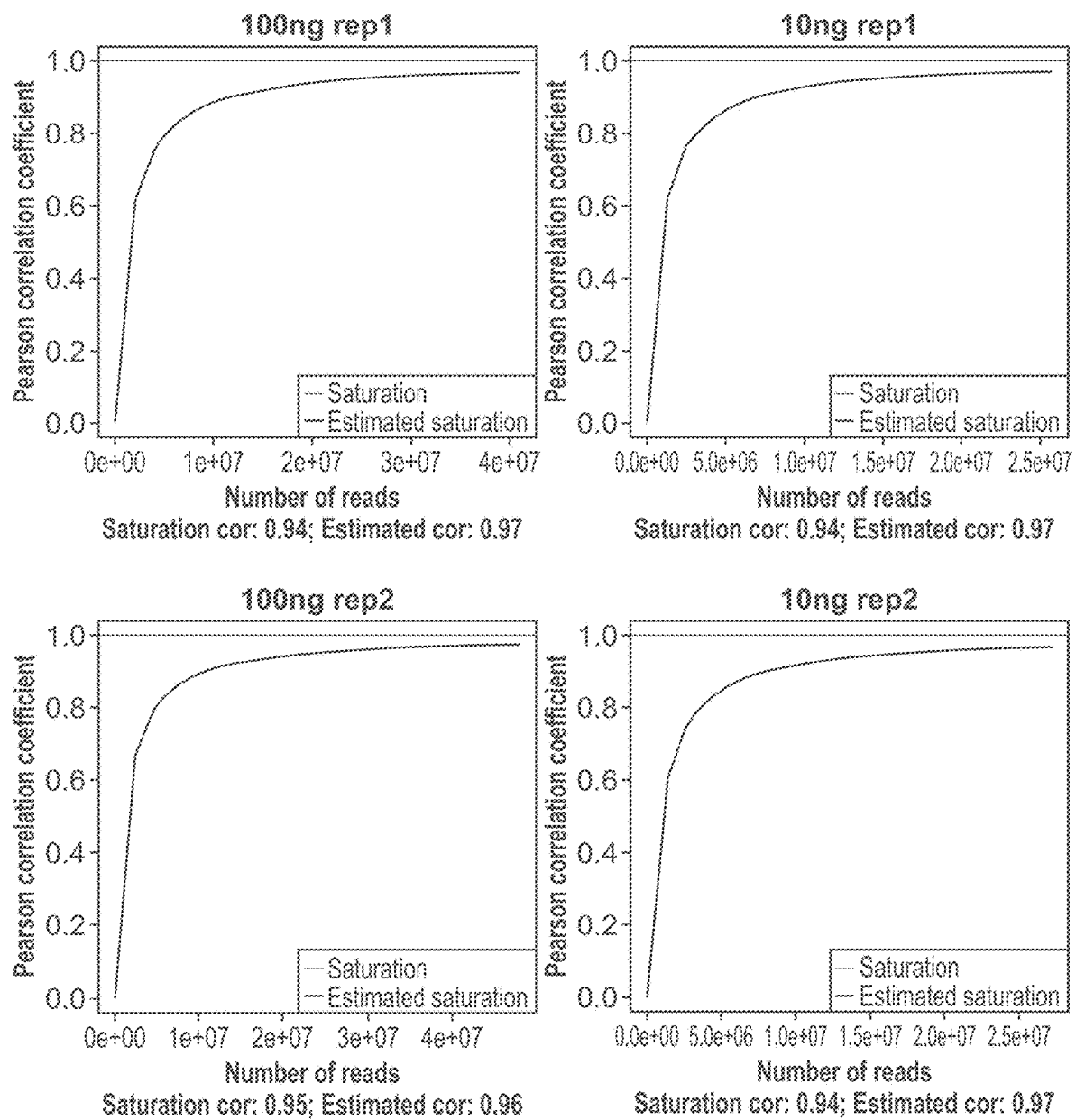
FIGS. 3A-3C show sequencing saturation analysis and quality controls.
Figure 3B:
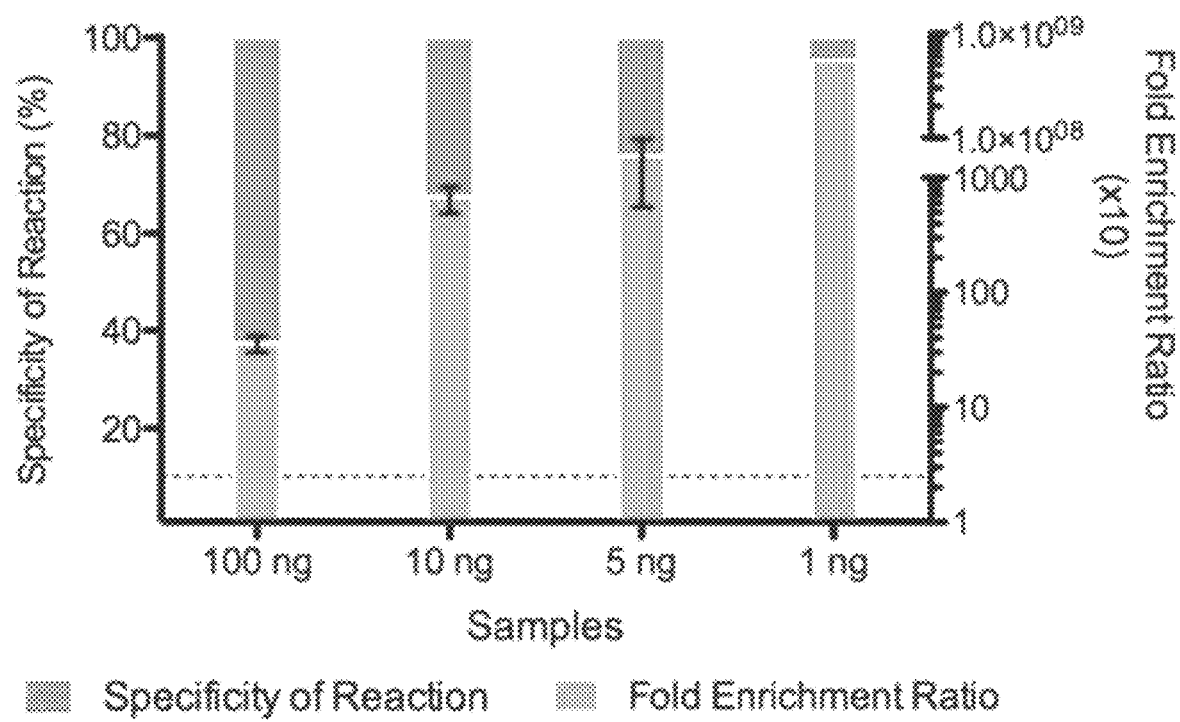

We first validated the cfMeDIP-seq protocol using DNA from human colorectal cancer cell line HCT116, sheared to a fragment size similar to that observed in cfDNA. HCT116 was chosen because of the availability of public DNA methylation data. We simultaneously performed the gold standard MeDIP-seq protocol[17] using 100 ng of sheared cell line DNA and the cfMeDIP-seq protocol using 10 ng, 5 ng, and 1 ng of the same sheared cell line DNA. This was performed in two biological replicates. For all the conditions, we obtained more than 99% specificity of the reaction (1−[recovery of spiked-in unmethylated control DNA over recovery of spiked-in methylated control DNA]), and a very high enrichment of a known methylated region over an unmethylated region (TSH2B0 and GAPDH, respectively) (FIG. 3B).

Figure 3C:
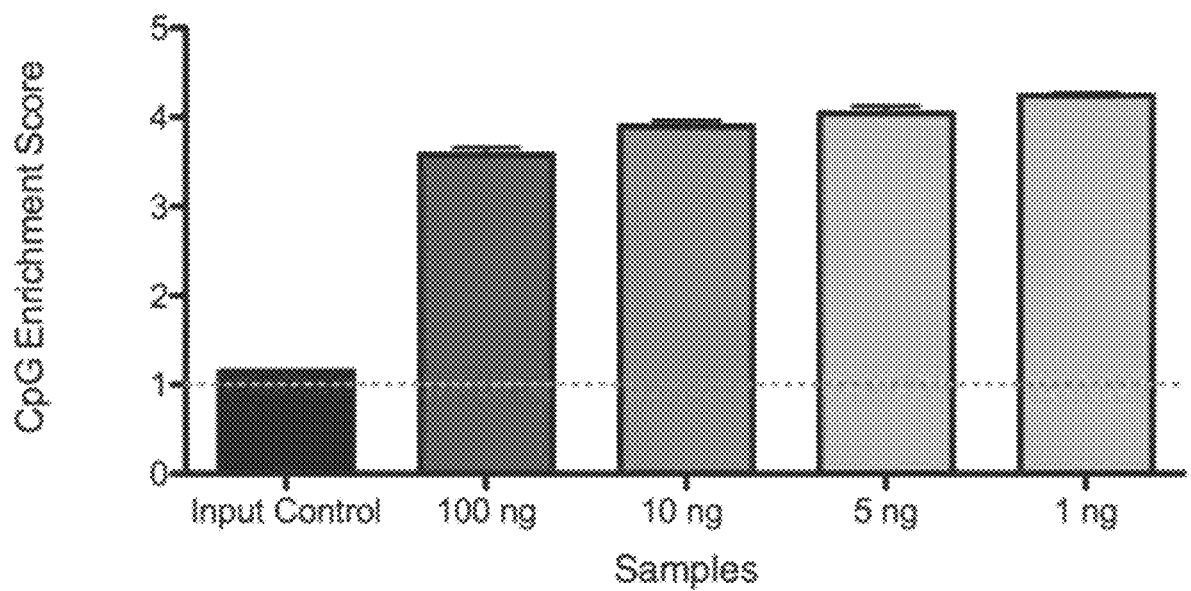
Figure 4A:
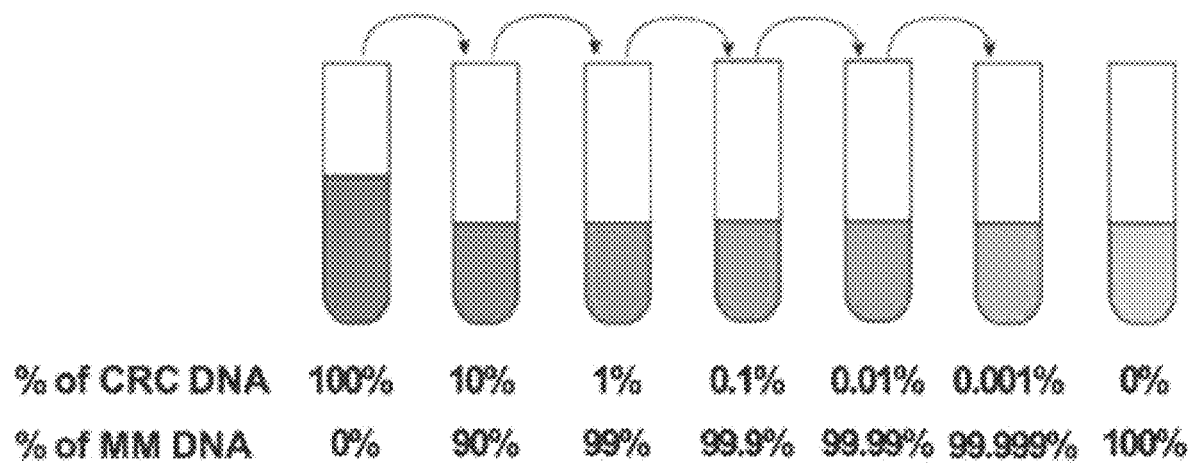
FIGS. 4A-4D show quality controls from cfMeDIP-seq from serial dilution.
Figure 4B:
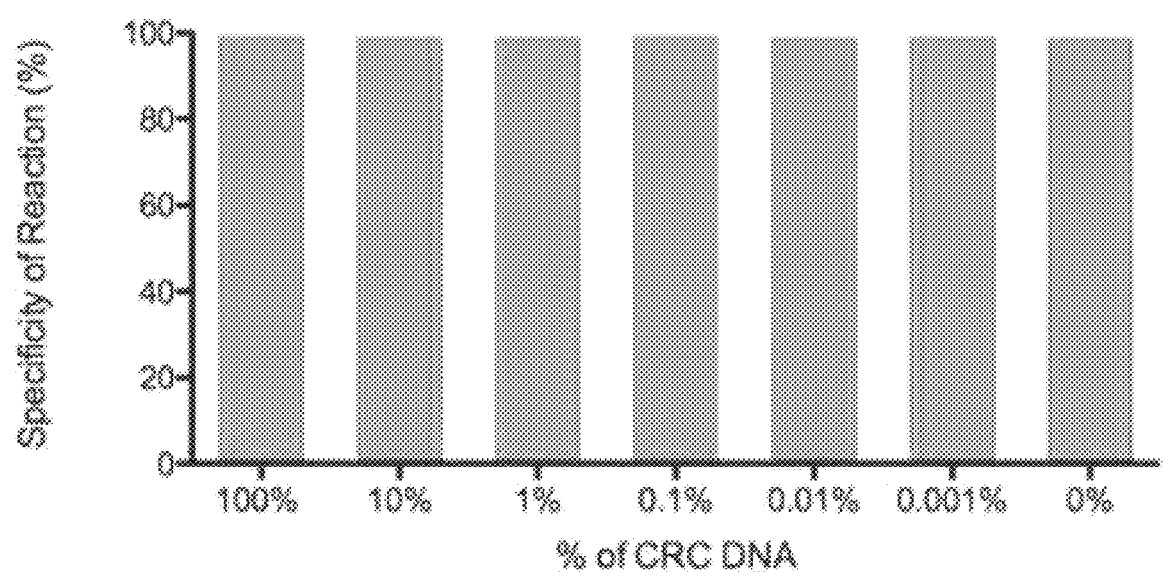
Figure 4C:
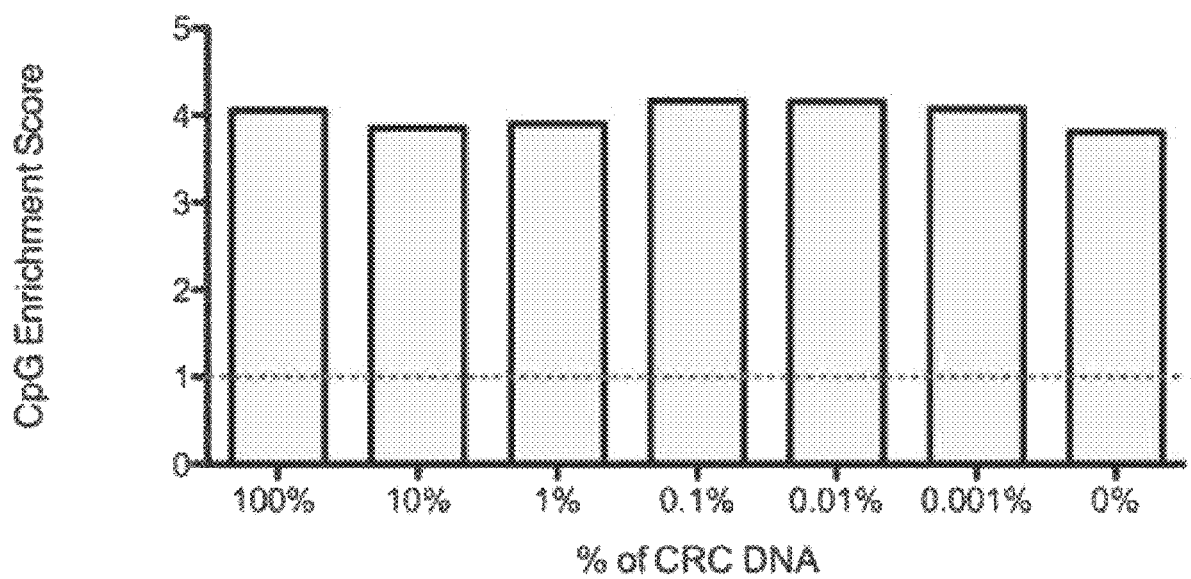
Figure 4D:
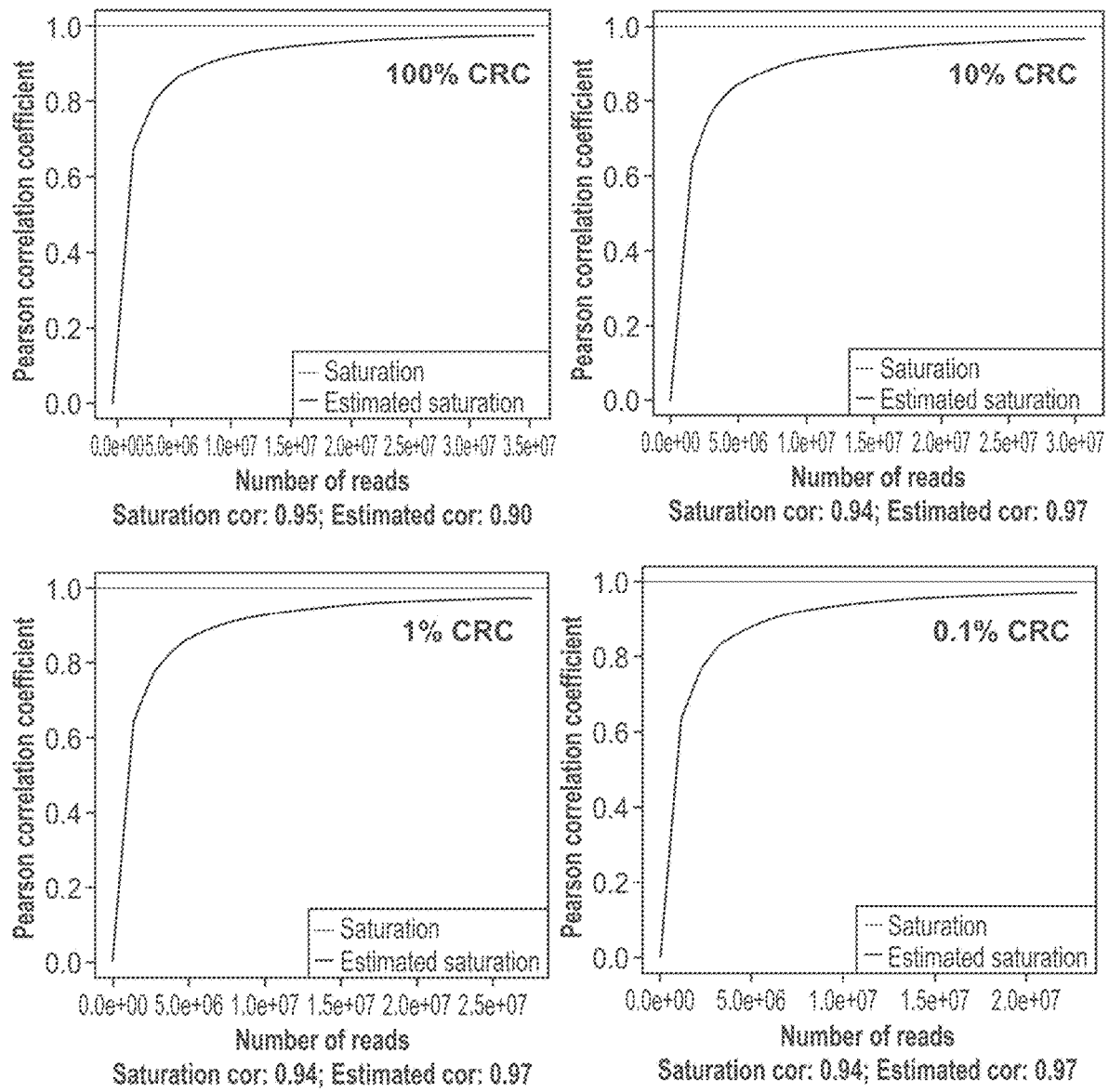
Figure 4D:
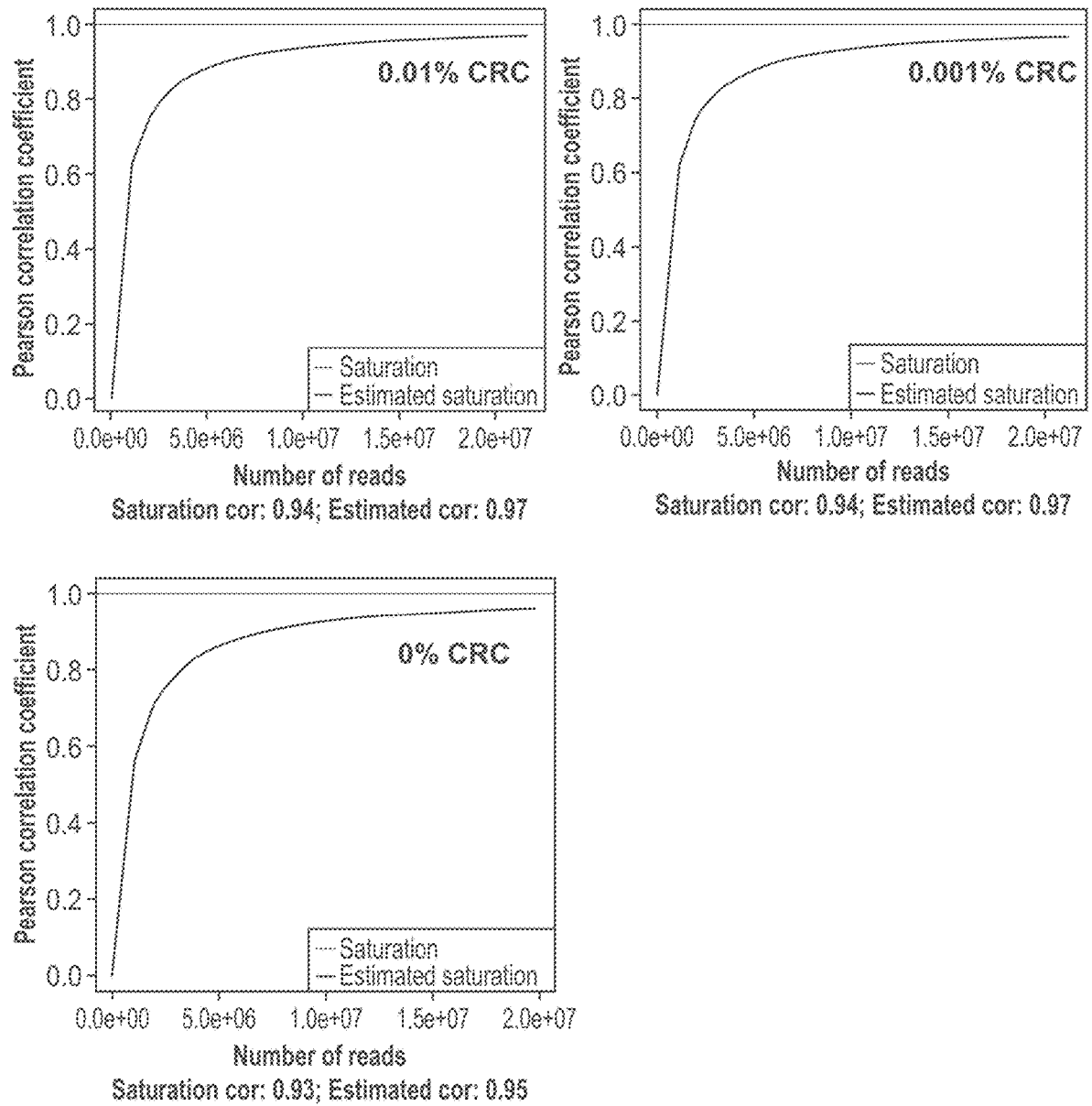

The libraries were sequenced to saturation (FIG. 3A) at around 30 to 70 million reads per library (Table 2). The raw reads were aligned to both the human genome and the λ genome, and found virtually no alignment was found to the λ genome (Table 3A and 3B). Therefore, the addition of the exogenous λ DNA as filler DNA did not interfere with the generation of sequencing data. Finally, we calculate the CpG Enrichment Score as a quality control measure for the immunoprecipitation step[25]. All the libraries showed similar enrichment for CpGs while the input control, as expected, showed no enrichment (FIG. 3C), validating our immunoprecipitations even at extremely low inputs (1 ng).

Figure 1B:
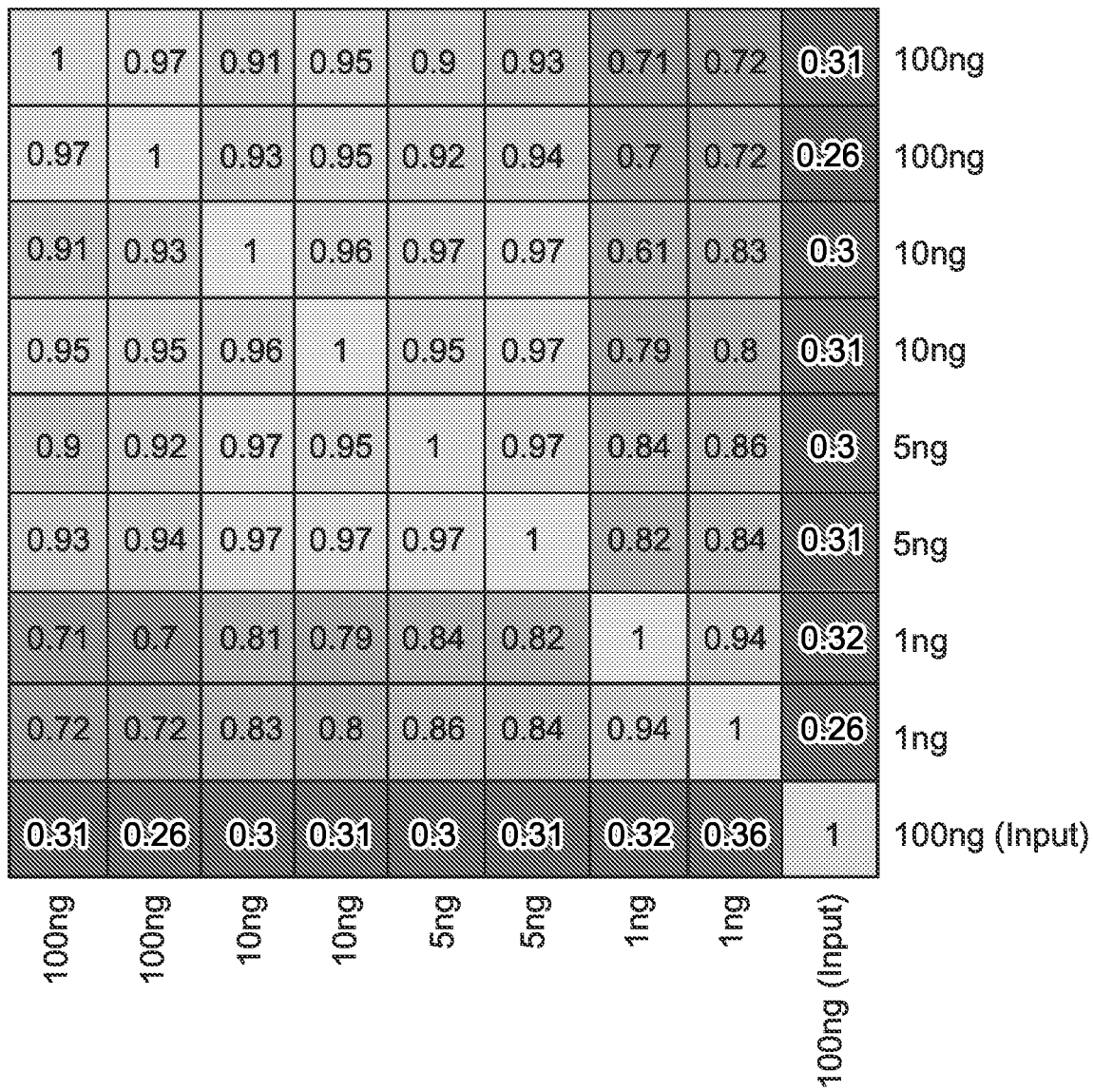
Figure 1C:
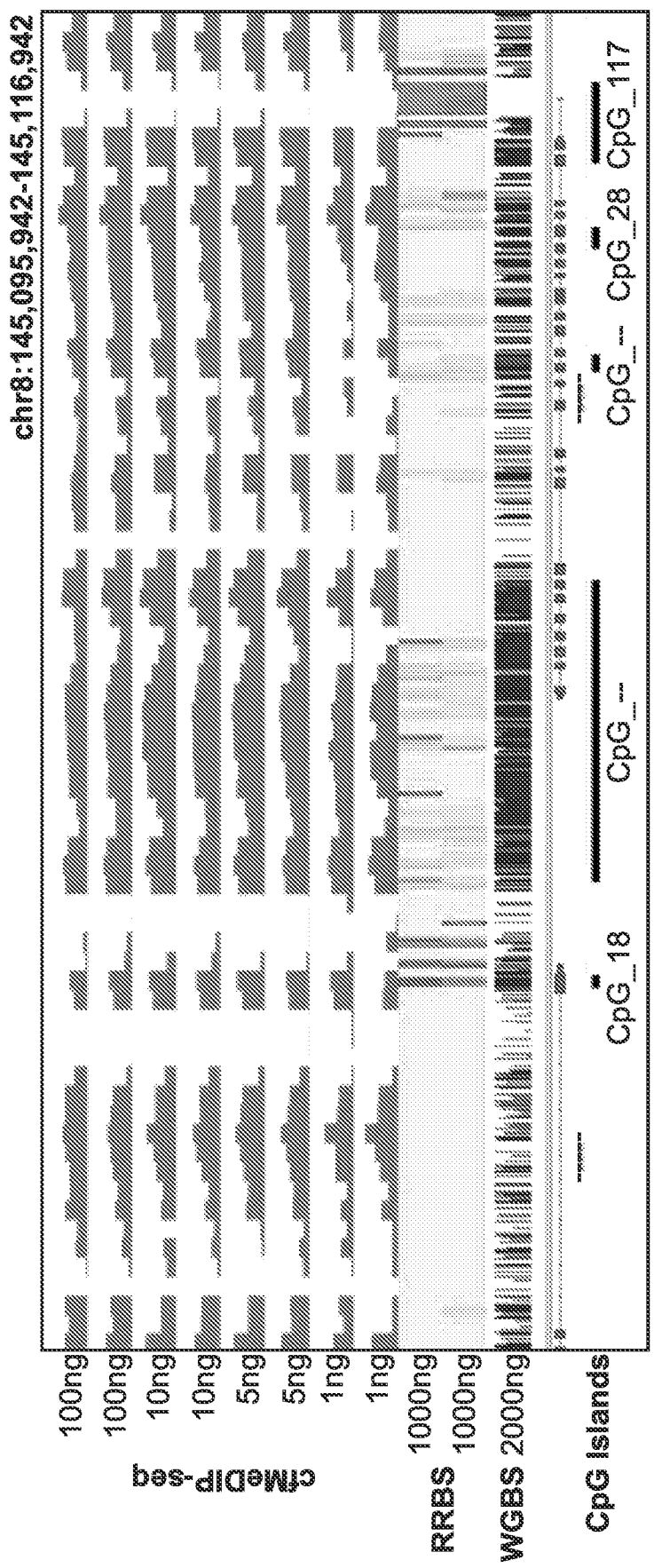

Genome-wide correlation estimates comparing different input DNA levels show that both MeDIP-seq (100 ng) and cfMeDIP-seq (10, 5, and 1 ng) methods were very robust, with Pearson correlation of at least 0.94 between any two biological replicates (FIG. 1B). The analysis also demonstrates that cfMeDIP-seq at 5 and 10 ng of input DNA can robustly recapitulate the methylation profile obtained by traditional MeDIP-seq at 100 ng (Pairwise Pearson correlation of at least 0.9) (FIG. 1B). The performance of cfMeDIP-seq at 1 ng of input DNA is reduced compared to MeDIP-seq at 100 ng but still shows a strong Pearson correlation at >0.7 (FIG. 1B). We also observed that the cfMeDIP-seq protocol recapitulates the DNA methylation profile of HCT116 using gold standard RRBS (Reduced Representation Bisulfite Sequencing) and WGBS (Whole-Genome Bisulfite Sequencing) (FIG. 1C). Altogether, our data suggests that cfMeDIP-seq is a robust protocol for genome-wide methylation mapping of fragmented and low input DNA material, such as circulating cfDNA.

cfMeDIP-Seq Displays High-Sensitivity for Detection of Tumor-Derived ctDNA

Figure 1D:
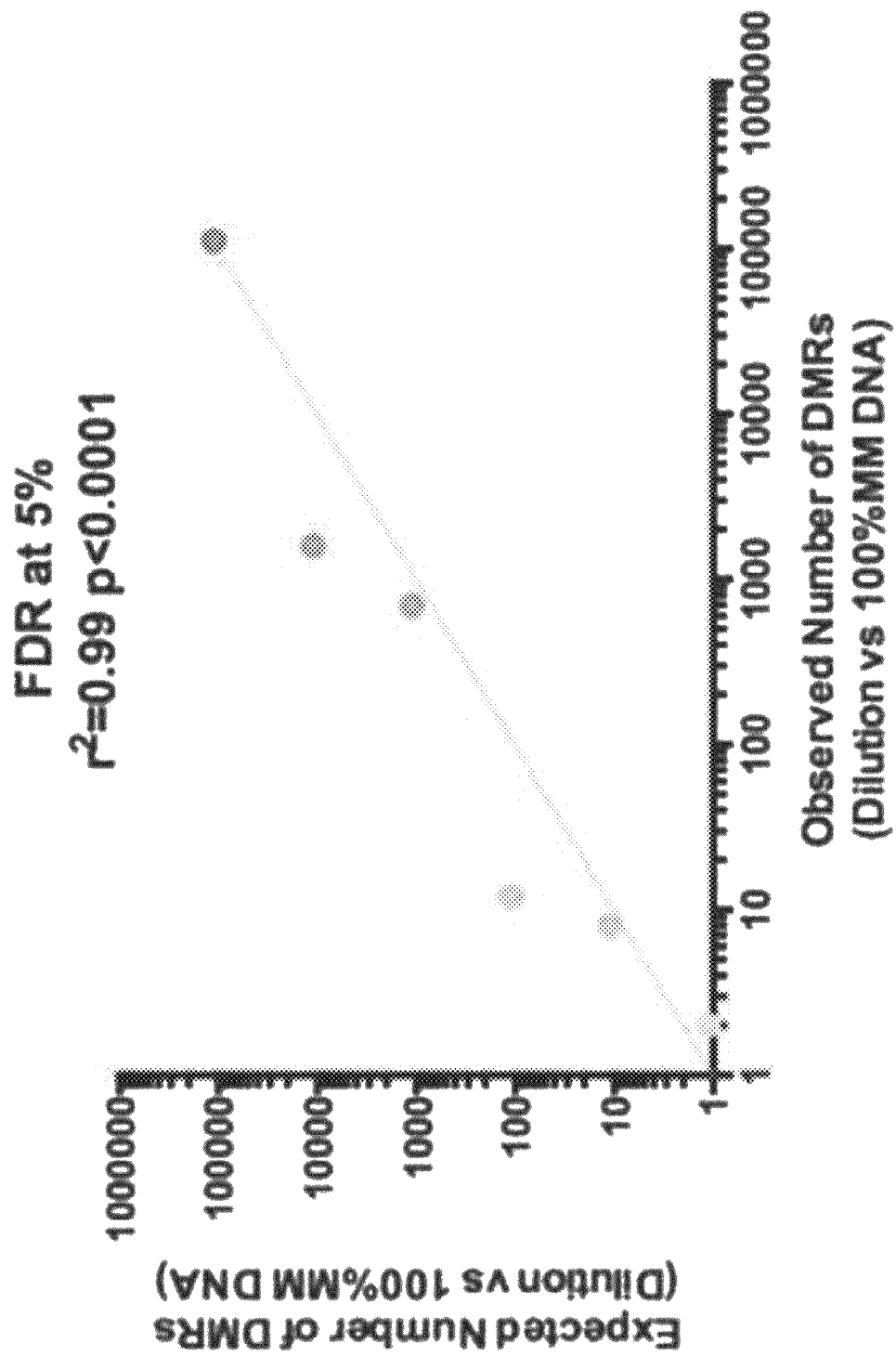
Figure 1E:
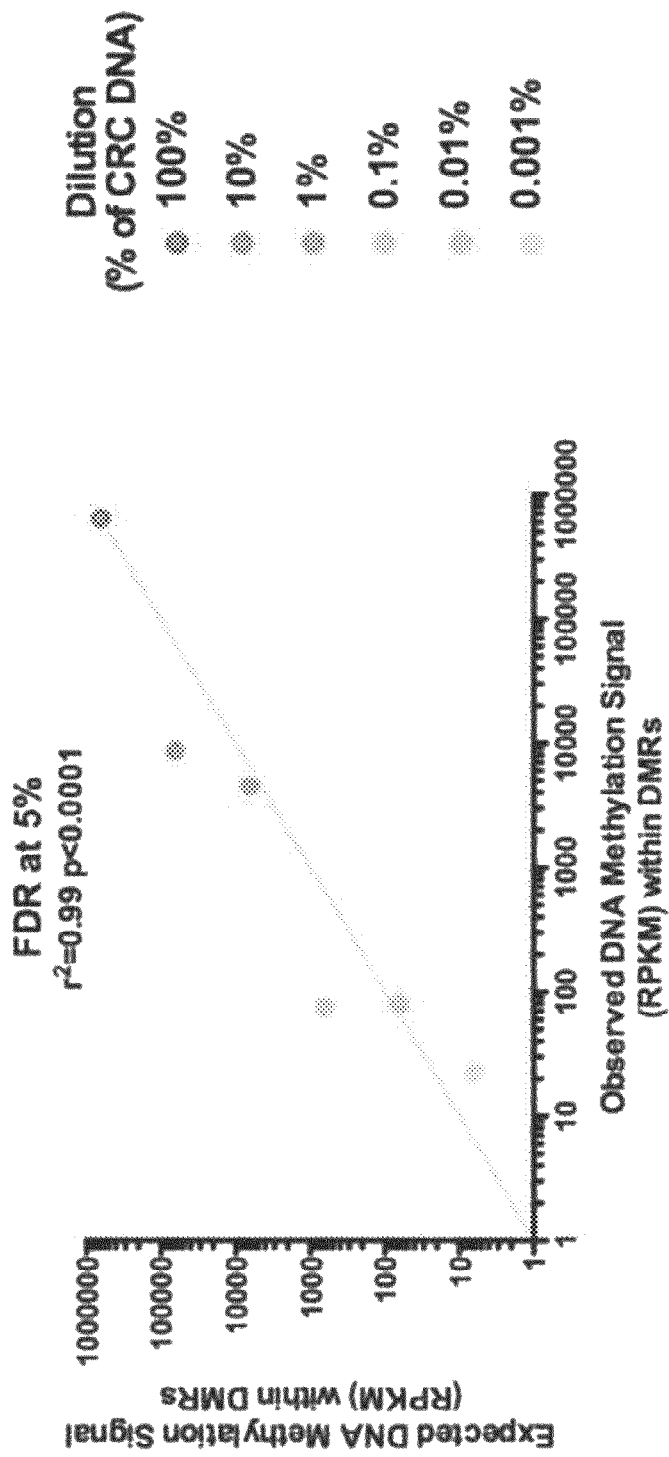
Figure 1F:
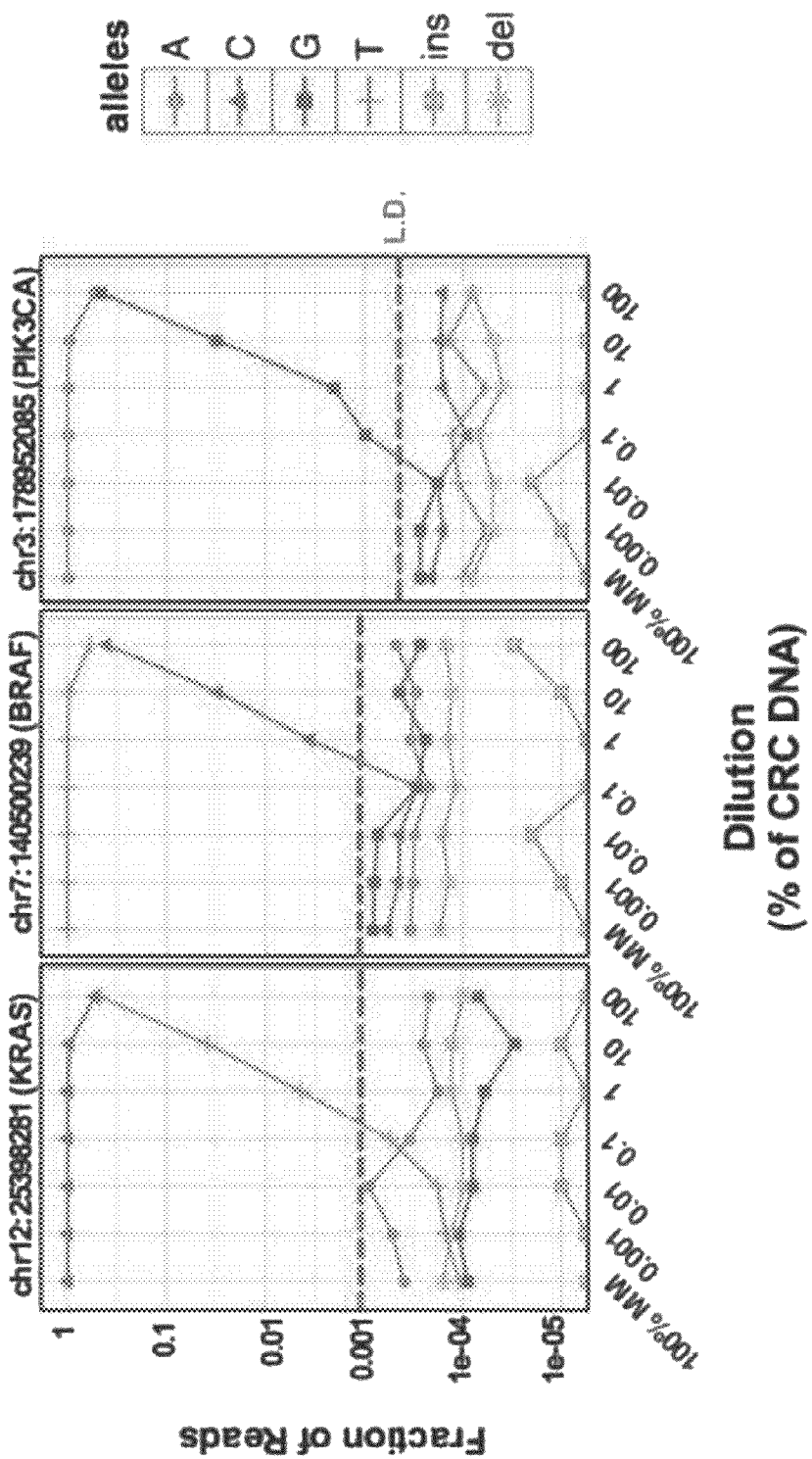

To evaluate the sensitivity of the cfMeDIP-seq protocol, we performed a serial dilution of Colorectal Cancer (CRC) HCT116 cell line DNA into a Multiple Myeloma (MM) MM1.S cell line DNA, both sheared to mimic cfDNA sizes. We diluted the CRC DNA from 100%, 10%, 1%, 0.1%, 0.01%, 0.001%, to 0% and performed cfMeDIP-seq on each of these dilutions (FIG. 4A-D). We also performed ultra-deep (10,000× median coverage) targeted sequencing for detection of three point mutations in the same samples. The observed number of DMRs identified at each CRC dilution point versus the pure MM DNA using a 5% False Discovery rate (FDR) threshold was almost perfectly linear ($r^2$=0.99, p<0.0001) with the expected number of DMRs based on the dilution factor (FIG. 1D) down to a 0.001% dilution. Moreover, the DNA methylation signal within these DMRs also shows almost perfect linearity ($r^2$=0.99, p<0.0001) between the observed versus expected signal (FIG. 1E). In comparison, beyond the 1% dilution, ultra-deep targeted sequencing could not reliably distinguish between the CRC-specific variants and the spurious variants due to PCR or sequencing-errors (FIG. 1F). Thus, cfMeDIP-seq displays excellent sensitivity for the detection of cancer-derived DNA, exceeding the performance of variant detection by ultra-deep targeted sequencing using a standard protocol.

Figure 1G:
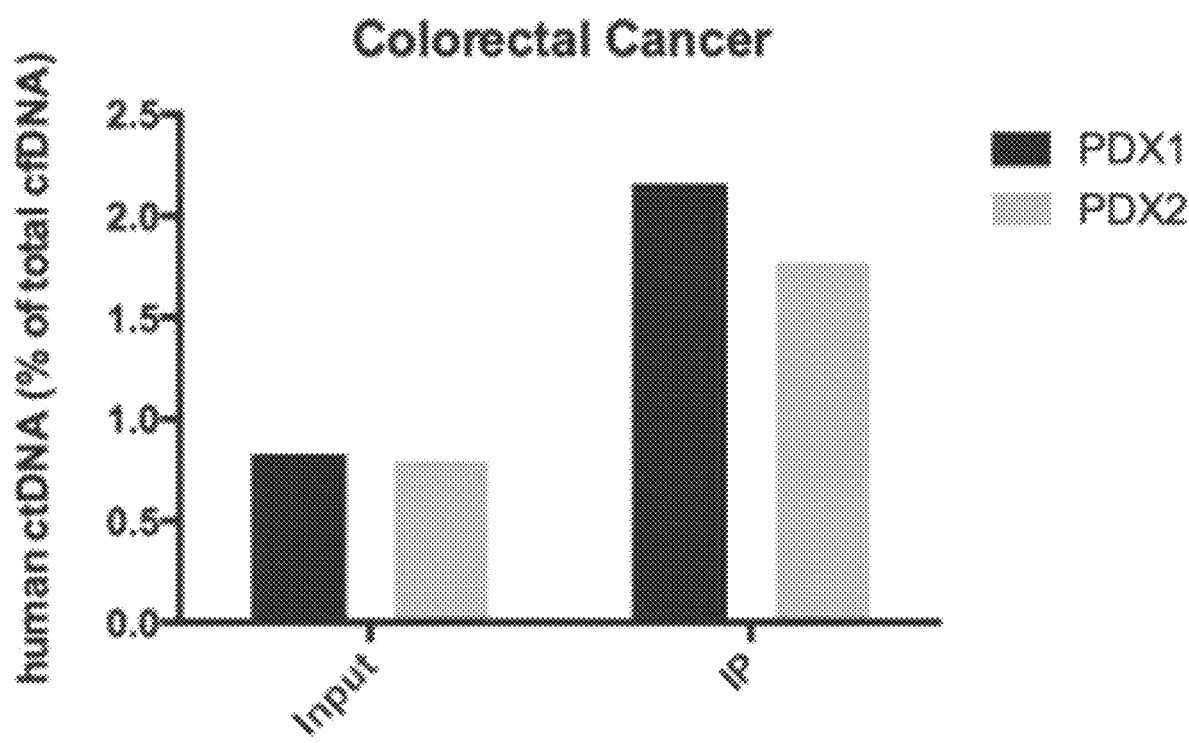

Cancer DNA is frequently hypermethylated at CpG-rich regions[1]. Since cfMeDIP-seq specifically targets methylated CpG-rich sequences, we hypothesized that ctDNA would be preferentially enriched during the immunoprecipitation procedure. To test this, we generated patient-derived xenografts (PDXs) from two colorectal cancer patients and collected the mouse plasma. Tumor-derived human cfDNA was present at less than 1% frequency within the total cfDNA pool in the input samples and at 2-fold greater abundance following immunoprecipitation (FIG. 1G). These results suggest that through biased sequencing of ctDNA, the cfMeDIP procedure could further increase ctDNA detection sensitivity.

Methylome Analysis of Plasma cfDNA Distinguishes Early Stage Pancreatic Adenocarcinoma Patients from Healthy Donors We sought to investigate whether methylome analysis of plasma cfDNA could be used to detect ctDNA in early stage cancer. We performed the methylome analysis in the pre-surgery plasma of 24 early stage pancreatic cancer patients (cases) and 24 age and sex-matched healthy donors (controls) (Tables 4A, 4B and 5). For each patient, laser-capture microdissected (LCM) tumor samples with high tumor purity and normal tissue samples were examined. cfMeDIP-seq was performed on the circulating cfDNA and RRBS on the tumor and normal tissues (FIG. 5A and FIG. 6, Tables 6A and 6B). Using a t-test and Benjamini-Hochberg correction for multiple testing, we obtained 38,085 DMRs (p<0.01, q<0.1) between the cases and controls cfDNA (FIG. 5B-C).

Figure 7A:
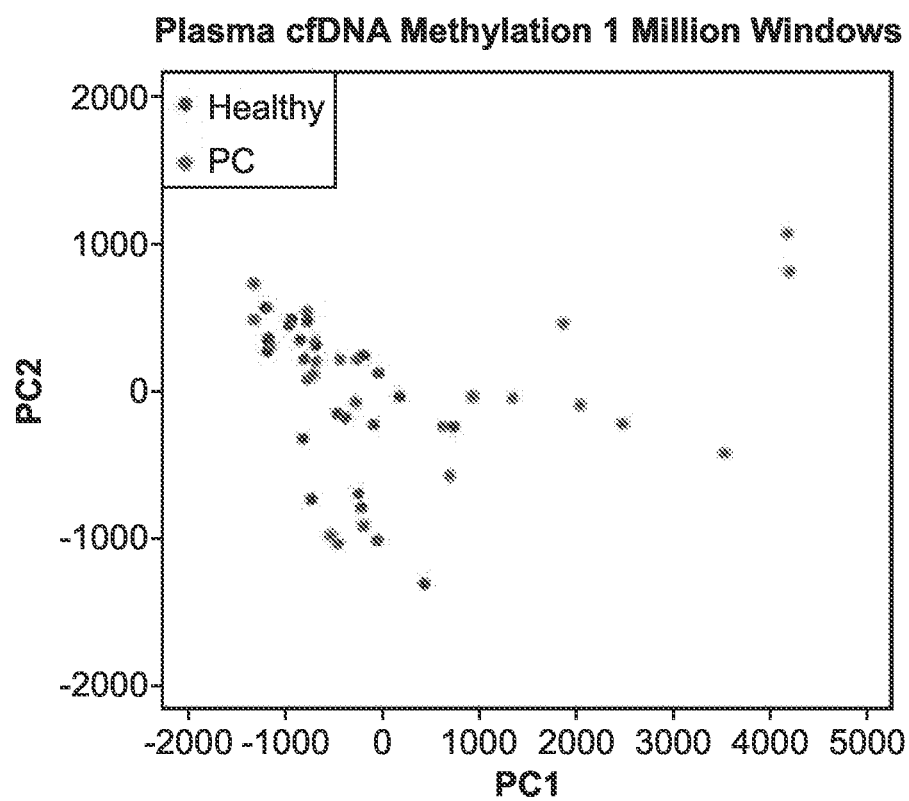
FIG. 7A shows PCA on the 48 plasma cfDNA methylation from healthy donors and early stage pancreatic adenocarcinoma patients using the top million most variable genome-wide windows. For each window, variability was calculated using the MAD (Mean Absolute Deviation) metric, which is a robust measurement that returns the median of the absolute deviations from the data's median value; in this case, the data is the RPKM values across all the 48 samples for a given window. PC1 versus PC2 (left) and PC1 versus PC3 (right) are shown.
Figure 7A:
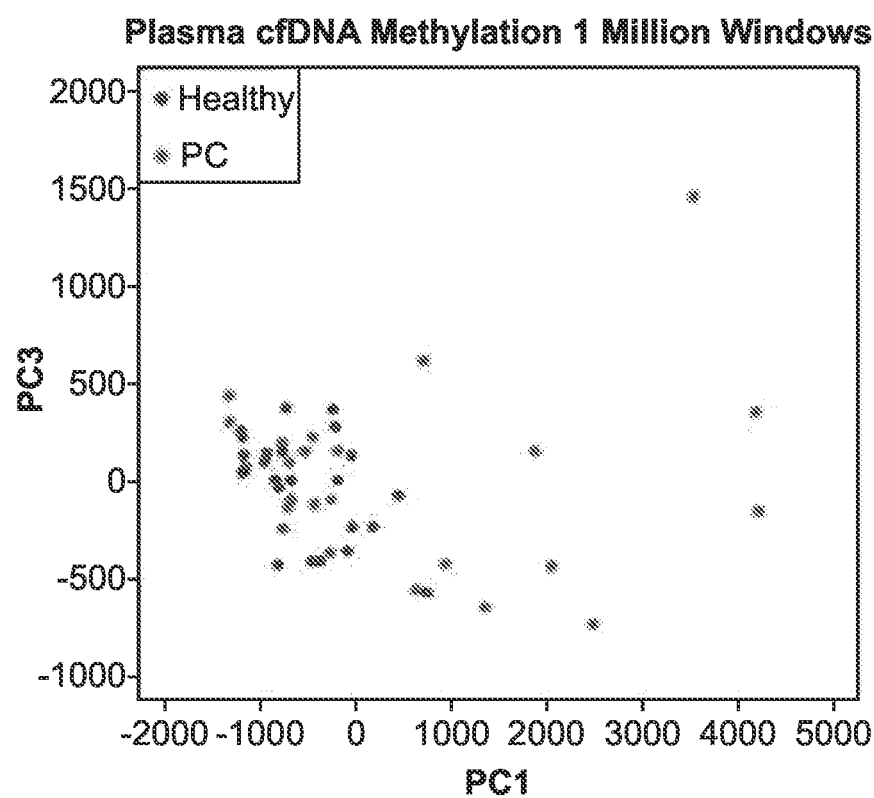
Figure 7B:
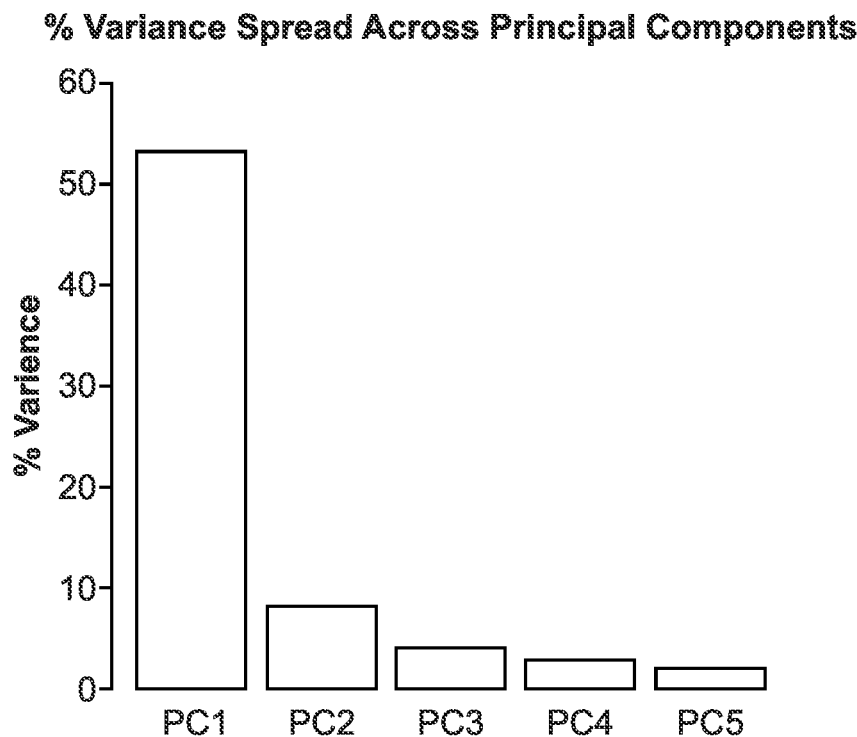
FIG. 7B shows percentage of variance for each principal component.
Figure 7C:
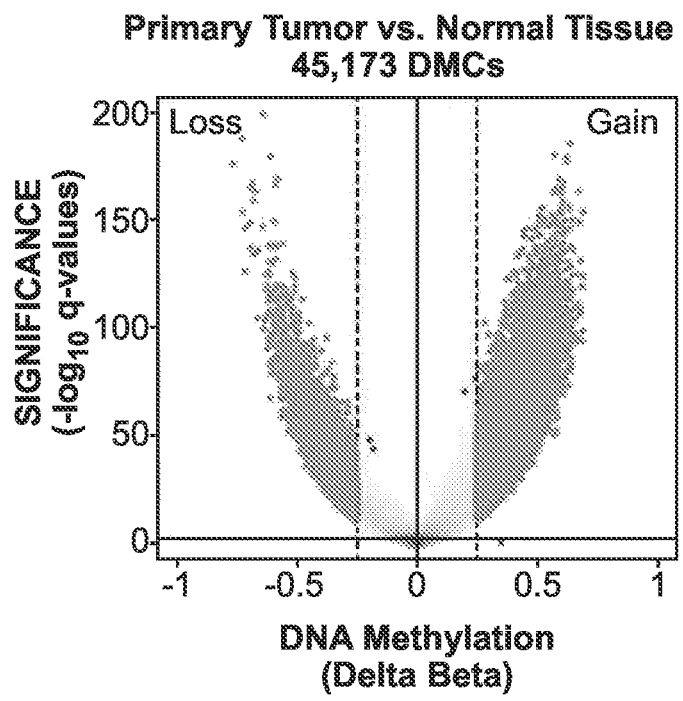
FIG. 7C shows volcano plot for tumor versus normal LCM tissue from pancreatic adenocarcinoma patients using RRBS. Total numbers of DMCs (Differentially Methylated CpGs) identified are listed. Red dots indicate the windows that reached significance after correction for multiple tests and having absolute methylation difference (absolute delta beta)>0.25.

In order to evaluate whether the differences in the cfDNA methylation profiles between cases and controls were due to the presence of ctDNA, the DNA methylation patterns of the primary tumors and normal tissue, obtained from the same patients after surgical resection, were mapped using RRBS. We identified 45,173 differentially methylated CpGs (DMCs) between tumors (n=24) versus normal (n=24) tissues (FIG. 7A-C).

Figure 7D:
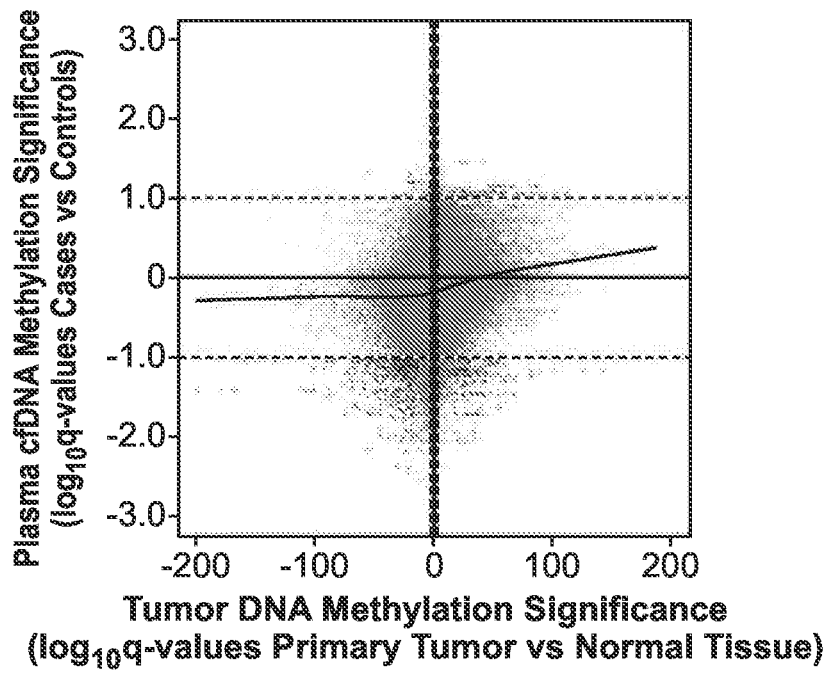
FIG. 7D shows the scatter-plot showing the significance of the DNA methylation difference for each overlapping window. X-axis shows the log 10 q values for the primary pancreatic adenocarcinoma tumor versus normal tissue from the RRBS data. If the region is hypermethylated in the tumor, the significance is showed on a positive scale. Hypomethylated regions are shown on a negative scale. Y-axis shows the log 10 q values for the plasma cfDNA methylation from pancreatic adenocarcinoma patients versus healthy donors from the cfMeDIP-seq data. Blue dots are significant in both. Red line shows the trend line.
Figure 7E:
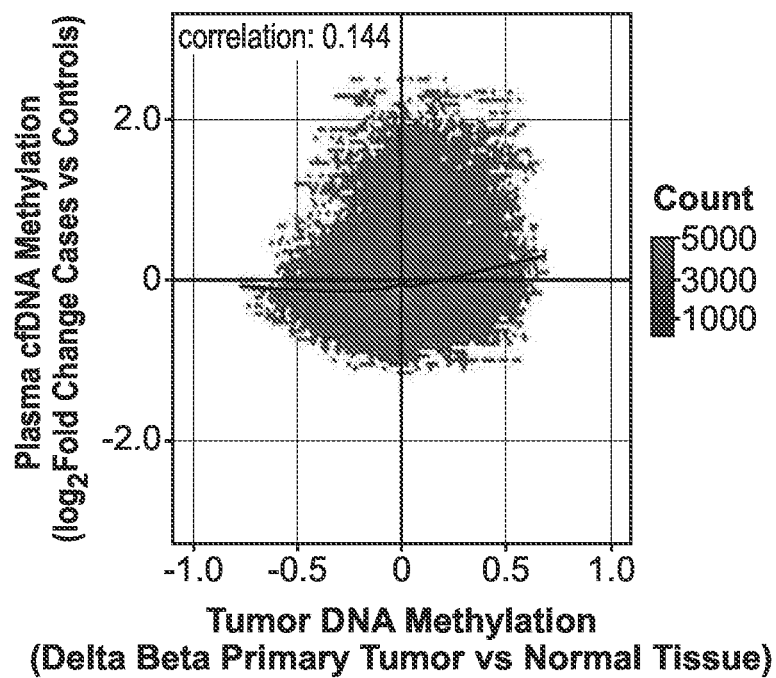
FIG. 7E shows scatter-plot showing the DNA methylation difference for each overlapping window. X-axis shows the DNA methylation difference for the primary pancreatic adenocarcinoma tumor versus normal tissue from the RRBS data. Y-axis shows the DNA methylation difference for the plasma cfDNA methylation from pancreatic adenocarcinoma patients versus healthy donors from the cfMeDIP-seq data. Blue line shows the trend line.

The utility of cfDNA methylation profiles in recapitulating methylation profiles of their original tumor was tested by examining combinations of DMCs in tumors and DMRs in cfDNA (hypermethylated in both, hypomethylated in both, hypermethylated in one and hypomethylated in the other) for enrichment relative to the background. We observed significant enrichment for tumor-specific hypermethylated and hypomethylated sites in the concordant direction in cfDNA, while tumor-specific hypermethylated sites were under-represented in cfDNA hypomethylated DMRs (FIG. 5D). Indeed, there is a correlation between the DNA methylation status for a given region in the tumor and the methylation profile in the plasma cfDNA (FIG. 7D-E).

Figure 7F:
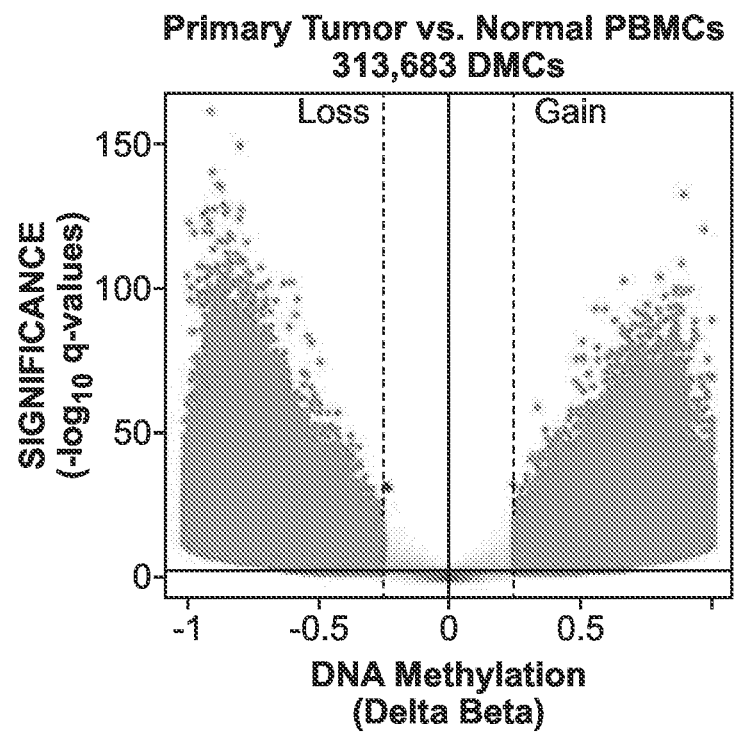
FIG. 7F shows volcano plot for LCM pancreatic adenocarcinoma tissue versus normal PBMCs using RRBS. Total numbers of DMCs (Differentially Methylated CpGs) identified are listed. Red dots indicate the windows that reached significance after correction for multiple tests and having absolute methylation difference (absolute delta beta)>0.25.
Figure 7G:
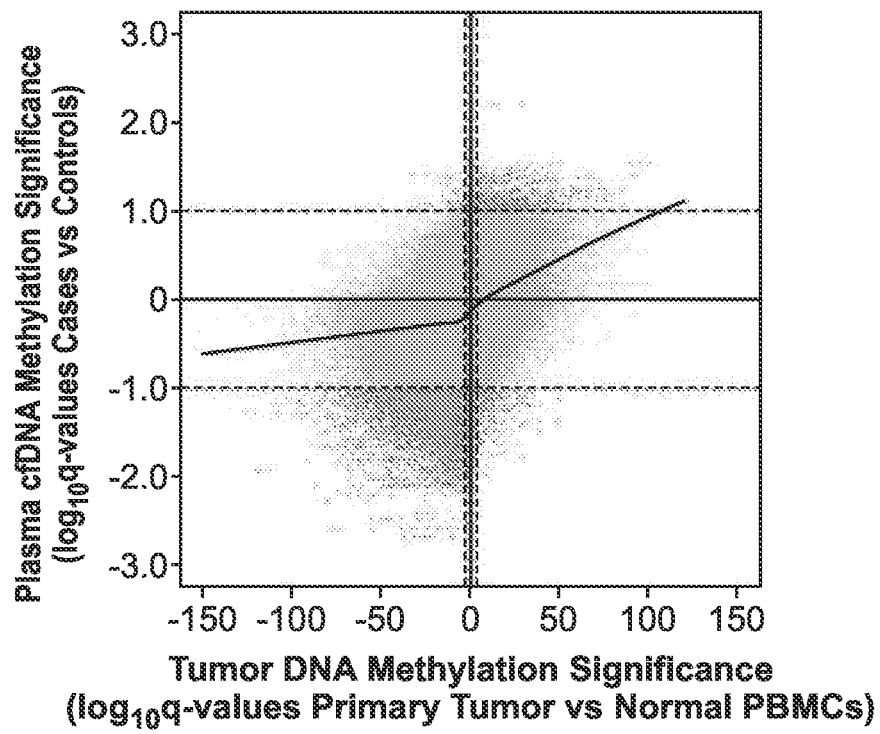
FIG. 7G shows scatter-plot showing the significance of the DNA methylation difference for each overlapping window. X-axis shows the log 10 q values for the primary pancreatic adenocarcinoma tumor versus normal PBMCs from the RRBS data. If the region is hypermethylated in the tumor, the significance is showed on a positive scale.
Figure 7H:
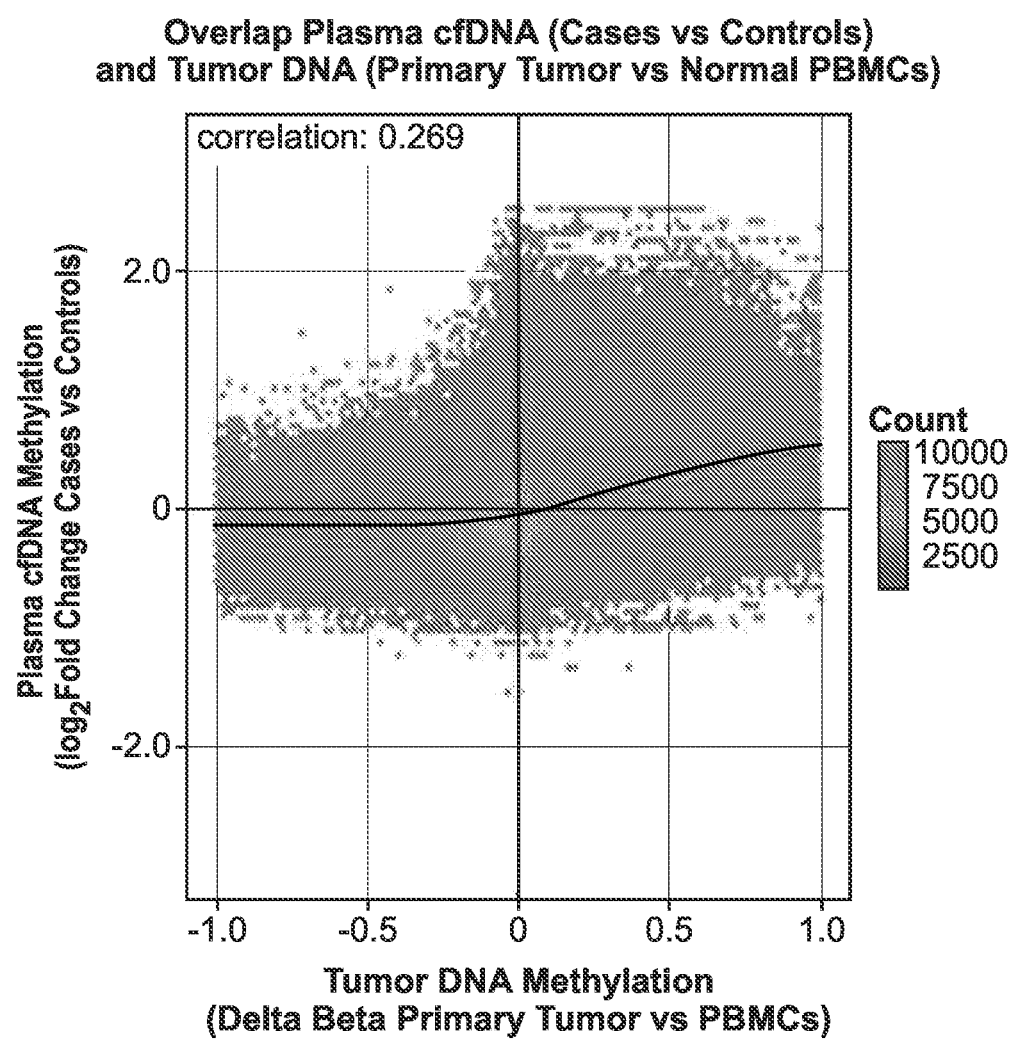
FIG. 7H shows scatter-plot showing the DNA methylation difference for each overlapping window. X-axis shows the DNA methylation difference for the primary pancreatic adenocarcinoma tumor versus normal PBMCs from the RRBS data. Y-axis shows the DNA methylation difference for the plasma cfDNA methylation from pancreatic adenocarcinoma patients versus healthy donors from the cfMeDIP-seq data.

Finally, since the majority of the plasma cfDNA molecules in cancer patients, especially at early stage, are non-tumor-derived and likely released from blood cells[14], we evaluated the DNA methylation differences between the pancreatic adenocarcinoma tumor tissue against normal Peripheral Blood Mononuclear Cells (PBMCs). We identified 313,683 DMCs between tumors (n=24) versus PBMCs (n=5) (FIG. 7F). We observed significant enrichment for tumor-specific hypermethylated and hypomethylated sites in the concordant direction in cfDNA, while tumor-specific hypermethylated sites were under-represented in cfDNA hypomethylated DMRs (FIG. 5E). Again, there is a correlation between the DNA methylation status for a given region in the tumor and the methylation profile in the plasma cfDNA (FIG. 7G-H).

Altogether, these results suggest that the difference in the circulating cfDNA methylation profile between cases and controls was largely due to the presence of tumor-derived DNA in the circulating system (FIGS. 5D-E and FIGS. 7C-H).

Plasma cfDNA Methylomes Permit Inference of Tumor-Associated Active Transcription Factor Networks Since the DMRs between cases and controls were highly enriched for tumor-derived DMRs (FIG. 5D-E), we hypothesized that cfDNA methylomes would reveal enrichment for motifs related to tumor-specific or tissue-related active transcription factors. These cfDNA methylomes could be used to infer active transcriptional networks in the tissue-of-origin of these DNA molecules. To infer the active transcriptional networks, we investigated whether the DMRs in cfDNA could uncover enrichment for transcription factor (TF) footprints, as the majority of TFs display variable binding based on DNA-methylation states of target sequences[28]. Motif analysis was carried out with the HOMER software[20] on the hypomethylated DMRs[20], separately for healthy donors (FIG. 8A) and pancreatic cancer patients (FIG. 8C), to uncover potential TF footprints.

We identified 33 motifs as hypomethylated footprints in the healthy donors as compared to the pancreatic adenocarcinoma cases and 85 motifs as hypomethylated footprints in the pancreatic adenocarcinoma cases as compared to the healthy donors.

Out of the 33 motifs identified as hypomethylated footprints in the healthy donors, we identified several TFs preferentially expressed in the hematopoietic lineage, including PU.1, Fli1, STAT5B, and KLF1 (FIGS. 8A-B).

Similarly, out of the 85 motifs identified as hypomethylated footprints in the pancreatic adenocarcinoma cases, we identified several TFs preferentially expressed in the pancreas, including RBPJL, PTF1a, Onecut1 (HNF6), and NR5A2 (FIGS. 8C-D). The TF motifs identified as hypomethylated footprints in the pancreatic adenocarcinoma cases were also frequently overexpressed in pancreatic adenocarcinoma patients from TCGA (FIG. 8E). Furthermore, we were able to identify several hypomethylated footprints in the pancreatic adenocarcinoma cases that correspond to TFs previously identified as drivers of each molecular subtypes of pancreatic cancer[24]. These included c-MYC and HIF1a (Squamous subtype drivers), NR5A2, MAFA, RBPJL, and NEUROD1 (ADEX drivers) and finally FOXA2 and HNF4A (pancreatic progenitor subtype).

Altogether, these results suggest that methylome analysis of circulating cfDNA can be used to infer active transcriptional networks within the tumor based on the differentially methylated TF footprints and potentially identify systemic shifts in immune cell populations between healthy donors and cancer patients.

Here we present a novel genome-wide DNA methylation method suitable for ultra-low input and fragmented DNA, such as circulating cell-free DNA. We were able to show that cfMeDIP-seq is very robust at low level of input DNA and allows for rapid generation of libraries. Moreover, since our method relies on the enrichment of methylated DNA, to sequence the libraries to saturation required only around 30 to 70 million reads per library, making whole genome sequencing unnecessary and significantly decreasing the associated cost. The rapid turnaround time in addition to the relatively small cost may allow for a quick translation of cfMeDIP-seq to a clinical setting.

Moreover, since cfMeDIP-seq relies on epigenetic, rather than genomic information, it could potentially be used to non-invasively monitor tissue damage in a broad set of non-malignant diseases. For instance, it could be used to monitor immune response to an infection or after cancer immunotherapy; it could be used to monitor heart DNA in the circulation after myocardial infarction or brain DNA during early stages of neurodegenerative diseases.

Finally, in the context of oncology, multiple cancer types have shown to have clinically distinct subgroups. These subgroups can be stratified by different DNA methylation profiles with prognostic value in glioblastoma[3], ependymomas[4], colorectal[5], breast[6,7], and pancreatic cancer[24] among many other cancer types. Recent data suggests that pancreatic cancer patients can be stratified into four subgroups driven by several mechanisms[24]: squamous, pancreatic progenitor, immunogenic and aberrantly differentiated endocrine exocrine (ADEX). In the circulating cfDNA methylome of pancreatic cancer patients, we were able to identify the hypomethylated footprints from TFs that drive these subtypes. For instance, we identified MYC and HIF1 alpha (Hypoxia-inducible factor 1-alpha), two pathways enriched in the squamous subtype[24]. We were also able to identify HNF4A and FOXA2; two TFs enriched in the progenitor subtype[24]. Finally, we were able to identify NR5A2, RBPJL, and MAFA, three TFs enriched in the ADEX subtype[24]. This suggests that cfMeDIP-seq could also be used as a biomarker to stratify cancer patients with a minimally invasive approach.

The invention has been described with regard to specific embodiments. It will be apparent to a person skilled in the art that variations and changes may be made while keeping within the spirit and scope of the invention. Specific embodiments disclosed herein are not intended to limit the scope of protection, which should be determined solely by the claims. All publications and references disclosed herein are incorporated in their entirety by reference.

Tables

TABLE 1

FOR primers used to generate *Enterobacteria* phage λ PCR product from Taiwo et al., 2012

| Name | Forward Primer | Reverse Primer |
|---|---|---|
| 1CpG | GAGGTGATAAAATTAACTGC (SEQ ID NO: 1) | GGCTCTACCATATCTCCTA (SEQ ID NO: 2) |
| 5CpG | CATGTCCAGAGCTCATTC (SEQ ID NO: 3) | GTTTAAAATCACTAGGCGA (SEQ ID NO: 4) |
| 1 OC pG | CTGACCATTTCCATCATTC (SEQ ID NO: 5) | GTAACTAAACAGGAGCCG (SEQ ID NO: 6) |
| 150p0 | ATGTATCCATTGAGCATTGCC (SEQ ID NO: 7) | CACGAATCAGCGGTAAAGGT( SEQ ID NO: 8) |
| 200pGL | GAGATATGGTAGAGCCGCAGA (SEQ ID NO: 9) | TTTCAGCAGCTACAGTCAGAATTT (SEQ ID NO: 10) |
| 200pGS | CGATGGGTTAATTCGCTCGTTGTGG (SEQ ID NO: 11) | GCACAACGGAAAGAGCACTG (SEQ ID NO: 12) |

TABLE 2

Number of reads and mapping efficiency of sequenced MeDIP-seq and cfMeDIP-seq libraries prepared using various concentrations of HCT116 cell line DNA sheared to mimic cfDNA, to human Hg19 genome and λ genome. For starting concentrations less than 100 ng, the samples were topped up with exogenous λ DNA to artificially increase the starting amount to 100 ng prior to MeDIP.

| Sample | # of Raw reads | # of Aligned reads to human genome (Hg19) | Mapping efficiency to human genome (Hg19) | # of Aligned reads to λ genome | Mapping efficiency to λ genome |
|---|---|---|---|---|---|
| Input | 74,504,053 | 71,343,168 | 95.76 | 12 | 0.00 |
| 100 ng Replicate 1 | 55,396,238 | 50,472,273 | 91.11 | 0 | 0.00 |
| 100 ng Replicate 2 | 66,569,209 | 60,770,277 | 91.29 | 1 | 0.00 |
| 10 ng Replicate 1 | 70,054,607 | 64,020,441 | 91.39 | 0 | 0.00 |
| 10 ng Replicate 2 | 58,297,539 | 53,308,777 | 91.44 | 0 | 0.00 |
| 5 ng Replicate 1 | 65,845,430 | 60,540,743 | 91.94 | 1 | 0.00 |
| 5 ng Replicate 2 | 64,750,879 | 59,358,412 | 91.67 | 0 | 0.00 |
| 1 ng Replicate 1 | 35,102,361 | 32,258,451 | 91.90 | 0 | 0.00 |
| 1 ng Replicate 2 | 33,881,118 | 31,194,711 | 92.07 | 0 | 0.00 |

TABLE 3A

Number of reads and mapping efficiency of sequenced cfMeDIP-seq libraries prepared using cfDNA from pancreatic cancer patients, to human Hg19 genome and λ genome.

| Case | # of Raw reads | # of Aligned Reads | Mapping efficiency to human genome (Hg19) | # of Aligned reads to λ genome | Mapping efficiency to λ genome |
|---|---|---|---|---|---|
| 1 | 49,970,366 | 46,120,982 | 92.30 | 1 | 0.00 |
| 2 | 55,642,277 | 50,829,279 | 91.35 | 0 | 0.00 |
| 3 | 48,034,998 | 43,973,048 | 91.54 | 0 | 0.00 |
| 4 | 56,274,788 | 51,456,978 | 91.44 | 0 | 0.00 |
| 5 | 50,999,157 | 46,608,023 | 91.39 | 1 | 0.00 |
| 6 | 55,127,192 | 50,906,050 | 92.34 | 0 | 0.00 |
| 7 | 53,955,550 | 49,028,646 | 90.87 | 0 | 0.00 |
| 8 | 55,482,420 | 51,194,364 | 92.27 | 1 | 0.00 |
| 9 | 57,626,914 | 53,446,965 | 92.75 | 0 | 0.00 |
| 10 | 58,397,946 | 53,904,793 | 92.31 | 0 | 0.00 |
| 11 | 59,048,723 | 54,529,214 | 92.35 | 0 | 0.00 |
| 12 | 54,514,051 | 49,619,174 | 91.02 | 1 | 0.00 |
| 13 | 70,758,028 | 63,842,005 | 90.23 | 0 | 0.00 |
| 14 | 60,317,171 | 55,124,638 | 91.39 | 0 | 0.00 |
| 15 | 45,187,670 | 41,341,336 | 91.49 | 0 | 0.00 |
| 16 | 50,755,880 | 46,309,615 | 91.24 | 2 | 0.00 |
| 17 | 51,582,370 | 47,256,012 | 91.61 | 1 | 0.00 |
| 18 | 52,081,710 | 47,763,766 | 91.71 | 0 | 0.00 |
| 19 | 53,845,426 | 48,602,035 | 90.26 | 0 | 0.00 |
| 20 | 48,133,619 | 43,658,379 | 90.70 | 0 | 0.00 |
| 21 | 54,237,903 | 49,286,048 | 90.87 | 0 | 0.00 |
| 22 | 58,627,625 | 53,654,439 | 91.52 | 1 | 0.00 |
| 23 | 52,748,183 | 49,179,765 | 93.23 | 0 | 0.00 |
| 24 | 60,072,026 | 55,046,660 | 91.63 | 0 | 0.00 |

TABLE 3B

Number of reads and mapping efficiency of sequenced cfMeDIP-seq libraries prepared using cfDNA from healthy donors, to human Hg19 genome and λ genome.

| Control | # of Raw reads | # of Aligned Reads | Mapping efficiency to human genome (Hg19) | # of Aligned reads to λ genome | Mapping efficiency to λ genome |
|---|---|---|---|---|---|
| 1 | 44,162,563 | 40,184,943 | 90.99 | 1 | 0.00 |
| 2 | 33,350,539 | 30,585,488 | 91.71 | 0 | 0.00 |
| 3 | 43,937,337 | 40,160,512 | 91.40 | 0 | 0.00 |
| 4 | 44,292,409 | 40,182,945 | 90.72 | 0 | 0.00 |
| 5 | 54,732,283 | 50,135,420 | 91.60 | 0 | 0.00 |
| 6 | 52,576,198 | 48,139,158 | 91.56 | 0 | 0.00 |
| 7 | 47,619,930 | 42,684,336 | 89.64 | 0 | 0.00 |
| 8 | 51,213,827 | 46,529,314 | 90.85 | 0 | 0.00 |
| 9 | 48,935,317 | 44,487,195 | 90.91 | 1 | 0.00 |

TABLE 3B-continued

Number of reads and mapping efficiency of sequenced cfMeDIP-seq libraries prepared using cfDNA from healthy donors, to human Hg19 genome and λ genome.

| Control | # of Raw reads | # of Aligned Reads | Mapping efficiency to human genome (Hg19) | # of Aligned reads to λ genome | Mapping efficiency to λ genome |
|---|---|---|---|---|---|
| 10 | 56,055,796 | 51,971,671 | 92.71 | 0 | 0.00 |
| 11 | 54,769,256 | 50,075,252 | 91.43 | 0 | 0.00 |
| 12 | 50,625,023 | 45,869,378 | 90.61 | 1 | 0.00 |
| 13 | 51,015,277 | 46,252,402 | 90.66 | 0 | 0.00 |
| 14 | 58,266,281 | 53,191,317 | 91.29 | 1 | 0.00 |
| 15 | 55,663,935 | 50,447,271 | 90.63 | 0 | 0.00 |
| 16 | 44,004,381 | 39,533,012 | 89.84 | 1 | 0.00 |
| 17 | 55,459,971 | 50,786,298 | 91.57 | 0 | 0.00 |
| 18 | 52,610,463 | 48,293,244 | 91.79 | 0 | 0.00 |
| 19 | 46,806,153 | 42,677,554 | 91.18 | 0 | 0.00 |
| 20 | 63,267,324 | 57,692,667 | 91.19 | 0 | 0.00 |
| 21 | 51,213,236 | 46,637,533 | 91.07 | 0 | 0.00 |
| 22 | 54,380,628 | 49,267,997 | 90.60 | 0 | 0.00 |
| 23 | 44,608,650 | 40,685,531 | 91.21 | 0 | 0.00 |
| 24 | 52,118,117 | 47,734,519 | 91.59 | 0 | 0.00 |

TABLE 4A

Corresponding gender and age of pancreatic cancer patients

| Case | Sex (1 = Male, 2 = Female) | Age Range |
|---|---|---|
| 1 | 1 | 70 < 75 |
| 2 | 2 | 65 < 70 |
| 3 | 1 | 50 < 55 |
| 4 | 1 | 65 < 70 |
| 5 | 2 | 60 < 65 |
| 6 | 2 | 80 < 85 |
| 7 | 1 | 60 < 65 |
| 8 | 2 | 70 < 75 |
| 9 | 2 | 60 < 65 |
| 10 | 1 | 50 < 55 |
| 11 | 1 | 70 < 75 |
| 12 | 2 | 50 < 55 |
| 13 | 1 | 60 < 65 |
| 14 | 2 | 75 < 80 |
| 15 | 2 | 55 < 60 |
| 16 | 2 | 80 < 85 |
| 17 | 1 | 55 < 60 |
| 18 | 2 | 55 < 60 |
| 19 | 2 | 65 < 70 |
| 20 | 2 | 60 < 65 |
| 21 | 1 | 65 < 70 |
| 22 | 1 | 65 < 70 |
| 23 | 2 | <50 |
| 24 | 1 | 65 < 70 |

TABLE 4B

Corresponding gender and age of healthy donors

| Control | Sex (1 = Male, 2 = Female) | Age Range |
|---|---|---|
| 1 | 1 | 60 < 65 |
| 2 | 2 | 55 < 60 |
| 3 | 1 | 70 < 75 |
| 4 | 1 | 85+ |
| 5 | 2 | 80 < 85 |
| 6 | 2 | <50 |
| 7 | 1 | 80 < 85 |
| 8 | 2 | 60 < 65 |
| 9 | 2 | 85+ |
| 10 | 1 | 60 < 65 |
| 11 | 1 | 70 < 75 |
| 12 | 2 | 55 < 60 |
| 13 | 1 | 50 < 55 |
| 14 | 2 | 70 < 75 |
| 15 | 2 | 70 < 75 |
| 16 | 2 | 80 < 85 |
| 17 | 1 | 50 < 55 |
| 18 | 2 | 70 < 75 |
| 19 | 2 | 70 < 75 |
| 20 | 2 | 70 < 75 |
| 21 | 1 | 75 < 80 |
| 22 | 1 | <50 |
| 23 | 2 | 60 < 65 |
| 24 | 1 | 80 < 85 |

TABLE 5

Pathology of adenocarcinoma of pancreas case samples

| Pathology Stage | Number of cases |
|---|---|
| I-II | 23 |
| III-IV | 1 |

TABLE 6A

Number of reads, mapping efficiency, bisulfite conversion efficiency and CpG coverage of sequenced RRBS libraries prepared using laser-capture microdissection-enriched (LCM) tumor samples with high tumor purity from pancreatic cancer patients.

| Tumor from Case | # of Raw reads | # of Aligned reads to human genome (Hg19) | Mapping efficiency to human genome (Hg19) | Bisulfite Conversion Efficiency | # of CpGs with a minimum coverage of 10 reads |
|---|---|---|---|---|---|
| 1 | 36,348,593 | 22,050,682 | 60.7 | 99.65 | 1,152,313 |
| 2 | 56,788,591 | 35,512,606 | 62.5 | 98.29 | 1,790,326 |
| 3 | 55,115,742 | 35,229,781 | 63.9 | 98.94 | 1,630,272 |
| 4 | 58,503,145 | 37,373,806 | 63.9 | 99.48 | 1,777,824 |
| 5 | 54,364,708 | 34,274,401 | 63.0 | 98.84 | 2,053,577 |
| 6 | 57,291,238 | 34,912,515 | 60.9 | 99.23 | 2,001,726 |
| 7 | 42,683,835 | 25,509,282 | 59.8 | 97.79 | 1,471,270 |
| 8 | 51,393,779 | 31,437,264 | 61.2 | 99.52 | 1,745,355 |
| 9 | 66,023,766 | 41,284,714 | 62.5 | 99.17 | 1,788,895 |
| 10 | 37,026,164 | 20,805,815 | 56.2 | 98.67 | 1,435,724 |
| 11 | 40,053,025 | 22,116,738 | 55.2 | 99.47 | 1,521,135 |
| 12 | 42,065,012 | 23,591,687 | 56.1 | 98.22 | 1,599,425 |
| 13 | 34,527,362 | 22,101,495 | 64.0 | 99.79 | 733,408 |
| 14 | 38,624,627 | 23,317,534 | 60.4 | 99.82 | 952,714 |
| 15 | 36,799,407 | 22,072,921 | 60.0 | 98.45 | 1,442,393 |
| 16 | 33,672,535 | 19,735,978 | 58.6 | 98.70 | 1,064,718 |
| 17 | 51,918,938 | 32,239,409 | 62.1 | 99.08 | 1,810,260 |
| 18 | 26,344,807 | 15,531,839 | 59.0 | 99.87 | 792,650 |
| 19 | 43,744,321 | 26,819,066 | 61.3 | 98.45 | 1,510,987 |
| 20 | 49,861,059 | 28,520,788 | 57.2 | 97.75 | 1,852,841 |
| 21 | 44,061,826 | 27,903,839 | 63.3 | 99.68 | 1,368,522 |
| 22 | 55,029,698 | 33,444,993 | 60.8 | 99.10 | 2,006,233 |
| 23 | 70,468,323 | 45,424,428 | 64.5 | 97.86 | 2,331,030 |
| 24 | 42,043,232 | 24,828,943 | 59.1 | 97.44 | 1,520,504 |

TABLE 6B

Number of reads, mapping efficiency, bisulfite conversion efficiency and CpG coverage of sequenced RRBS libraries prepared using laser-capture microdissection-enriched (LCM) normal tissue samples from pancreatic cancer patients healthy donors.

| Normal Tissue from Case | # of Raw reads | # of Aligned reads to human genome (Hg19) | Mapping efficiency to human genome (Hg19) | Bisulfite Conversion Efficiency | # of CpGs with a minimum coverage of 10 reads |
|---|---|---|---|---|---|
| 1 | 44,991,458 | 25,708,044 | 57.1 | 98.88 | 1,688,179 |
| 2 | 50,603,038 | 30,001,913 | 59.3 | 99.81 | 1,767,046 |
| 3 | 50,790,690 | 31,585,415 | 62.2 | 99.61 | 1,733,966 |
| 4 | 49,480,382 | 30,017,286 | 60.7 | 99.60 | 1,895,462 |
| 5 | 46,587,496 | 29,742,054 | 63.8 | 98.94 | 1,648,785 |
| 6 | 55,402,162 | 33,193,299 | 59.9 | 99.10 | 2,149,673 |
| 7 | 35,010,018 | 20,646,990 | 59.0 | 99.83 | 1,188,194 |
| 8 | 51,130,341 | 30,543,069 | 59.7 | 99.64 | 1,780,696 |
| 9 | 53,415,206 | 32,049,549 | 60.0 | 99.63 | 1,720,213 |
| 10 | 40,977,129 | 22,109,663 | 54.0 | 99.60 | 1,690,112 |
| 11 | 37,913,346 | 20,202,691 | 53.3 | 98.35 | 638,859 |
| 12 | 47,943,388 | 26,962,401 | 56.2 | 97.74 | 1,467,609 |
| 13 | 28,416,315 | 16,532,481 | 58.2 | 98.36 | 1,214,093 |
| 14 | 34,809,298 | 20,603,577 | 59.2 | 99.26 | 1,105,920 |
| 15 | 36,930,467 | 21,513,886 | 58.3 | 99.76 | 1,434,653 |
| 16 | 38,762,192 | 23,242,114 | 60.0 | 99.79 | 1,539,278 |
| 17 | 51,257,989 | 29,870,486 | 58.3 | 99.66 | 1,915,596 |
| 18 | 28,789,569 | 17,038,843 | 59.2 | 98.21 | 1,222,106 |
| 19 | 41,387,115 | 25,996,349 | 62.8 | 98.57 | 1,712,186 |
| 20 | 31,704,499 | 17,421,599 | 54.9 | 99.41 | 977,256 |
| 21 | 44,152,396 | 26,604,688 | 60.3 | 99.68 | 1,646,272 |
| 22 | 46,462,469 | 27,012,950 | 58.1 | 99.43 | 1,940,763 |
| 23 | 53,534,041 | 33,359,195 | 62.3 | 99.50 | 1,650,915 |
| 24 | 37,042,798 | 22,775,661 | 61.5 | 99.31 | 435,114 |

REFERENCES

1. Sharma, S., Kelly, T. K. & Jones, P. A. Epigenetics in cancer. *Carcinogenesis* 31, 27-36, doi:10.1093/carcin/bgp220 (2010).
2. Varley, K. E. et al. Dynamic DNA methylation across diverse human cell lines and tissues. *Genome Res* 23, 555-567, doi:10.1101/gr.147942.112 (2013).
3. Sturm, D. et al. Hotspot mutations in H3F3A and IDH1 define distinct epigenetic and biological subgroups of glioblastoma. *Cancer Cell* 22, 425-437, doi:10.1016/j.ccr.2012.08.024 (2012).
4. Mack, S. C. et al. Epigenomic alterations define lethal CIMP-positive ependymomas of infancy. *Nature* 506, 445-450, doi:10.1038/nature13108 (2014).
5. Hinoue, T. et al. Genome-scale analysis of aberrant DNA methylation in colorectal cancer. *Genome Res* 22, 271-282, doi:10.1101/gr.117523.110 (2012).
6. Stirzaker, C. et al. Methylome sequencing in triple-negative breast cancer reveals distinct methylation clusters with prognostic value. *Nat Commun* 6, 5899, doi:10.1038/ncomms6899 (2015).
7. Fang, F. et al. Breast cancer methylomes establish an epigenomic foundation for metastasis. *Sci Transl Med* 3, 75ra25, doi:10.1126/scitranslmed.3001875 (2011).
8. Mikeska, T. & Craig, J. M. DNA methylation biomarkers: cancer and beyond. *Genes (Basel)* 5, 821-864, doi:10.3390/genes5030821 (2014).
9. Diaz, L. A., Jr. & Bardelli, A. Liquid biopsies: genotyping circulating tumor DNA. *J Clin Oncol* 32, 579-586, doi:10.1200/JCO.2012.45.2011 (2014).
10. Snyder, T. M., Khush, K. K., Valentine, H. A. & Quake, S. R. Universal noninvasive detection of solid organ transplant rejection. *Proc Natl Acad Sci USA* 108, 6229-6234, doi:10.1073/pnas.1013924108 (2011).
11. Chiu, R. W. et al. Noninvasive prenatal diagnosis of fetal chromosomal aneuploidy by massively parallel genomic sequencing of DNA in maternal plasma. *Proc Natl Acad Sci USA* 105, 20458-20463, doi:10.1073/pnas.0810641105 (2008).
12. Fan, H. C., Blumenfeld, Y. J., Chitkara, U., Hudgins, L. & Quake, S. R. Noninvasive diagnosis of fetal aneuploidy by shotgun sequencing DNA from maternal blood. *Proc Natl Acad Sci USA* 105, 16266-16271, doi:10.1073/pnas.0808319105 (2008).
13. Newman, A. M. et al. An ultrasensitive method for quantitating circulating tumor DNA with broad patient coverage. *Nat Med* 20, 548-554, doi:10.1038/nm.3519 (2014).
14. Aravanis, A. M., Lee, M. & Klausner, R. D. Next-Generation Sequencing of Circulating Tumor DNA for Early Cancer Detection. *Cell* 168, 571-574, doi:10.1016/j.cell.2017.01.030 (2017).
15. Hoadley, K. A. et al. Multiplatform analysis of 12 cancer types reveals molecular classification within and across tissues of origin. *Cell* 158, 929-944, doi:10.1016/j.cell.2014.06.049 (2014).
16. Fleischhacker, M. & Schmidt, B. Circulating nucleic acids (CNAs) and cancer—a survey. *Biochim Biophys Acta* 1775, 181-232, doi:10.1016/j.bbcan.2006.10.001 (2007).
17. Taiwo, O. et al. Methylome analysis using MeDIP-seq with low DNA concentrations. *Nat Protoc* 7, 617-636, doi:10.1038/nprot.2012.012 (2012).
18. Gu, H. et al. Preparation of reduced representation bisulfite sequencing libraries for genome-scale DNA methylation profiling. *Nat Protoc* 6, 468-481, doi:10.1038/nprot.2010.190 (2011).
19. Hung, E. C., Chiu, R. W. & Lo, Y. M. Detection of circulating fetal nucleic acids: a review of methods and applications. *J Clin Pathol* 62, 308-313, doi:10.1136/jcp.2007.048470 (2009).
20. Heinz, S. et al. Simple combinations of lineage-determining transcription factors prime cis-regulatory elements required for macrophage and B cell identities. *Mol Cell* 38, 576-589, doi:10.1016/j.molcel.2010.05.004 (2010).
21. Consortium, G. T. Human genomics. The Genotype-Tissue Expression (GTEx) pilot analysis: multitissue gene regulation in humans. *Science* 348, 648-660, doi:10.1126/science.1262110 (2015).
22. Su, A. I. et al. A gene atlas of the mouse and human protein-encoding transcriptomes. *Proc Natl Acad Sci USA* 101, 6062-6067, doi:10.1073/pnas.0400782101 (2004).
23. Wu, C., Jin, X., Tsueng, G., Afrasiabi, C. & Su, A. I. BioGPS: building your own mash-up of gene annotations and expression profiles. *Nucleic Acids Res* 44, D313-316, doi:10.1093/nar/gkv1104 (2016).
24. Bailey, P. et al. Genomic analyses identify molecular subtypes of pancreatic cancer. *Nature*, doi:10.1038/nature16965 (2016).
25. Lienhard, M., Grimm, C., Morkel, M., Herwig, R. & Chavez, L. MEDIPS: genome-wide differential coverage analysis of sequencing data derived from DNA enrichment experiments. *Bioinformatics* 30, 284-286, doi:10.1093/bioinformatics/btt650 (2014).
26. Akalin, A. et al. methylKit: a comprehensive R package for the analysis of genome-wide DNA methylation profiles. *Genome Biol* 13, R87, doi:10.1186/gb-2012-13-10-r87 (2012).
27. Krueger, F. & Andrews, S. R. Bismark: a flexible aligner and methylation caller for Bisulfite-Seq applications. *Bioinformatics* 27, 1571-1572, doi:10.1093/bioinformatics/btr167 (2011).
28. Hu, S. et al. DNA methylation presents distinct binding sites for human transcription factors. *Elife* 2, e00726, doi:10.7554/eLife.00726 (2013).
29. Lui, Y. Y. et al. Predominant hematopoietic origin of cell-free DNA in plasma and serum after sex-mismatched bone marrow transplantation. *Clin Chem* 48, 421-427 (2002).
30. Snyder, M. W., Kircher, M., Hill, A. J., Daza, R. M. & Shendure, J. Cell-free DNA Comprises an In Vivo Nucleosome Footprint that Informs Its Tissues-Of-Origin. *Cell* 164, 57-68, doi:10.1016/j.cell.2015.11.050 (2016).

The invention claimed is:

1. A method for processing a nucleic acid sample of a subject, comprising:
   (a) generating a mixture comprising (i) a nucleic acid molecule derived from said nucleic acid sample of said subject and (ii) a filler deoxyribonucleic acid (DNA) molecule, wherein the filler DNA molecule is added in at least about a 9-fold excess relative to total DNA in the sample; and
   (b) incubating said mixture under conditions sufficient to enrich for a methylated region of said nucleic acid molecule, wherein said filler DNA molecule increases a fold enrichment ratio.

2. The method of claim 1, wherein said nucleic acid molecule is a deoxyribonucleic acid (DNA) molecule.

3. The method of claim 1, wherein said nucleic acid sample is a cell-free DNA (cfDNA) sample.

4. The method of claim 1, wherein said mixture in (a) comprises (i) a plurality of nucleic acid molecules comprising said nucleic acid molecule and (ii) a plurality of filler DNA molecules comprising said filler DNA molecule, and wherein (b) comprises using said plurality of filler DNA molecules to enrich for a plurality of methylated regions of said plurality of nucleic acid molecules.

5. The method of claim 4, wherein said plurality of methylated regions is enriched at a specificity of at least about 99%.

6. The method of claim 4, wherein said plurality of DNA molecules comprises at least about 5% methylated filler DNA molecules.

7. The method of claim 1, wherein said filler DNA molecule has a length of about 50 base pairs (bp) to about 800 bp.

8. The method of claim 7, wherein said length is about 100 bp to about 600 bp.

9. The method of claim 7, wherein said length is about 200 bp to about 600 bp.

10. The method of claim 4, wherein said mixture comprises at least about 50 nanograms (ng) of nucleic acid molecules.

11. The method of claim 1, wherein (b) comprises using a binder that binds to one or more methylated nucleotides of said methylated region of said nucleic acid molecule.

12. The method of claim 11, wherein said binder comprises a protein comprising a methyl-CpG-binding domain.

13. The method of claim 12, wherein said protein is a MBD2 protein.

14. The method of claim 11, wherein said binder comprises an antibody.

15. The method of claim 14, wherein said antibody is a 5-MeC antibody.

16. The method of claim 14, wherein said antibody is a 5-hydroxymethyl cytosine antibody.

17. The method of claim 11, wherein said binder exhibits a reduced level of a non-specific binding to non-methylated nucleotides of said nucleic acid molecule.

18. The method of claim 4, further comprising assaying said plurality of nucleic acid molecules or a derivative thereof to identify at least one differentially methylated region (DMR) of said nucleic acid sample.

19. The method of claim 18, wherein said DMR comprises hypermethylation.

20. The method of claim 18, wherein said DMR comprises hypomethylation.

21. The method of claim 18, wherein said assaying comprises sequencing said plurality of nucleic acid molecules or a derivative thereof.

22. The method of claim 21, wherein said sequencing does not comprise bisulfate sequencing.

23. The method of claim 18, further comprising processing said DMR with a DMR of a nucleic acid sample of a healthy control.

24. The method of claim 1, wherein said subject has or is suspected of having pancreatic adenocarcinoma (PDAC).

* * * * *

SEQUENCE LISTING

<160> NUMBER OF SEQ ID NOS: 12

<210> SEQ ID NO 1
<211> LENGTH: 20
<212> TYPE: DNA

<213> ORGANISM: Artificial Sequence
<220> FEATURE:
<223> OTHER INFORMATION: Description of Artificial Sequence: Synthetic primer

<400> SEQUENCE: 1
gaggtgataa aattaactgc                      20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ggctctacca tatctccta                       19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
catgtccaga gctcattc                        18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gtttaaaatc actaggcga                       19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
ctgaccattt ccatcattc                       19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gtaactaaac aggagccg                        18

<210> SEQ ID NO 7
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 7
atgtatccat tgagcattgc c                                               21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cacgaatcag cggtaaaggt                                                 20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagatatggt agagccgcag a                                               21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttcagcagc tacagtcaga attt                                            24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgatgggtta attcgctcgt tgtgg                                           25

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcacaacgga aagagcactg                                                 20
```